US012733839B2

(12) United States Patent
Matijevich et al.

(10) Patent No.: US 12,733,839 B2
(45) Date of Patent: Sep. 15, 2026

(54) WEARABLE DEVICE TO MONITOR MUSCULOSKELETAL LOADING, ESTIMATE TISSUE MICRODAMAGE AND PROVIDE INJURY RISK BIOFEEDBACK

(71) Applicant: VANDERBILT UNIVERSITY, Nashville, TN (US)

(72) Inventors: Emily Matijevich, Nashville, TN (US); Leon Scott, Nashville, TN (US); Karl Zelik, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 289 days.

(21) Appl. No.: 18/677,979

(22) Filed: May 30, 2024

(65) Prior Publication Data

US 2024/0324902 A1 Oct. 3, 2024

Related U.S. Application Data

(63) Continuation of application No. 17/051,218, filed as application No. PCT/US2019/029790 on Apr. 30, 2019, now Pat. No. 12,011,257.

(Continued)

(51) Int. Cl.
*A61B 5/11* (2006.01)
*A61B 5/00* (2006.01)
*A61B 5/296* (2021.01)

(52) U.S. Cl.
CPC ................ *A61B 5/11* (2013.01); *A61B 5/296* (2021.01); *A61B 5/4509* (2013.01); *A61B 5/4538* (2013.01); *A61B 5/4806* (2013.01); *A61B 5/6801* (2013.01); *A61B 5/6898* (2013.01); *A61B 5/7405* (2013.01); *A61B 5/7435* (2013.01); *A61B 5/7455* (2013.01);

(Continued)

(58) Field of Classification Search
CPC .. A61B 5/11; A61B 5/45; A61B 5/296; A61B 5/1038; A61B 5/4538; A61B 5/6801; A61B 5/6807; A61B 5/7405; A61B 5/7435; A61B 5/7455; A61B 5/746; A61B 2562/0219; A61B 2562/0247
See application file for complete search history.

(56) References Cited

U.S. PATENT DOCUMENTS

2009/0137933 A1* 5/2009 Lieberman ............ A61B 5/1117 600/595
2011/0137375 A1* 6/2011 Mcbride ............. A61B 5/1124 607/48

(Continued)

*Primary Examiner* — Chu Chuan Liu

(74) *Attorney, Agent, or Firm* — troutman pepper locke; Tim Tingkang Xia, Esq.

(57) ABSTRACT

A wearable device operably worn by a user for monitoring musculoskeletal loading on structure inside the body of the user includes a plurality of sensors, each sensor configured to be operably worn by the user at a predetermined location and configured to detect information about a biomechanical activity of musculoskeletal tissues, a limb segment orientation, and/or a loading magnitude or location thereon; and a processing unit in communication with the plurality of sensors and configured to process the detected information by the plurality of sensors to estimate the musculoskeletal loading, and communicate the estimated musculoskeletal loading to the user and/or a party of interest.

20 Claims, 39 Drawing Sheets

Related U.S. Application Data

(60) Provisional application No. 62/664,479, filed on Apr. 30, 2018.

(52) U.S. Cl.
CPC ...... *A61B 5/746* (2013.01); *A61B 2562/0219* (2013.01); *A61B 2562/0247* (2013.01)

(56) References Cited

U.S. PATENT DOCUMENTS

| | | | | |
|---|---|---|---|---|
| 2012/0154153 | A1* | 6/2012 | Agrawal .............. | A61B 5/0051<br>36/136 |
| 2017/0055880 | A1* | 3/2017 | Agrawal .............. | A61B 5/7455 |

* cited by examiner $$F_{tibia} = F_{ext} + F_{int}$$

$$F_{tibia} = \left[ F_{normal} \cos(\theta_s) + \left| \frac{M_a}{r_{AT}} \right| \right]$$

$$F_{tibia} = \left[ F_{normal} \cos(\theta_s) + \left| \frac{(COPy/insole - r_{AT}) * F_{normal}}{r_{AT}} \right| \right]$$

| | SS | | GEN | | AOC | |
|---|---|---|---|---|---|---|
| | RMSE | r | RMSE | r | RMSE | r |
| S1 | 0.46 | 0.89 | 0.75 | 0.89 | 0.52 | 0.89 |
| S2 | 0.50 | 0.84 | 0.64 | 0.84 | 0.53 | 0.84 |
| S3 | 0.45 | 0.72 | 0.67 | 0.72 | 0.48 | 0.72 |
| S4 | 0.52 | 0.90 | 0.73 | 0.90 | 0.56 | 0.90 |
| S5 | 0.61 | 0.72 | 0.71 | 0.72 | 0.61 | 0.72 |
| S6 | 0.38 | 0.58 | 0.45 | 0.58 | 0.51 | 0.58 |
| S7 | 0.58 | 0.85 | 0.72 | 0.85 | 0.66 | 0.85 |
| S8 | 0.45 | 0.26 | 0.74 | 0.26 | 0.58 | 0.26 |
| S9 | 0.57 | 0.16 | 0.86 | 0.16 | 0.69 | 0.16 |
| S10 | 0.52 | 0.57 | 0.63 | 0.57 | 0.52 | 0.57 |
| all | 0.51 | 0.87 | 0.70 | 0.73 | 0.57 | 0.83 |

FIG. 22B

| | SS | | GEN | | AOC | |
|---|---|---|---|---|---|---|
| | RMSE | r | RMSE | r | RMSE | r |
| S1 | 0.75 | 0.64 | 0.91 | 0.64 | 0.81 | 0.64 |
| S2 | 0.78 | 0.47 | 1.06 | 0.47 | 0.79 | 0.47 |
| S3 | 0.97 | 0.06 | 1.99 | 0.06 | 0.97 | 0.06 |
| S4 | 1.09 | 0.27 | 1.16 | -0.27 | 1.16 | -0.27 |
| S5 | 0.80 | 0.33 | 0.84 | 0.33 | 0.81 | 0.33 |
| S6 | 0.47 | 0.45 | 0.54 | 0.45 | 0.49 | 0.45 |
| S7 | 0.81 | 0.24 | 0.94 | 0.24 | 0.82 | 0.24 |
| S8 | 0.50 | 0.34 | 0.57 | -0.34 | 0.62 | -0.34 |
| S9 | 0.55 | 0.46 | 0.68 | 0.46 | 0.55 | 0.46 |
| S10 | 0.52 | 0.61 | 0.61 | 0.61 | 0.52 | 0.61 |
| all | 0.75 | 0.62 | 0.94 | 0.15 | 0.78 | 0.58 |

FIG. 22D

| | SS | | GEN | | AOC | |
|---|---|---|---|---|---|---|
| | RMSE | r | RMSE | r | RMSE | r |
| S1 | 0.77 | 0.63 | 0.82 | 0.63 | 0.85 | 0.63 |
| S2 | 0.91 | 0.23 | 1.22 | -0.23 | 0.99 | -0.23 |
| S3 | 0.64 | 0.01 | 1.42 | -0.01 | 0.65 | -0.01 |
| S4 | 1.17 | 0.13 | 1.21 | -0.13 | 1.18 | -0.13 |
| S5 | 0.83 | 0.30 | 0.86 | 0.30 | 0.83 | 0.30 |
| S6 | 0.46 | 0.13 | 0.56 | -0.13 | 0.53 | -0.13 |
| S7 | 0.99 | 0.44 | 1.17 | 0.44 | 1.06 | 0.44 |
| S8 | 0.45 | 0.24 | 0.61 | 0.24 | 0.45 | 0.24 |
| S9 | 0.44 | 0.65 | 0.51 | 0.65 | 0.46 | 0.65 |
| S10 | 0.62 | 0.00 | 0.79 | 0.00 | 0.63 | 0.00 |
| all | 0.77 | 0.66 | 0.96 | 0.32 | 0.80 | 0.62 |

FIG. 22F

| | SS | | GEN | | AOC | |
|---|---|---|---|---|---|---|
| | RMSE | r | RMSE | r | RMSE | r |
| S1 | 0.72 | 0.68 | 1.04 | 0.68 | 0.78 | 0.68 |
| S2 | 0.93 | 0.02 | 1.38 | 0.02 | 0.97 | 0.02 |
| S3 | 0.60 | 0.36 | 1.45 | 0.36 | 0.60 | 0.36 |
| S4 | 1.15 | 0.20 | 1.17 | 0.20 | 1.15 | 0.20 |
| S5 | 0.66 | 0.66 | 0.88 | 0.66 | 0.71 | 0.66 |
| S6 | 0.41 | 0.49 | 0.43 | 0.49 | 0.47 | 0.49 |
| S7 | 0.81 | 0.68 | 1.30 | 0.68 | 0.96 | 0.68 |
| S8 | 0.43 | 0.36 | 0.49 | 0.36 | 0.44 | 0.36 |
| S9 | 0.32 | 0.84 | 0.57 | 0.84 | 0.42 | 0.84 |
| S10 | 0.62 | 0.15 | 0.77 | -0.15 | 0.78 | -0.15 |
| all | 0.71 | 0.72 | 1.01 | 0.11 | 0.77 | 0.66 |

FIG. 22H

| | SS | | GEN | | AOC | |
|---|---|---|---|---|---|---|
| | RMSE | r | RMSE | r | RMSE | r |
| S1 | 0.94 | 0.28 | 1.07 | 0.28 | 0.95 | 0.28 |
| S2 | 0.86 | 0.38 | 1.21 | 0.38 | 0.86 | 0.38 |
| S3 | 0.47 | 0.69 | 1.48 | 0.69 | 0.48 | 0.69 |
| S4 | 1.05 | 0.45 | 1.07 | 0.45 | 1.06 | 0.45 |
| S5 | 0.77 | 0.48 | 0.85 | 0.48 | 0.77 | 0.48 |
| S6 | 0.38 | 0.57 | 0.39 | 0.57 | 0.39 | 0.57 |
| S7 | 1.02 | 0.40 | 1.17 | 0.40 | 1.02 | 0.40 |
| S8 | 0.35 | 0.65 | 0.40 | 0.65 | 0.35 | 0.65 |
| S9 | 0.52 | 0.44 | 0.55 | 0.44 | 0.53 | 0.44 |
| S10 | 0.55 | 0.46 | 0.63 | 0.46 | 0.56 | 0.46 |
| all | 0.74 | 0.69 | 0.95 | 0.35 | 0.74 | 0.69 |

FIG. 22J

| | SS | | GEN | | AOC | |
|---|---|---|---|---|---|---|
| | RMSE | r | RMSE | r | RMSE | r |
| S1 | 0.47 | 0.88 | 0.73 | 0.88 | 0.53 | 0.88 |
| S2 | 0.40 | 0.91 | 0.97 | 0.91 | 0.45 | 0.91 |
| S3 | 0.52 | 0.59 | 1.52 | 0.59 | 0.57 | 0.59 |
| S4 | 0.58 | 0.87 | 0.71 | 0.87 | 0.70 | 0.87 |
| S5 | 0.49 | 0.83 | 0.62 | 0.83 | 0.50 | 0.83 |
| S6 | 0.41 | 0.49 | 0.57 | 0.49 | 0.57 | 0.49 |
| S7 | 0.55 | 0.87 | 0.87 | 0.87 | 0.65 | 0.87 |
| S8 | 0.40 | 0.49 | 0.60 | 0.49 | 0.57 | 0.49 |
| S9 | 0.36 | 0.78 | 0.43 | 0.78 | 0.40 | 0.78 |
| S10 | 0.35 | 0.83 | 0.47 | 0.83 | 0.37 | 0.83 |
| all | 0.46 | 0.89 | 0.81 | 0.61 | 0.54 | 0.85 |

FIG. 22L

| | SS RMSE | GEN RMSE | AOC RMSE |
|---|---|---|---|
| active_peak | 0.51 | 0.70 | 0.57 |
| impact_peak | 0.75 | 0.94 | 0.78 |
| VALR | 0.77 | 0.96 | 0.80 |
| TVI | 0.71 | 1.01 | 0.77 |
| speed | 0.74 | 0.95 | 0.74 |
| incline | 0.46 | 0.81 | 0.54 |

| | SS r | GEN r | AOC r |
|---|---|---|---|
| active_peak | 0.87 | 0.73 | 0.83 |
| impact_peak | 0.62 | 0.15 | 0.58 |
| VALR | 0.66 | 0.32 | 0.62 |
| TVI | 0.72 | 0.11 | 0.66 |
| speed | 0.69 | 0.35 | 0.69 |
| incline | 0.89 | 0.61 | 0.85 |

* RMSE and correlation (r) across all subjects & trials

| Correlations (r) | Max | Impulse |
|---|---|---|
| S1 | 0.93 | 0.89 |
| S2 | 0.79 | 0.98 |
| S3 | 0.79 | 0.65 |
| S4 | 0.96 | 0.99 |
| S5 | 0.94 | 0.98 |
| S6 | 0.69 | 0.88 |
| S7 | 0.94 | 0.97 |
| S8 | 0.59 | 0.89 |
| S9 | 0.73 | 0.87 |
| S10 | 0.54 | 0.91 |

| | RMSE | r |
|---|---|---|
| S1 | 1.04 | 0.93 |
| S2 | 0.88 | 0.79 |
| S3 | 1.17 | 0.67 |
| S4 | 0.94 | 0.96 |
| S5 | 1.02 | 0.94 |
| S6 | 0.98 | 0.69 |
| S7 | 0.86 | 0.94 |
| S8 | 0.84 | 0.59 |
| S9 | 1.13 | 0.73 |
| S10 | 1.06 | 0.54 |
| ALL | 1.00 | 0.88 |

WEARABLE DEVICE TO MONITOR MUSCULOSKELETAL LOADING, ESTIMATE TISSUE MICRODAMAGE AND PROVIDE INJURY RISK BIOFEEDBACK

CROSS-REFERENCE TO RELATED PATENT APPLICATIONS

This application is a continuation application of U.S. patent application Ser. No. 17/051,218, filed Oct. 28, 2020, now allowed, which is a U.S. national phase application of PCT patent application No. PCT/US2019/029790, filed Apr. 30, 2019, which itself claims priority to and the benefit of U.S. provisional patent application No. 62/664,479, filed Apr. 30, 2018, which are incorporated herein by reference in their entireties.

STATEMENT AS TO RIGHTS UNDER FEDERALLY-SPONSORED RESEARCH

This invention was made with government support under Contract No. R01EB028105 awarded by the National Institute of Biomedical Imaging and Bioengineering, and Contract No. K12HD073945 awarded by the Eunice Kennedy Shriver National Institute of Child Health and Human Development. The government has certain rights in the invention.

FIELD OF THE INVENTION

This invention relates to a wearable device to monitor musculoskeletal loading, estimate tissue microdamage and provide injury risk biofeedback and applications of the same.

BACKGROUND INFORMATION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Running is one of the most popular and widely accessible forms of physical activity, delivering a plethora of physical and mental health benefits. But there's a major problem: running has staggering attrition rates. In a recent study, 30% of runners quit their newly adopted running program within six months of starting, and injuries were the leading reason why they stopped. Bone stress fractures are one of the most common and debilitating overuse injuries. A person's bones experience repetitive forces each time they go for a run, resulting in tiny microcracks in the bone. Afterwards, bones naturally heal themselves (a process called remodeling). However, if a person's bones undergo so much repetitive loading that remodeling cannot keep up, then microcracks accumulate in the bone and eventually become painful due to the excessive damage. This type of overuse injury is known as stress fractures, and they are common in runners, military cadets, dancers and other athletes. Stress fractures commonly occur in the tibia (shank) and calcaneus (heel) bones. Once injured, people are often sidelined for weeks or months, and many do not continue running after healing. Thus, they lose out on the major health benefits, and are more likely to add to the healthcare burden resulting from our increasingly sedentary society. The best way to keep people fit, active and healthy, is to keep them injury-free.

If excessive bone forces could be identified early (i.e., before injury/pain), then extra rest could be taken, or training altered, to allow the bone more time to remodel/heal. However, there are currently no validated technologies or interventions that enable runners, scientists or clinicians to monitor these force-related risk factors ecologically, or to predict/prevent bone stress injuries in daily life.

Various researchers have attempted to understand bone stress fractures by measuring ground reaction forces (GRFs), with the hope that GRF impact peaks or loading rates might reflect bone loading. GRFs are appealing because, in contrast to bone loading, they can be easily measured non-invasively; however, it can be shown analytically (via Newton-Euler laws of motion) that bone forces are a function of more than just GRFs. Typically, the vast majority of bone loading is due to muscle contractions. GRF magnitude is generally only a small fraction of the total bone loading. For instance, during running peak GRFs are typically 2-3 times body weight (BW), whereas peak tibia bone forces are typically 8-12 times BW. Moreover, peak bone loading occurs in midstance, while GRF impact peaks occur near initial foot contact.

While bone load can be estimated accurately and reliably in a motion analysis laboratory using specialized measurement equipment, this would require a runner to do all their training under laboratory supervision, which is completely impractical and too costly for millions of runners.

In addition, low back pain is a disabling condition experienced by 60-85% of adults within their lifetime, and one of the leading causes of years lived with disability and missed work. Low back pain is particularly common among individuals who perform repetitive or heavy lifting, at home or at their job. Prolonged leaning and other postures have also been implicated as potential risk factors, which contribute to cumulative spinal loading and potential overuse. The etiology of low back pain is multifactorial, but two key risk factors that occur during daily activities are overuse or overloading of the spinal discs and muscles. In vivo and in vitro evidence indicates that tissue injury (and resultant pain) can occur as the result of a single high-force event, or due to repetitive forces (accumulation of micro-trauma leading to overuse injury).

High forces on the low back occur during common daily activities. Certain postures and actions, such as leaning and lifting, place elevated loads on the lumbar spine, and these loads applied repetitively can predispose individuals to risk of low back injuries, such as strains, disc degeneration and herniation, which can impinge on nerves and cause pain. Training proper lifting technique is helpful; however, even with proper technique the loads on the spine can be large (e.g., multiple times body weight). Thus training alone is insufficient for preventing low back injury and a similar solution that notified users of excessive damage accumulation in the low back would be beneficial.

Therefore, a heretofore unaddressed need exists in the art to address the aforementioned deficiencies and inadequacies.

SUMMARY OF THE INVENTION

In one aspect, the invention relates to a wearable device configured to be operably worn by a user for monitoring ankle moment, calf muscle force, and/or Achilles tendon force. The wearable device comprises a plurality of sensors, each sensor configured to be operably worn by the user to detect information about a biomechanical activity, the plurality of sensors comprising one or more force sensors configured to be located under a foot of the user, and one or more motion sensors configured to be located on the foot and/or shank segment of the user; and a processing unit in communication with the plurality of sensors and configured to process the detected information by the plurality of sensors to estimate the ankle moment, calf muscle force, and/or Achilles tendon force by combining force magnitude and center of pressure data from the one or more force sensors with body segment orientation data derived from the one or more motion sensors, and communicate the estimated ankle moment, calf muscle force, and/or Achilles tendon force to the user and/or a party of interest.

In one embodiment, the plurality of sensors further comprises one or more electromyography (EMG) electrodes.

In one embodiment, the one or more motion sensors comprise inertial measurement units (IMUs), flex sensors, goniometers, or a combination thereof.

In one embodiment, each IMU comprises at least one accelerometer and/or at least one gyroscope used for estimating the linear motion and/or angular motion of a limb segment on which said IMU is located.

In one embodiment, the one or more force sensors comprise pressure or force sensors, pressure-sensing insoles, pressure-sensing fabrics, strain gages, muscle sensors, or a combination thereof.

In one embodiment, the detected information by the plurality of sensors is processed by statistical modeling combined with biomechanical algorithms.

In one embodiment, the statistical modeling comprises linear regression and/or other sensor fusion algorithms.

In one embodiment, the biomechanical algorithms comprise physics-based equations of motion applied to a model of the musculoskeletal system.

In one embodiment, the detected information by the plurality of sensors is processed by a method of inverse dynamics or machine learning, or a combination thereof.

In one embodiment, the processing unit is further configured to estimate musculoskeletal loading using reference data that is either stored on data storage means in communication with the processing unit or reference data that has been collected or inputted from the specific user and used to calibrate or establish the processing algorithm.

In one embodiment, the reference data are obtained by lab-based sensors, and the data storage means comprises a database, a cloud storage system, and/or a computer readable memory.

In one embodiment, the processing unit is further configured to alert the user when the musculoskeletal loading or microdamage is greater than a threshold that has been predetermined or a threshold that has been calibrated for the specific user.

In one embodiment, the processing unit is further configured to advise the user on when and how to adjust their movement, actions or physical activity type and duration so as to reduce injury risks.

In one embodiment, the processing unit is further configured to communicate to a computer, a smartphone, a smartwatch, a tablet or other user feedback or data acquisition device for outputting at least one of the following: estimated musculoskeletal loading, alert and advice, estimates of microdamage or microdamage accumulation, and/or injury risk, and storing the estimated musculoskeletal loading, alert and advice, estimates of microdamage or microdamage accumulation, and/or injury risk, and inputting user inputs.

In one embodiment, the wearable device further comprises a biofeedback unit in communication with the processing unit for outputting or displaying at least one of the estimated musculoskeletal loading, alert and advice, estimates of microdamage or microdamage accumulation, and/or injury risk using audible, visual, tactile, haptic, thermal, electrical or other biofeedback means, and storing the estimated musculoskeletal loading, alert and advice, estimates of damage accumulation, and/or injury risk.

In one embodiment, the biofeedback unit comprises a user interface device for user inputs.

In one embodiment, the user inputs comprise height, weight, body mass index, age, gender, diet, training schedule, subjective pain/fatigue, bone cross-sectional area, bone geometry, bone density, bone composition, GPS position, altitude of the user and/or other personal health or demographic data.

In one embodiment, one or more additional motion sensors are configured to be located on one or more additional segments of the user beyond the foot or shank.

In one embodiment, the plurality of sensors further comprises one or more activity trackers.

In another aspect, the invention relates to a method for monitoring ankle moment, calf muscle force, and/or Achilles tendon force of a user using the wearable device as disclosed above. The method comprises receiving information about biomechanical activity from the plurality of sensors; estimating bio-information of the body structure based on the received information from the plurality of sensors; and communicating the estimated bio-information to the user and/or a party of interest.

In one aspect, the invention relates to a wearable device operably worn by a user for monitoring musculoskeletal loading and/or damage on structures inside the body of the user.

In one embodiment, the wearable device includes a plurality of sensors, each sensor operably worn by the user at a predetermined location and configured to detect information about a biomechanical activity of musculoskeletal tissues, a limb segment orientation, and/or a loading magnitude or location thereon; and a processing unit in communication with the plurality of sensors and configured to process the detected information by the plurality of sensors to estimate the musculoskeletal loading, and communicate the estimated musculoskeletal loading to the user and/or a party of interest.

In one embodiment, the body structure of the user is a tibia bone, a calcaneus bone, a lumbar spine, or other bone, muscle, tendon, joint or musculoskeletal structure inside the body.

In one embodiment, these predetermined locations may be unilateral across one leg/foot only or bilateral across a pair of legs/feet. In another embodiment, these predetermined locations may be a low back, or any desired parts of the user.

In one embodiment, the plurality of sensors comprises one or more motion/orientation sensors, and one or more force/muscle sensors. In one embodiment, the plurality of sensors further comprises one or more electromyography (EMG) electrodes.

In one embodiment, the one or more motion/orientation sensors comprise inertial measurement units (IMUs), flex sensors, goniometers, or a combination thereof. In one embodiment, each IMU comprises at least one accelerometer and/or at least one gyroscope adapted for estimating the angular orientation and/or acceleration of a limb segment on which said IMU is located.

In one embodiment, the one or more force/muscle sensors comprise pressure or force sensors, pressure-sensing fabrics, strain gages, muscle sensors, or a combination thereof.

In one embodiment, data detected by pressure or force sensors are processed to provide an estimate of force between a body part of interest and a surface, e.g., perpendicular force between the foot and the shoe, and a weighted average of each pressure or force sensor is used to estimate spatial center of pressure between body part of interest associated with the body structure of the user and a surface.

In one embodiment, the detected information by the plurality of sensors is processed by statistical modeling combined with biomechanical algorithms. In one embodiment, the statistical modeling comprises linear regression and sensor fusion algorithms. In one embodiment, the biomechanical algorithms comprise physics-based equations of motion applied to a model of the musculoskeletal system.

In one embodiment, the detected information by the plurality of sensors is processed by a method of inverse dynamics or machine learning, or a combination thereof.

In one embodiment, the processing unit is further configured to estimate musculoskeletal loading using reference data that is either stored on data storage means in communication with the processing unit or reference data that has been collected or inputted from the specific user and used to calibrate or establish the processing algorithm. In one embodiment, the reference data are obtained by lab-based sensors, and the data storage means comprises a database, a cloud storage system, and/or a computer readable memory.

In one embodiment, the processing unit is further configured to alert the user when the musculoskeletal loading and/or microdamage accumulation is greater than a threshold that has been predefined or a threshold that has been calibrated for the specific user.

In one embodiment, the processing unit is further configured to advise the user on when and how to adjust their movement, actions or physical activity type, duration or training schedule so as to reduce injury risks.

In one embodiment, the processing unit is further configured to communicate to a computer, a smartphone, a smartwatch, a tablet or other user feedback or data acquisition device for outputting at least one of the following: estimated musculoskeletal loading, alert and advice, estimates of microdamage or microdamage accumulation, and/or probability of fracture, and storing the estimated musculoskeletal loading, alert and advice, estimates of microdamage or microdamage accumulation, and/or probability of fracture, and inputting user inputs.

In one embodiment, the wearable device further comprises a biofeedback unit in communication with the processing unit for outputting or displaying at least one of the estimated musculoskeletal loading, alert and advice, estimates of microdamage or microdamage accumulation, and/or probability of fracture using audible, visual, tactile, haptic, thermal, electrical or other biofeedback means, and storing the estimated musculoskeletal loading, alert and advice, estimates of damage accumulation, and/or probability of fracture.

In one embodiment, the biofeedback unit comprises a user interface device for user inputs. In one embodiment, the user inputs comprise height, weight, body mass index, age, gender, diet, training schedule, subjective pain/fatigue, bone cross-sectional area, bone geometry, bone density, bone composition, GPS position, altitude of the user and/or other personal health or demographic data.

In another aspect, the invention relates to a wearable device operably worn by a user for monitoring neuromuscular, physiological, biomechanical and/or musculoskeletal activity of a body structure of the user.

In one embodiment, the wearable device includes a plurality of sensors, each sensor operably worn by the user at a predetermined location and configured to detect information about neuromuscular, physiological, biomechanical and/or musculoskeletal activity thereon; and a processing unit in communication with the plurality of sensors and configured to process the detected information by the plurality of sensors to estimate bio-information of the body structure, and communicate the estimated bio-information to the user and/or a party of interest.

In one embodiment, the body structure of the user is a tibia bone, a calcaneus bone, a lumbar spine, or other bone, muscle, tendon, joint or musculoskeletal structure inside the body.

In one embodiment, the bio-information of the body structure comprises musculoskeletal loading, or musculoskeletal structure stress or strain.

In one embodiment, the bio-information further comprises data acquired from additional sensors that monitor sleep patterns, rest time between physical activity or other markers of rest or tissue remodeling.

In one embodiment, the plurality of sensors comprises one or more motion/orientation sensors, and one or more force/muscle sensors. In one embodiment, the plurality of sensors further comprises one or more electromyography (EMG) electrodes.

In one embodiment, the one or more motion/orientation sensors comprise inertial measurement units (IMUs), flex sensors, goniometers, or a combination thereof, and wherein the one or more force/muscle sensors comprise pressure or force sensors, pressure-sensing fabrics, strain gages, muscle sensors, or a combination thereof.

In one embodiment, the detected information by the plurality of sensors is processed by regression and sensor fusion algorithms, inverse dynamics algorithms, or machine learning algorithms.

In one embodiment, the processing unit is further configured to compute musculoskeletal loading using reference data stored on data storage means in communication with the processing unit or reference data that has been used to calibrate or establish the processing algorithm, so as to determine a condition of the body structure based on the computed loading, the condition including a normal condition or a graduated risk of injury.

In one embodiment, the reference data are obtained by motion analysis lab-based sensors, and the data storage means comprises a database, a cloud storage system, and/or a computer readable memory.

In one embodiment, the processing unit is further configured to communicate to a computer, a smartphone, a smartwatch, a tablet, or other user feedback or data acquisition device for outputting the condition of the body structure, and/or alert and advice when the body structure is in the elevated risk of injury using audible, visual, tactile, haptic, thermal, electrical or other biofeedback means, storing the condition of the body structure, and/or alert and advice, and inputting user inputs.

In one embodiment, the wearable device further comprises a biofeedback unit in communication with the processing unit for outputting and/or displaying the condition of the body structure, and/or alert and advice when the body structure is in the graduated risk of injury using audible, visual, tactile, haptic, thermal, electrical or other biofeedback means, and storing the condition of the body structure, and/or alert and advice when the body structure is in the graduated risk of injury.

In one embodiment, the biofeedback unit comprises a user interface device for user inputs. In one embodiment, the user inputs comprise height, weight, body mass index, age, gender, diet, training schedule, subjective pain/fatigue, bone cross-sectional area, bone density, bone composition, GPS position, altitude of the user and/or other personal health or demographic data.

In yet another aspect, the invention relates to a method for monitoring neuromuscular, physiological, biomechanical and/or musculoskeletal activity of a body structure of the user using a wearable device including a plurality of sensors, each sensor worn by the user at a predetermined location. In one embodiment, these predetermined locations may be unilateral across one leg/foot only or bilateral across a pair of legs/feet. In another embodiment, these predetermined locations may be a low back, or any desired parts of the user.

In one embodiment, the method includes receiving information about neuromuscular, physiological, biomechanical and/or musculoskeletal activity from the plurality of sensors; estimating bio-information of the body structure based on the received information from the plurality of sensors; and communicating the estimated bio-information to the user and/or a party of interest.

In one embodiment, the bio-information of the body structure comprises musculoskeletal loading, or musculoskeletal structure stress or strain.

In one embodiment, the bio-information further comprises data acquired from additional sensors that monitor sleep patterns, rest time between physical activity or other markers of tissue rest or remodeling.

In one embodiment, the estimating step is performed by regression and sensor fusion algorithms, inverse dynamics algorithms, or machine learning algorithms.

In one embodiment, the estimating step computes bio-information using reference data to calibrate or establish the processing algorithm, so as to determine a condition of the body structure based on the estimated musculoskeletal loading, the condition including a normal condition or a graduated risk of injury.

In one embodiment, the reference data are obtained by motion analysis lab-based sensors.

In one embodiment, the communicating step comprises for outputting or displaying the condition of the body structure, and/or alert and advice when the body structure is in the elevated risk of injury or the injured condition using audible, visual, tactile, haptic, thermal, electrical or other biofeedback means, and storing the condition of the body structure, and/or alert and advice.

In a further aspect, the invention relates to a non-transitory computer-readable medium storing instructions which, when executed by one or more processors, cause a wearable device to perform a method for monitoring neuromuscular, physiological, biomechanical and/or musculoskeletal activity of a body structure of a user wearing the wearable device, the wearable device including a plurality of sensors, each sensor placed at a predetermined location. The method comprises receiving information about neuromuscular, physiological, biomechanical and/or musculoskeletal activity from the plurality of sensors; estimating bio-information of the body structure based on the received information from the plurality of sensors; and communicating the estimated bio-information to the user and/or a party of interest.

In one embodiment, the bio-information of the body structure comprises musculoskeletal loading, or musculoskeletal structure stress or strain. In one embodiment, the bio-information further comprises data acquired from additional sensors that monitor sleep patterns, rest time between physical activity or other markers of tissue rest or remodeling.

In one embodiment, the estimating step is performed by regression and sensor fusion algorithms, inverse dynamics algorithms, or machine learning algorithms.

In one embodiment, the estimating step uses the bio-information calibrated or established using reference data, so as to determine a condition of the body structure based on the estimation, the condition including a normal condition or a graduated risk of injury.

In one embodiment, the communicating step comprises for outputting the condition of the body structure, and/or alert and advice when the body structure is in the elevated risk of injury or the injured condition using audible, visual, tactile, haptic, thermal, electrical or other biofeedback means, and storing the condition of the body structure, and/or alert and advice.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIGS. 22A-22M show lab tibia forces and estimated tibia forces and their corrections processed using linear regression with different subject calibration techniques under different conditions, according to embodiments of the invention.

DETAILED DESCRIPTION OF THE INVENTION

Figure 1:
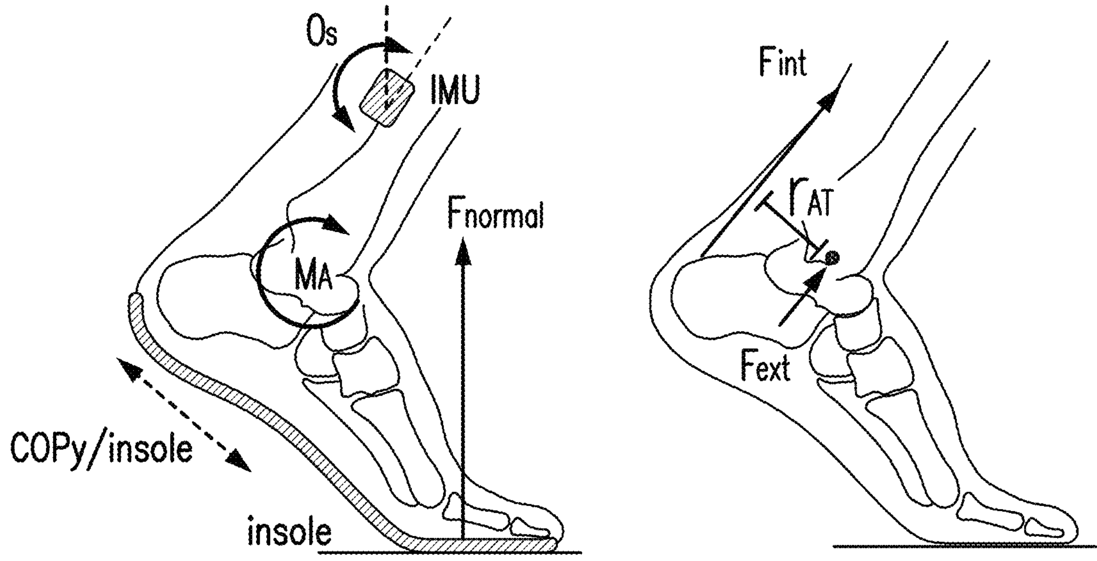
FIG. 1 shows a simplified inverse dynamic approach according to embodiments of the invention. The top equation is the full equations of motion. The remaining equations are simplified examples. Similar equations that serve as approximations of the full equations of motion could also be implemented.

The invention will now be described more fully hereinafter with reference to the accompanying drawings, in which exemplary embodiments of the invention are shown. The invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used in this invention, the phrase "at least one of A, B, and C" should be construed to mean a logical (A or B or C), using a non-exclusive logical OR. As used herein, the term "and/or" includes any and all combinations of one or more of the associated listed items.

The apparatuses and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system. By way of example, an element, or any portion of an element, or any combination of elements may be implemented as a "processing system" that includes one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

One of the objectives of the invention is to provide a wearable device to monitor musculoskeletal loading, estimate tissue microdamage and provide injury risk biofeedback.

In one aspect of the invention, the wearable device operably worn by a user for monitoring musculoskeletal loading on a body structure of the user includes a plurality of sensors, each sensor operably worn by the user at a predetermined location and configured to detect information about a biomechanical activity of musculoskeletal tissues, a limb segment orientation, and/or a loading magnitude or location thereon; and a processing unit in communication with the plurality of sensors and configured to process the detected information by the plurality of sensors to estimate the musculoskeletal loading, and communicate the estimated musculoskeletal loading to the user and/or a party of interest. The processing unit may include one or more processors or microprocessors, or a controller or microcontroller.

The body structure of the user is a tibia bone, a calcaneus bone, a lumbar spine, or other bone, muscle, tendon, joint or musculoskeletal structure inside the body. These predetermined locations may be unilateral across one leg/foot only or bilateral across a pair of legs/feet. These predetermined locations may be a low back, or any desired parts of the user.

In one embodiment, the plurality of sensors includes one or more motion/orientation sensors, and one or more force/muscle sensors. In one embodiment, the plurality of sensors further comprises one or more electromyography (EMG) electrodes.

In one embodiment, the one or more motion/orientation sensors include inertial measurement units (IMUs), flex sensors, goniometers, or a combination thereof. In one embodiment, each IMU includes at least one accelerometer and/or at least one gyroscope adapted for estimating the angular orientation and/or acceleration of a limb segment on which said IMU is located.

In one embodiment, the one or more force/muscle sensors include pressure or force sensors, pressure-sensing fabrics, strain gages, muscle sensors, or a combination thereof.

In one embodiment, data detected by pressure or force sensors are processed to provide an estimate of force between a body part of interest and a surface, e.g., perpendicular force between the foot and the shoe, and a weighted average of each pressure or force sensor is used to estimate spatial center of pressure between body part of interest associated with the body structure of the user and a surface.

In one embodiment, the detected information by the plurality of sensors is processed by statistical modeling combined with biomechanical algorithms. In one embodiment, the statistical modeling includes linear regression and sensor fusion algorithms. In one embodiment, the biomechanical algorithms includes physics-based equations of motion applied to a model of the musculoskeletal system, for example, the equations listed in FIG. 1. In one embodiment, the detected information by the plurality of sensors is processed by a method of inverse dynamics or machine learning, or a combination thereof.

Figure 4:
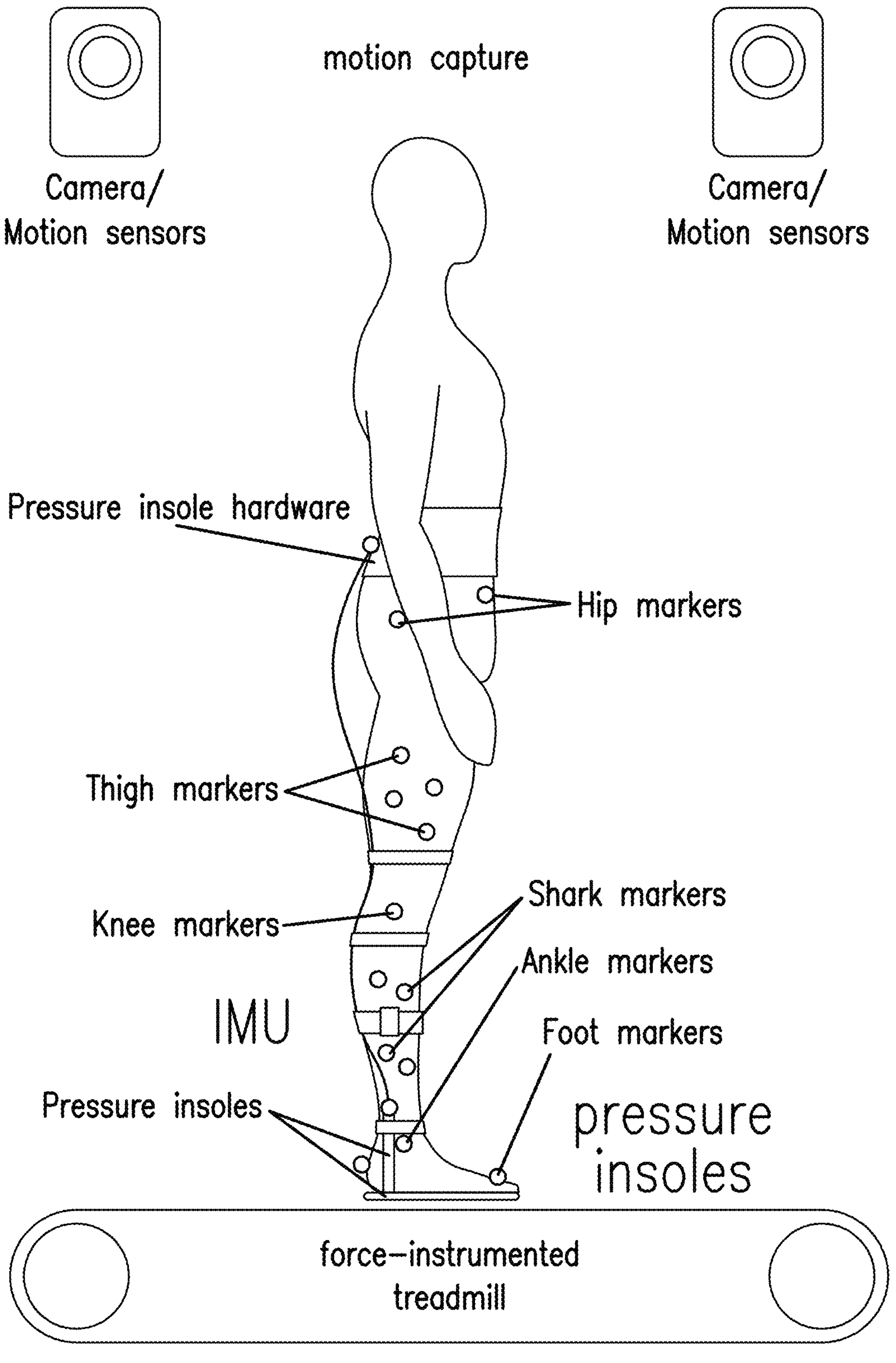
FIG. 4 shows an experimental setup schematic, with motion capture cameras and markers on the lower limbs, a force instrumented treadmill, pressure-sensing insoles in the shoes with associated data collection hardware/electronics on the abdomen, and an inertial measurement unit on the shank according to embodiments of the invention.

In one embodiment, the processing unit is further configured to estimate musculoskeletal loading using reference data that is either stored on data storage means in communication with the processing unit or reference data that has been collected or inputted from the specific user and used to calibrate or establish the processing algorithm. In one embodiment, the reference data are obtained by lab-based sensors, as shown in FIG. 4. The data storage means includes a database, a cloud storage system, and/or a computer readable memory.

In one embodiment, the processing unit is further configured to alert the user when the musculoskeletal loading is greater than a threshold that has been predefined or a threshold that has been calibrated for the specific user.

In one embodiment, the processing unit is further configured to advise the user on when and how to adjust their movement, actions or physical activity type and duration so as to reduce injury risks.

In one embodiment, the processing unit is further configured to communicate to a computer, a smartphone, a smartwatch, a tablet or other user feedback or data acquisition device for outputting at least one of the following: estimated musculoskeletal loading, alert and advice, estimates of microdamage or microdamage accumulation, and/or probability of fracture, and storing the estimated musculoskeletal loading, alert and advice, estimates of microdamage or microdamage accumulation, and/or probability of fracture, and inputting user inputs.

In one embodiment, the wearable device further includes a biofeedback unit in communication with the processing unit for outputting or displaying at least one of the estimated musculoskeletal loading, alert and advice, estimates of microdamage or microdamage accumulation, and/or probability of fracture using audible, visual, tactile, haptic, thermal, electrical or other biofeedback means, and storing the estimated musculoskeletal loading, alert and advice, estimates of damage accumulation, and/or probability of fracture.

In one embodiment, the biofeedback unit includes a user interface device for user inputs. In one embodiment, the user inputs include height, weight, body mass index, age, gender, diet, training schedule, subjective pain/fatigue, bone cross-sectional area, bone geometry, bone density, bone composition, GPS position, altitude of the user and/or other personal health or demographic data.

Figure 2A:
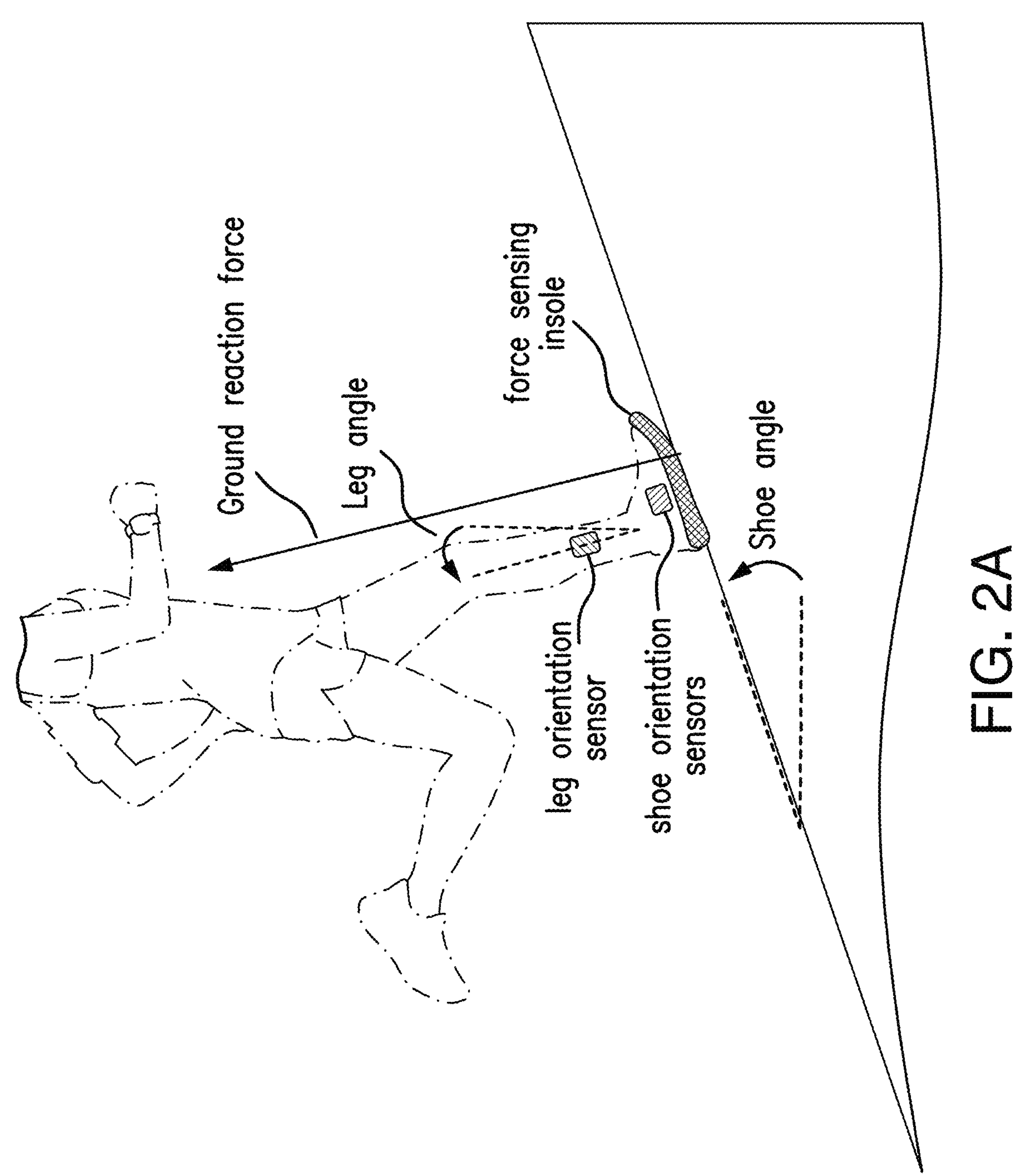
FIGS. 2A-2B show respectively sensor overview and algorithm flow chart of how one iteration of the wearable device fuses data from a pressure-sensing insole (comprised of a plurality of force sensors distributed under the foot) and two IMUs (data are processed to estimate leg and shoe orientation), in order to estimate bone loading, according to embodiments of the invention.
Figure 2B:
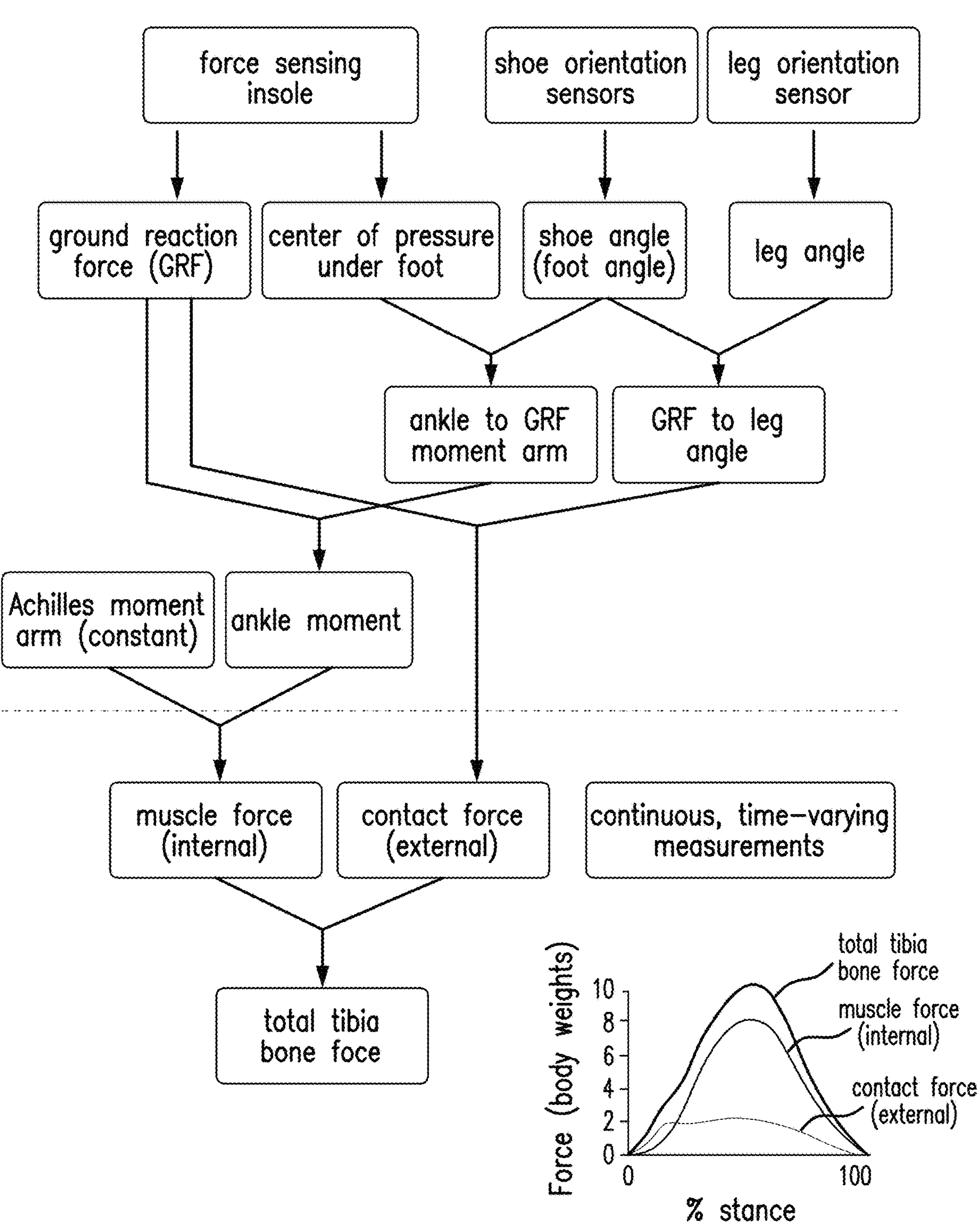

FIGS. 1, 2A, and 2B shows basic schematic of a wearable device set of sensors according to embodiments of the invention. FIGS. 1, 2A, and 2B shows sample sensors and device components of the wearable device, which includes, but are not limited to, a processor, pressure sensors, EMG sensors, strain gages, accelerometers, gyroscope, rechargeable battery, and wireless chip.

One exemplary application of the wearable device is to monitor tibia bone loading. FIGS. 22A-22M, 23A-23B and 24A-24B show lab tibia forces and estimated tibia forces and their corrections processed using linear regression, simplified inverse dynamic approach and machine learning, respectively, under different conditions The unique component of the approach/algorithm is the characterization of both external (ground reaction) and internal (muscle) forces that compress the tibia, a paradigm shift from previous wearable tech methods that use indirect (and incomplete) measures such as monitoring peak ground reaction force or leg acceleration as surrogates for tibia stress fracture risk. While previous researchers have computed external and internal tibia forces using lab-based equipment, routine screening in a lab is expensive, impractical and not representative of day-to-day loading. According to the invention, tibia bone loading can be effectively monitored with wearable sensors outside the lab, alerts can be provided in a risk of injure, thereby effectively reducing tibia stress fracture risk, reducing pain and healthcare costs, reducing missed work or recreation, and enhancing workplace or training productivity.

There are many applications of this wearable technology and sensor fusion approach beyond monitoring tibia stress fractures. A similar approach could be applied to monitor any type of musculoskeletal loading, particularly other bones, muscles, and tendons that are at heightened risk for overuse injury. For example, a wearable device could quantify the loading of back muscles and spinal discs to monitor lower back pain. In addition to load/force measurements, biomechanical metrics such as strain, power, and metabolic cost could be estimated.

In another aspect of the invention, the wearable device operably worn by a user for monitoring neuromuscular, physiological, biomechanical and/or musculoskeletal activity of a body structure of the user includes a plurality of sensors, each sensor operably worn by the user at a predetermined location and configured to detect information about neuromuscular, physiological, biomechanical and/or musculoskeletal activity thereon; and a processing unit in communication with the plurality of sensors and configured to process the detected information by the plurality of sensors to estimate bio-information of the body structure, and communicate the estimated bio-information to the user and/or a party of interest.

In one embodiment, the body structure of the user is a tibia bone, a calcaneus bone, a lumbar spine, or other bone, muscle, tendon, joint or musculoskeletal structure inside the body.

In one embodiment, the bio-information of the body structure includes musculoskeletal loading, or musculoskeletal structure stress or strain.

In one embodiment, the bio-information further includes data acquired from additional sensors that monitor sleep patterns, rest time between physical activity or other markers of tissue rest or remodeling.

In one embodiment, the plurality of sensors includes one or more motion/orientation sensors, and one or more force/muscle sensors. In one embodiment, the plurality of sensors further includes one or more EMG electrodes.

In one embodiment, the one or more motion/orientation sensors include IMUs, flex sensors, goniometers, or a combination thereof, and wherein the one or more force/muscle sensors include pressure or force sensors, pressure-sensing fabrics, strain gages, muscle sensors, or a combination thereof.

In one embodiment, the detected information by the plurality of sensors is processed by regression and sensor fusion algorithms, inverse dynamics algorithms, or machine learning algorithms.

In one embodiment, the processing unit is further configured to compute musculoskeletal loading using reference data stored on data storage means in communication with the processing unit or reference data that has been used to calibrate or establish the processing algorithm, so as to determine a condition of the body structure based on the computed loading, the condition including a normal condition or a graduated risk of injury.

In one embodiment, the reference data are obtained by motion analysis lab-based sensors, and the data storage means includes a database, a cloud storage system, and/or a computer readable memory.

In one embodiment, the processing unit is further configured to communicate to a computer, a smartphone, a smartwatch, a tablet, or other user feedback or data acquisition device for outputting the condition of the body structure, and/or alert and advice when the body structure is in the elevated risk of injury using audible, visual, tactile, haptic, thermal, electrical or other biofeedback means, storing the condition of the body structure, and/or alert and advice, and inputting user inputs.

In one embodiment, the wearable device further includes a biofeedback unit in communication with the processing unit for outputting and/or displaying the condition of the body structure, and/or alert and advice when the body structure is in the graduated risk of injury using audible, visual, tactile, haptic, thermal, electrical or other biofeedback means, and storing the condition of the body structure, and/or alert and advice when the body structure is in the graduated risk of injury.

In one embodiment, the biofeedback unit includes a user interface device for user inputs. In one embodiment, the user inputs include height, weight, body mass index, age, gender, diet, training schedule, subjective pain/fatigue, bone cross-sectional area, bone density, bone composition, GPS position, altitude of the user and/or other personal health or demographic data.

In yet another aspect of the invention. The method for monitoring neuromuscular, physiological, biomechanical and/or musculoskeletal activity of a body structure of the user using a wearable device including a plurality of sensors includes receiving information about neuromuscular, physiological, biomechanical and/or musculoskeletal activity from the plurality of sensors; estimating bio-information of the body structure based on the received information from the plurality of sensors; and communicating the estimated bio-information to the user and/or a party of interest.

According to the invention, each sensor worn by the user at a predetermined location. In one embodiment, these predetermined locations may be unilateral across one leg/foot only or bilateral across a pair of legs/feet. In another embodiment, these predetermined locations may be a low back, or any desired parts of the user.

In one embodiment, the bio-information of the body structure includes musculoskeletal loading, or musculoskeletal structure stress or strain.

In one embodiment, the bio-information further includes data acquired from additional sensors that monitor sleep patterns, rest time between physical activity or other markers of tissue rest or remodeling. In one embodiment, the estimating step is performed by regression and sensor fusion algorithms, inverse dynamics algorithms, or machine learning algorithms.

We have envisioned multiple categories of algorithms. Inverse dynamics based algorithms are being developed that use wearable sensors as surrogates for motion and force data that we commonly collected in the lab. In other words, we map sensor data on the musculoskeletal model, and use laws of physics to estimate bone loading. This approach is summarized in more detail below. Statistical regression analyses (linear and non-linear) are being employed to identify how to use portable sensor data to approximate lab-based estimates of tibia force. Currently, initial algorithms have been developed for predicting tibia bone loading across various running conditions. Algorithms are general in structure, but may be calibrated to individuals (i.e., some level of individualization/normalization enables us to apply a single algorithm to many subjects.) The algorithm outputs metrics related to bone load, such as but not limited to: peak bone loading per stride, impulse (time integral, i.e., area under bone force curve) per stride, per mile or per day, and duty cycle (i.e., frequency) of loading, etc.

FIG. 2B shows algorithm flow chart of how the wearable device fuses data from a pressure-sensing insole (comprised of a plurality of force sensors distributed under the foot) and two IMUs (data are processed to estimate leg and shoe orientation), in order to estimate bone loading, according to embodiments of the invention.

In one embodiment, the estimating step computes bio-information using reference data to calibrate or establish the processing algorithm, so as to determine a condition of the body structure based on the estimated musculoskeletal loading, the condition including a normal condition or a graduated risk of injury.

In one embodiment, the reference data are obtained by motion analysis lab-based sensors.

In one embodiment, the communicating step includes for outputting or displaying the condition of the body structure, and/or alert and advice when the body structure is in the elevated risk of injury or the injured condition using audible, visual, tactile, haptic, thermal, electrical or other biofeedback means, and storing the condition of the body structure, and/or alert and advice.

In one or more example embodiments, the method and algorithms and functions described may be implemented in hardware, software, or any combination thereof. If implemented in software, the method and algorithms and functions may be stored on or encoded as one or more instructions or code on a non-transitory computer-readable medium, such that, when the one or more instructions or code are executed by one or more processors, the execution of the one or more instructions or code causes the wearable device to perform a method for monitoring neuromuscular, physiological, biomechanical and/or musculoskeletal activity of a body structure of a user wearing the wearable device. The non-transitory computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

These and other aspects of the present invention are further described below. Without intent to limit the scope of the invention, examples and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Evaluating Wearable Sensor-Based Tibia Force Estimation Algorithm for Applications in Stress Fracture Reduction in Runners

Methods

A. Condition Selection

In order to assess the accuracy of wearable estimates of tibia force in different circumstances, tasks were selected to represent a range of bone loading typical in recreational running. Many conditions were tested in the experimental protocol, but for the purposes of this exemplary investigation, only tasks varying step frequency at a constant speed on level ground, and varying speeds on level ground, were analyzed.

Previous studies have found significant differences in various running mechanics metrics, including segment orientations, ground reaction force, acceleration, and leg stiffness, across different running step frequencies. Studies have shown that an increase in step frequency results in lower initial impact peaks and loading rates in ground reactions forces, lower peak ground reaction forces. More generally, increases in step frequency yield lower ground reaction forces throughout stance.

While previous studies tested various ranges of step frequencies, most found statistically significant differences in output metrics at 10-20% deviations from preferred step frequency. Pilot testing was conducted to determine the largest deviations from preferred step frequency that could be comfortably performed by subjects while running on the treadmill. Based on this pilot testing and results from previous studies, we decided to test step frequencies between −15% and +15% of preferred step frequency, which we expect to yield a range of tibia bone loading curves suitable for evaluating our wearable estimates.

For this exemplary study, we also record running trials at different speeds to assess wearable estimates over a wider range of conditions. Running speed has been shown to alter lower limb bone strain in goats, dogs, and horses, where an increase in speed results in an increase in strain on the tibia bone. It is expected to see an increase in tibia bone loading with an increase in speed in humans as well. Slow running speeds, between 2.2 and 3.0 m/s were chosen in order to accommodate subjects who were inexperienced runners.

B. Experimental Design

In this exemplary experiment, sensor placement and synchronization were extremely important in order to ensure both an accurate lab estimate of tibia loading and a corresponding set of portable sensor data for analysis. Since the goal of the experiment is to determine if wearable sensors are capable of calculating bone loading for most or all subjects, special care was taken to use similar sensor placement during each data collection. With so many measurement modalities being utilized at once, extra emphasis was also placed on designing a repeatable and robust experiment.

B.1. Data Collection Hardware

Prior to subject arrival, data collection software was prepared, sensors were cleaned, charged, and organized, and motion capture hardware was calibrated. All trials were performed on a fully-instrumented, split-belt treadmill (Bertec Corporation, Columbus, OH) capable of measuring forces, moments, and centers of pressures at 1000 Hz on each belt. A ten camera motion capture system (Vicon Motion Systems, UK) was used to record lower limb motion at 200 Hz during all trials.

B.2. Subject Preparation

Three healthy adult subjects (2 male, 1 female, height 1.8±0.1 m, weight 66.8±7.0 kg, age 24.6±1.5 years) participated in this study. Inclusion was determined based on physical fitness (ability to complete all trials) and shoe size (within the range of available insole sizes). Upon arrival, subjects were given an overview of the experimental protocol and goals, then gave informed consent to participate in the study (approved by the Vanderbilt University Internal Review Board). Subjects were instructed to wear tight-fitting shorts to facilitate motion capture marker placement. While on the treadmill, subjects wore an upper body safety harness which was secured via a belay system to the ceiling. Handrails were attached to the treadmill on either side of the subject and an emergency stop button was affixed to the railing for subject safety.

Given the high number of measurement modalities used on the lower limbs, care was taken to avoid overlapping or obstructing sensors. With this goal in mind, pressure sensing insoles were set up first, followed by the inertial measurement unit, and finally motion capture markers. A schematic of the experimental setup is shown in FIG. 4.

The Pedar-X pressure sensing insole system (Novel, Munich, Germany) was set up for collecting data under each foot. A belt carrying the portable electronics (main collection box, battery, synchronization unit) was strapped to the subject's abdomen and insoles were placed inside each of the subject's shoes. Insoles were connected via cables to the main collection box and straps were placed at the ankle, calf, and thigh to secure the cables to the subject's legs. Insoles were tared and then subjects tied the laces of their shoes as desired.

With the pressure sensing insoles set up, the 3-Space Data Logger inertial measurement unit (IMU) (Yost Labs, Portsmouth, Ohio) was placed on the right shank. The IMU was placed on the lateral part of the shank using Velcro and a fabric strap such that the IMU's y-axis was parallel to the knee axis and its z-axis was aligned with the shank. After placement, the sensor was tared while the subject stood in an upright, natural position.

Once all wearable sensors were in place, twenty-four reflective motion capture markers were placed on landmarks and segments of the subject's pelvis and right leg to record lower limb kinematics: six on the pelvis, four in a cluster on the thigh, two on the knee, four in a cluster on the shank, two on the ankle, and six on the foot. Markers were attached to the body using double sided tape, and additional tape was placed around the markers on the shoes and any particularly sweaty areas to prevent markers from moving or falling off during data collection.

B.3. Data Collection

Data collection for this study included four sets of conditions: calibration trials, decreasing step frequency trials, increasing step frequency trials, and speed sweep trials. All trials were performed on the treadmill at zero incline. The experiment began with one static and two functional calibrations, used to define motion capture marker placements and joint locations as well as obtain baseline force and orientation measurements. After this, the treadmill was turned on and set to a moderate walking speed to allow subjects to acclimate to the treadmill. Once comfortable, the treadmill was then set to a moderate running speed (2.4 m/s or 2.6 m/s), and subjects ran at their preferred step frequency. Once at steady state, experimenters counted the number of strides taken during a thirty second period and doubled this number to obtain subjects' preferred step frequency. Once this measurement was completed, the treadmill was stopped and subjects were allowed to rest.

Two running step frequency condition sweeps were performed, each comprised of four trials, beginning with the subject running at their natural step frequency, then increasing or decreasing the step frequency by five percent per trial. All trials were performed at a constant running speed of 2.4 m/s or 2.6 m/s, corresponding to the speed of the calibration trial. For each trial, a metronome was set and played over speakers to regulate step frequency, with one beat played for each desired foot strike. Subjects began standing on the treadmill at the beginning of each trial, stomped on the treadmill with the right foot, and were then brought to their running speed and instructed to match their foot strikes to the beat of the treadmill. Once synchronized with the metronome, twenty to thirty additional seconds were recorded before stopping the treadmill and resetting for the next trial.

Upon completion of the step frequency trials, speed sweep trials were conducted. Four trials were recorded for each subject, beginning at 2.2 m/s or 2.4 m/s and increasing by 0.2 m/s for each trial. All trials occurred with the treadmill set to zero incline, and no metronome was playing during speed sweep trials so subjects were free to self-select their step frequency for each trial. Trials were conducted one at a time in a similar fashion to the step frequency sweep: subjects began standing still on the treadmill, stomped before the treadmill was set to the desired speed, and once at the steady state speed, ran for twenty to thirty seconds in order to collect sufficient data to analyze before the treadmill was stopped and reset for the next trial.

In order to synchronize the various measurement modalities, several methods were employed. Motion capture, treadmill force, moment, and center of pressure data were collected using Vicon's Nexus software. Insole pressures were collected separately at 100 Hz through Novel's Database and Pedar data collection software. Using Novel's synchronization system, an analog signal was recorded in Nexus and used to trigger the start of data collection for each trial whenever the experimenter began a trial in the Pedar software. Trials were stopped manually in Nexus and Pedar upon completion of the twenty to thirty second steady state segment of running but prior to stopping the treadmill. Euler angles calculated by the IMU utilizing a Kalman filter were collected separately at approximately 60 Hz and stored locally to the IMU device. Experimenters pressed the record button on the IMU at the beginning of each trial and the stop button upon completion of each trial once the treadmill reached a stop. This data was synchronized and trimmed to match other data by aligning the peaks corresponding to the stomp at the beginning of each trial. For analysis purposes, twenty second segments at the end of each trial were isolated for analysis.

C. Data Processing

Using the static calibration trial for each subject as a model, motion capture marker labeling and gap filling was performed in Vicon's Nexus software, and exported into Visual3D (C-Motion, Germantown, MD) for model-based calculations and data exporting. The functional calibration trial was used to define functional joints which enabled the calculation of joint-based kinematic and kinetic metrics. Motion capture data was filtered using a fourth order Butterworth filter with a cutoff frequency of 6 Hz and treadmill data was filtered with a cutoff frequency of 15 Hz. Complete ground reaction forces, shank angles, and ankle moments were exported into Matlab for further calculations. Pedar data files containing force and center of pressure measurements, and Yost data files containing Euler angles were imported and saved in a Matlab® data file in a structure containing all other data from the study. Using a custom Matlab® script, data was aligned using the peak in force from the stomp at the beginning of each trial, and all sources of data were trimmed to twenty seconds. Once trimmed, data was parsed to identify heel strike and toe off events, separate data intro strides, and average over the number of strides in the twenty seconds of data. The result of this processing is a single vector of one thousand data points for each metric corresponding to the stance phase of one gait cycle.

D. Data Analysis

As described in Introduction, tibia force can be approximated as the sum of external and internal forces. Estimation methods for each force differed between lab and wearable techniques, but the same general principle of summing forces, as described in Equation 1, applies for each. All calculations described below were done using a custom Matlab® script, and data for each trial was saved into subject-specific structures.

$$F_{tib} = \sum F = F_{ext} + F_{\text{int}} \tag{1}$$

D.1. Laboratory Estimates of Tibia Force

Using Equations 2 and 3, and the outputs from Visual3D, lab-based external (ground reaction force) and internal (muscle) contributions to tibia force were estimated. External force was estimated as the ground reaction force vector projected onto the long axis of the tibia (Equation 2). The tibia axis was estimated as a vector from the computed ankle joint center to the knee joint center. Internal force was estimated as the ankle moment divided by the moment arm of the Achilles tendon, assumed to be a constant value of 5 cm (Equation 3). Because the force contributions of dorsiflexor muscles was ignored, any period of negative ankle moment following heel strike was set to zero.

$$F_{ext,lab} = |\overrightarrow{GRF}| * \cos\theta_{tib-GRF} \quad (2)$$

$$F_{int,lab} = \frac{M_{ankle}}{|r_{AT}|} = \frac{\overrightarrow{r_{COP-ankle}} \times \overrightarrow{GRF}}{|r_{AT}|} \quad (3)$$

D.2. Wearable Estimates of Tibia Force

Using Equations 4 and 5 (modifications of Equations 2 and 3) and the data from the pressure sensing insoles and inertial measurement unit, wearable sensor-based external (ground reaction force) and internal (muscle) contributions to tibia force were estimated. External force was estimated as the vertical ground reaction force as measured by the insoles projected onto the axis of the tibia in the sagittal plane, using the shank angle from the IMU (Equation 4). Internal force was estimated as the product of insole-based center of pressure to ankle moment arm (measured center of pressure minus an assumed constant distance from the heel to the tibia/ankle of 5 cm) divided by the moment arm of the Achilles tendon, assumed to be a constant value of 5 cm (Equation 5).

$$F_{ext,wear} = GRF_{vertical} * \cos\theta_{shank} \quad (4)$$

$$F_{int,wear} = \frac{(|\overrightarrow{r_{COP,insole}}| - |r_{heel-tib}|) * GRF_{vertical}}{|r_{AT}|} \quad (5)$$

D.3. Peak Tibia Force and Tibia Load per Kilometer

Once waveforms of tibia force were generated for each trial, two other metrics were calculated. First, peak tibia force was determined, as described in Equation 6, as the maximum value of tibia force for each trial. Peak force was determined for both lab and wearable data sets.

$$F_{tib,peak} = \max(F_{tib}) \quad (6)$$

Tibia load per kilometer was calculated as a metric that may give insight into loading of the tibia over time. Tibia load per kilometer was calculated as tibia load per step multiplied by the rate of steps per kilometer for each trial (Equation 7). Tibia load per step is defined as the impulse, or area under the tibia force-time curve during stance, and rate of steps per kilometer for each trial was defined as the reciprocal of the product of stride time and treadmill velocity. Load per kilometer was determined using lab and wearable tibia force data, but stride time and velocity were determined from the treadmill for all cases. Stance time was the time from heel strike on one food to toe off on the same foot. Stride time was the time from heel strike on one foot to the following heel strike on the same foot.

$$J_{tib\ per\ km} = J_{tib\ per\ step} * \frac{\text{steps}}{\text{km}} = \frac{\int_0^{t_{stance}} (F_{tib} * dt)}{t_{stride} * v_{treadmill}} \quad (7)$$

D.4. Calibration of Wearable Estimates

Due to inherent error in wearable sensor data and the use of modified equations, we do not expect perfect estimates of tibia load. In order to correct for these inaccuracies, we determine the linear trendline that minimizes error between lab and wearable estimates of tibia force over stance. This trendline accounts for a scaling factor and constant offset between lab and wearable estimates. Using the trendline equation, wearable sensor data are recalculated as the raw estimate times the scaling factor and plus the constant offset. This new, calibrated wearable estimate of bone loading is used to compute error between lab and wearable estimates. Rather than focusing on the absolute value of tibia force estimates, this approach allows us to evaluate whether trends in lab estimates of tibia bone load are also estimated in wearable estimates. Calibrations is determined for individual trials, single subjects, and all subjects.

D.5. Calculation of Error

For all metrics, root mean square error (RMSE) was found between lab and raw wearable estimates, as well as between lab and calibrated wearable estimates. RMSE is reported in body weights for force over stance and peak force, and in body weights times seconds for load per kilometer. RMSE is also given as a percentage of maximum for each metric, where the maximum is defined to be the maximum force (for force over stance and peak force) or load per kilometer recorded within the set of data analyzed (i.e., a single condition for trial by trial analysis, all conditions for a single trial for subject by subject analysis, or all trials for overall analysis).

Results

A. Laboratory Estimates of Tibia Force

Utilizing lab measurements, tibia loads were estimated using the inverse dynamics approach, and analysis of differences between conditions was performed. As discussed, external (i.e. projected ground reaction) and internal (i.e. muscles and tendons) forces contribute to total tibia force. In this study, it was found that external forces produce a force on the tibia equivalent to 1.5 to 2.4 body weights, whereas internal forces produce a force on the tibia of 3.2 to 6.2 body weights, resulting in a total tibia loading of 4.4 to 8.1 body weights in the conditions tested. During early stance, external forces comprise most of the total tibia force, but in mid to late stance, the contributions of internal forces are up to 3.8 times the contributions of external forces.

B. Condition Comparisons

Between conditions, differences in magnitudes and timing of tibia loading were observed. Summaries of differences in step frequency, stance times, and peak tibia loads calculated from lab measurements are included in Tables 1-3. In the tables, step frequency (SF) sweep trials are labeled by percent deviation from preferred step frequency and were all completed at 2.4 m/s for subject 1 and 2.6 m/s for subjects 2 and 3, while speed (SP) sweep trials are labeled by treadmill speed in meters per second. Step frequencies are given in steps per minute, stance time is given in seconds, and peak tibia load is given in body weights. In all but one case, increasing step frequency resulted in a decreased stance time for all subjects. In general, peak tibia forces increased with positive deviations from preferred step frequency, while differences in peak tibia forces for negative deviations from preferred step frequency varied between subjects. For the speed sweeps, step frequencies and peak tibia forces tended to increase with increasing speed, while stance time tended to decrease with increasing speed.

TABLE 1

Summary of differences in in step frequency, stance time, strides per kilometer, and peak tibia force across all trials performed by Subject 1.

| | SF −15 | SF −10 | SF −5 | SF +0 | SF +5 | SF +10 | SF +15 | SP 2.2 | SP 2.4 | SP 2.6 | SP 2.8 |
|---|---|---|---|---|---|---|---|---|---|---|---|
| Prescribed Step Freq. | 72 | 76 | 80 | 84 | 88 | 92 | 96 | | | | |
| Actual Step Freq. | 72.8 | 75.9 | 80.4 | 84.3 | 88.8 | 92.6 | 96.6 | 78.1 | 81.7 | 84.2 | 83.9 |
| Stance Time | 0.39 | 0.40 | 0.36 | 0.36 | 0.35 | 0.35 | 0.33 | 0.40 | 0.37 | 0.35 | 0.34 |
| Strides Per Kilometer | 505 | 527 | 559 | 585 | 616 | 643 | 670 | 592 | 567 | 540 | 500 |
| Peak Tibia Force (Lab) | 5.99 | 5.82 | 5.91 | 5.44 | 5.22 | 4.78 | 4.35 | 5.26 | 5.38 | 5.53 | 5.56 |

TABLE 2

Summary of differences in in step frequency, stance time, strides per kilometer, and peak tibia force across all trials performed by Subject 2.

| | SF −15 | SF −10 | SF −5 | SF +0 | SF +5 | SF +10 | SF +15 | SP 2.4 | SP 2.6 | SP 2.8 | SP 3.0 |
|---|---|---|---|---|---|---|---|---|---|---|---|
| Prescribed Step Freq. | 72 | 76 | 80 | 84 | 88 | 92 | 96 | | | | |
| Actual Step Freq. | 72.6 | 75.5 | 80.3 | 83.9 | 88.1 | 92.3 | 96.3 | 83.0 | 83.0 | 83.8 | 86.2 |
| Stance Time | 0.35 | 0.34 | 0.32 | 0.30 | 0.28 | 0.26 | 0.25 | 0.30 | 0.30 | 0.30 | 0.29 |
| Strides Per Kilometer | 466 | 484 | 515 | 538 | 565 | 592 | 617 | 576 | 532 | 499 | 479 |
| Peak Tibia Force (Lab) | 7.40 | 7.59 | 7.57 | 7.57 | 7.47 | 7.26 | 7.07 | 7.35 | 7.73 | 7.88 | 8.06 |

TABLE 3

Summary of differences in in step frequency, stance time, strides per kilometer, and peak tibia force across all trials performed by Subject 3.

| | SF −15 | SF −10 | SF −5 | SF +0 | SF +5 | SF +10 | SF +15 | SP 2.4 | SP 2.6 | SP 2.8 | SP 3.0 |
|---|---|---|---|---|---|---|---|---|---|---|---|
| Prescribed Step Freq. | 72 | 76 | 80 | 84 | 88 | 92 | 96 | | | | |
| Actual Step Freq. | 71.8 | 75.5 | 80.1 | 84.1 | 88.4 | 92.8 | 97.0 | 81.5 | 82.4 | 83.5 | 83.8 |
| Stance Time | 0.34 | 0.34 | 0.32 | 0.30 | 0.28 | 0.26 | 0.25 | 0.31 | 0.31 | 0.30 | 0.30 |
| Strides Per Kilometer | 460 | 484 | 514 | 539 | 567 | 595 | 566 | 528 | 497 | 465 | 465 |
| Peak Tibia Force (Lab) | 7.59 | 7.74 | 7.79 | 7.88 | 7.23 | 7.00 | 7.06 | 7.32 | 7.67 | 7.66 | 7.68 |

C. Wearable Estimates of Tibia Force

Upon completion of lab-based calculations, wearable sensor data was analyzed to assess accuracy of individual measurements as well as overall estimates of tibia forces. In general, the shank angle estimated obtained from the Euler angles of the IMUs were within the correct range of values but did not follow the same curve as the shank angle obtained from motion capture data. Ground reaction force moment arm obtained from insole center of pressure measurements and used to calculate internal contributions to tibia force tended to match measurements from the force instrumented treadmill during early and mid-stance but were overestimated in late stance. Ground reaction forces measured by the insoles tended to follow the same trajectory as measured ground reaction forces from the treadmill but were slightly delayed in timing during stance and were generally underestimated throughout the stance phase of gait.

C.1. Raw Estimates

Figure 5:
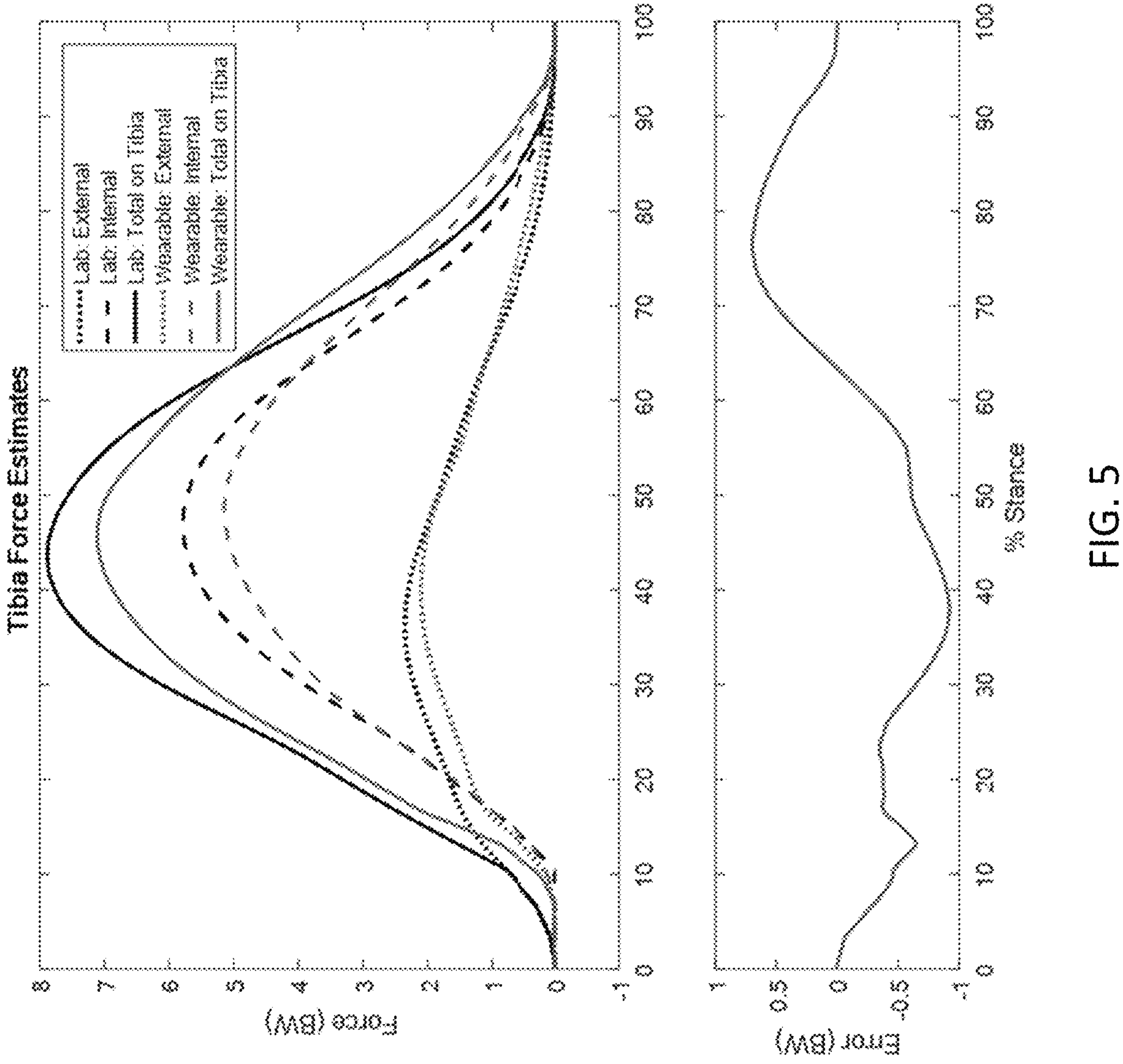
FIG. 5 shows comparison of lab and wearable estimates of tibia force according to embodiments of the invention. Top: estimates of internal, external, and total tibia forces from both lab-based sensors and wearable sensors. Bottom: Error between lab and wearable estimates of total tibia force.

Wearable sensor data was used in place of lab data to estimate internal and external contributions to tibia force, and to estimate total tibia force experienced during stance. A representative plot of the differences between lab estimates and wearable estimates can be seen in FIG. 5. The upper portion of FIG. 5 shows the internal, external, and total tibia forces estimated from lab-based measurements in black, and from wearable measurements in pink. In most cases, the wearable estimate displays an underestimate of external forces during early stance and an overestimate of internal and external forces during late stance. During early and mid-stance, the magnitude of total tibia force is lower for the wearable estimate, due to an underestimate of both internal and external forces. The lower portion of FIG. 5 shows the error in the total tibia force estimate across the stance phase of gait. For most trials, the magnitude of error between total wearable and lab estimates of tibia force was less than one body weight throughout stance.

As a preliminary analysis to determine the accuracy of the raw wearable estimate of tibia force, the root mean square error between lab and wearable estimates of bone loading throughout the stance phase was calculated for each subject and for all data combined. Subject 1 a root mean square error of 0.70 body weights (11.7% of max). Subject 2 had a root mean square error of 0.82 body weights (10.2% of max). Subject 3 had the lowest root mean square error of 0.46 body weights (5.8% of max). The root mean square error for all subjects was 0.68 body weights (8.4% of max).

C.2. Calibrated Estimates

Figure 6:
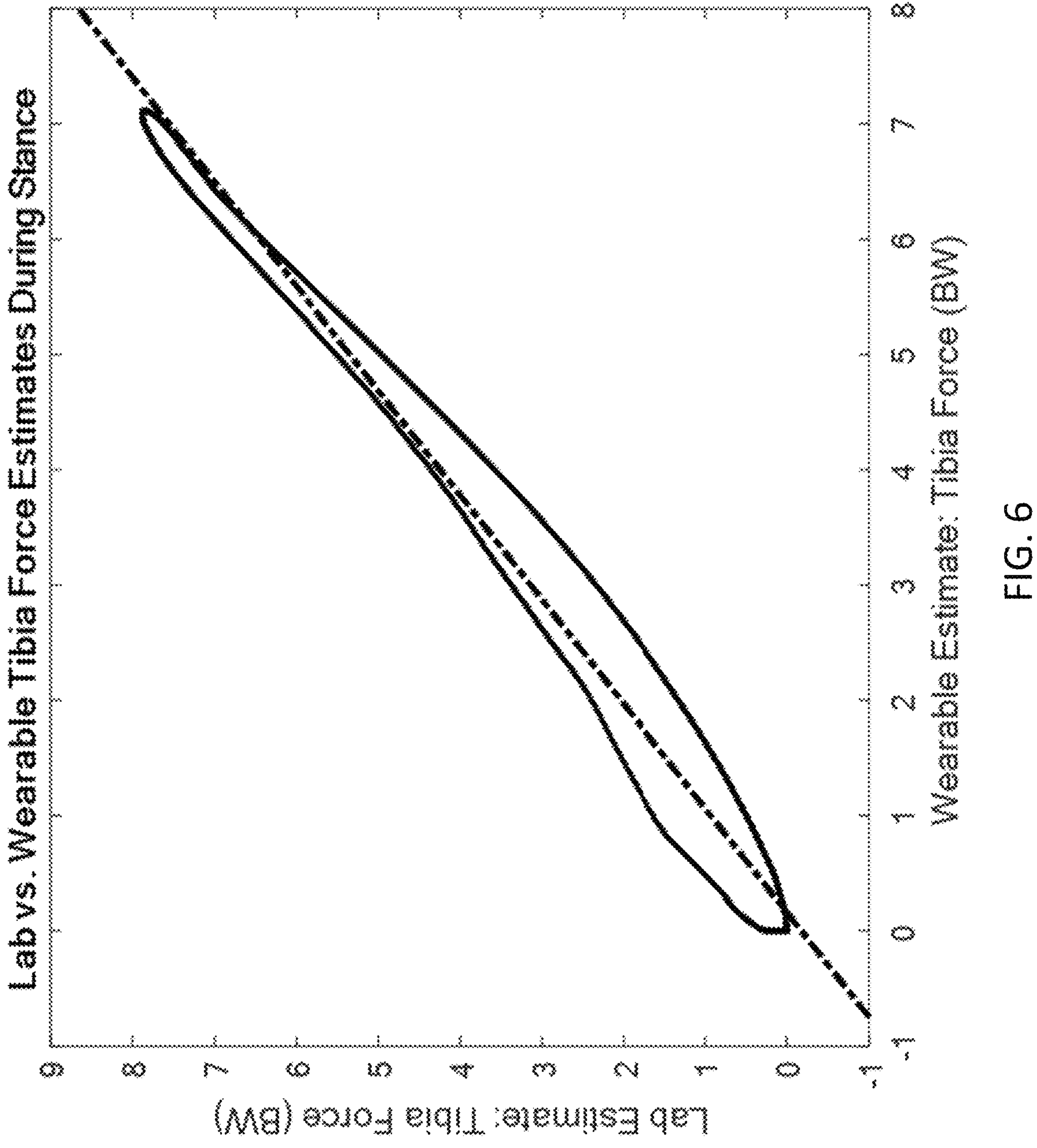
FIG. 6 shows a sample plot of lab estimate of tibia force versus wearable estimate of tibia force during stance with a linear trendline fitted to the data according to embodiments of the invention.
Figure 7:
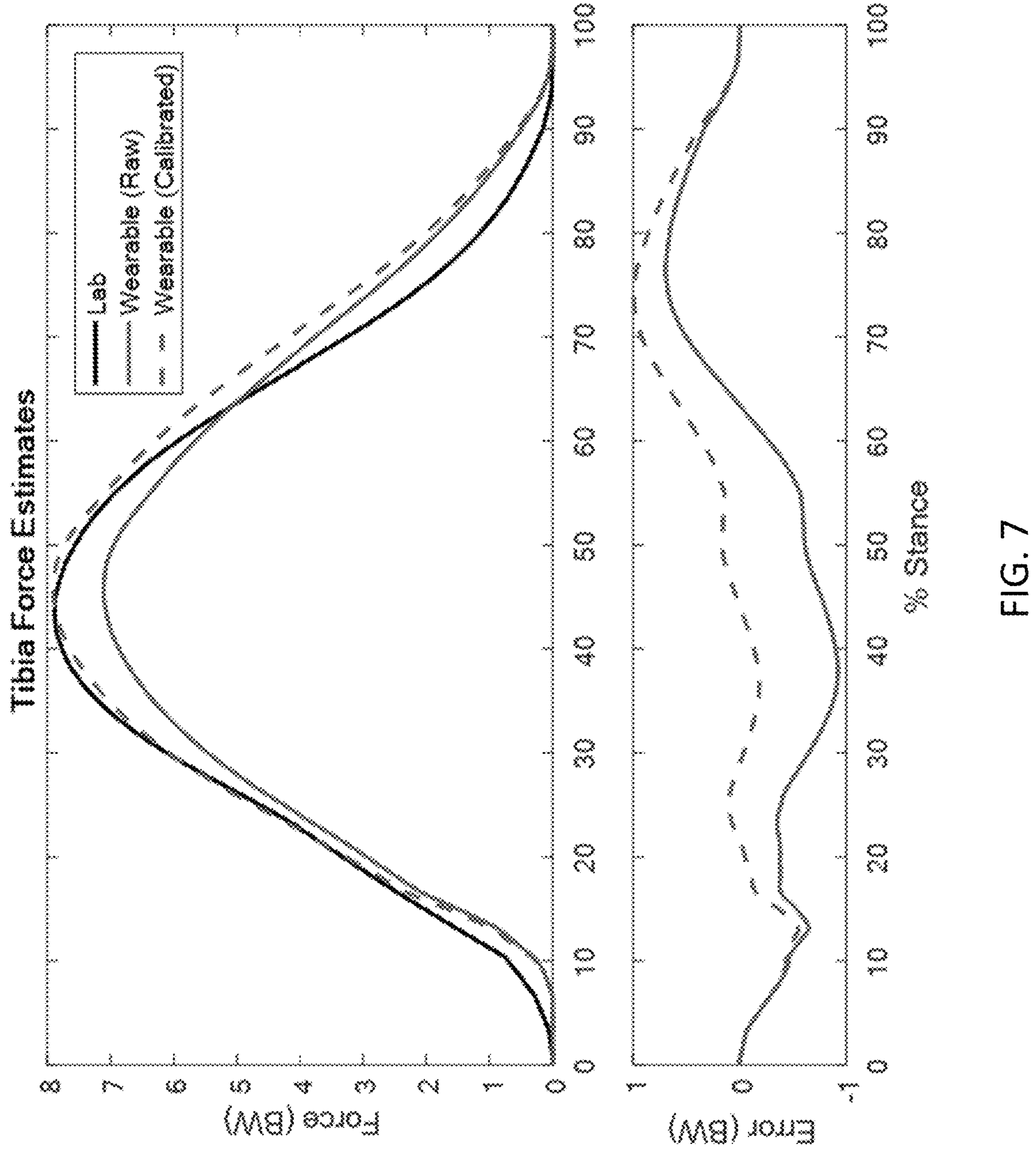
FIG. 7 shows comparison of lab, unscaled wearable, and scaled/calibrated wearable estimates of tibia force according to embodiments of the invention. Top: estimates of total tibia forces. Bottom: Error between lab and unscaled wearable (solid) and lab and scaled/calibrated wearable (dashed) estimates of total tibia force.

To compare the estimates of total tibia force during stance generated from lab data and wearable data, plots of wearable estimates versus lab estimates were generated for all trials. A linear trendline was fitted to the data for each trial, as well as for all data for each subject, and all data from the study. An example plot is shown below in FIG. 6, where the solid line is the data for one representative trial and the dash-dotted line is the best fit line for that single trial. The wearable versus lab estimate curve starts at zero and progresses clockwise on the plot. The best fit line accounts for an arbitrary offset and scaling factor between the two sets of data, and this type of correction could easily be implemented into the processing of data in a wearable device. A plot showing the resulting tibia force curve compared to the raw wearable estimate and the lab estimate of tibia force for a representative trial can be found in FIG. 7.

From each best fit line, root mean square error of the calibrated estimates was determined for all individual trials, all trials for each subject, and the entire data set. Summaries of these values are included in Tables 4-6. For all trials, root mean square error was less than one body weight, in most cases, well below half a body weight. Subject 1 had the best fit lines with errors less than one quarter body weight (2 to 5% of max). Subject 2 had the greatest errors of between 0.38 to 0.83 body weights (5 to 11% of max). Subject 3 had errors between 0.25 to 0.41 body weights (3 to 6% of max).

TABLE 4

Root mean square error in trial-specific linear trendline for wearable estimates of tibia force across the entire stance phase of gait for each trial performed by Subject 1.

| | SF −15 | SF −10 | SF −5 | SF +0 | SF +5 | SF +10 | SF +15 | SP 2.4 | SP 2.6 | SP 2.8 | SP 3.0 |
|---|---|---|---|---|---|---|---|---|---|---|---|
| RMSE (BW) | 0.17 | 0.15 | 0.12 | 0.12 | 0.14 | 0.20 | 0.14 | 0.11 | 0.12 | 0.16 | 0.25 |
| RMSE (% Max) | 2.84 | 2.52 | 2.03 | 2.12 | 2.62 | 4.14 | 3.31 | 2.16 | 2.27 | 2.96 | 4.43 |

TABLE 5

Root mean square error in trial-specific linear trendline for wearable estimates of tibia force across the entire stance phase of gait for each trial performed by Subject 2.

| | SF −15 | SF −10 | SF −5 | SF +0 | SF +5 | SF +10 | SF +15 | SP 2.4 | SP 2.6 | SP 2.8 | SP 3.0 |
|---|---|---|---|---|---|---|---|---|---|---|---|
| RMSE (BW) | 0.38 | 0.46 | 0.52 | 0.83 | 0.61 | 0.75 | 0.71 | 0.47 | 0.46 | 0.48 | 0.48 |
| RMSE (% Max) | 5.15 | 6.06 | 6.81 | 10.90 | 8.14 | 10.33 | 10.07 | 6.43 | 5.94 | 6.08 | 5.90 |

TABLE 6

Root mean square error in trial-specific linear trendline for wearable estimates of tibia force across the entire stance phase of gait for each trial performed by Subject 3.

| | SF −15 | SF −10 | SF −5 | SF +0 | SF +5 | SF +10 | SF +15 | SP 2.4 | SP 2.6 | SP 2.8 | SP 3.0 |
|---|---|---|---|---|---|---|---|---|---|---|---|
| RMSE (BW) | 0.39 | 0.32 | 0.39 | 0.41 | 0.26 | 0.37 | | 0.34 | 0.25 | 0.38 | 0.27 |
| RMSE (% Max) | 5.18 | 4.10 | 5.02 | 5.23 | 3.55 | 5.23 | | 4.75 | 3.36 | 4.89 | 3.51 |

Figure 8:
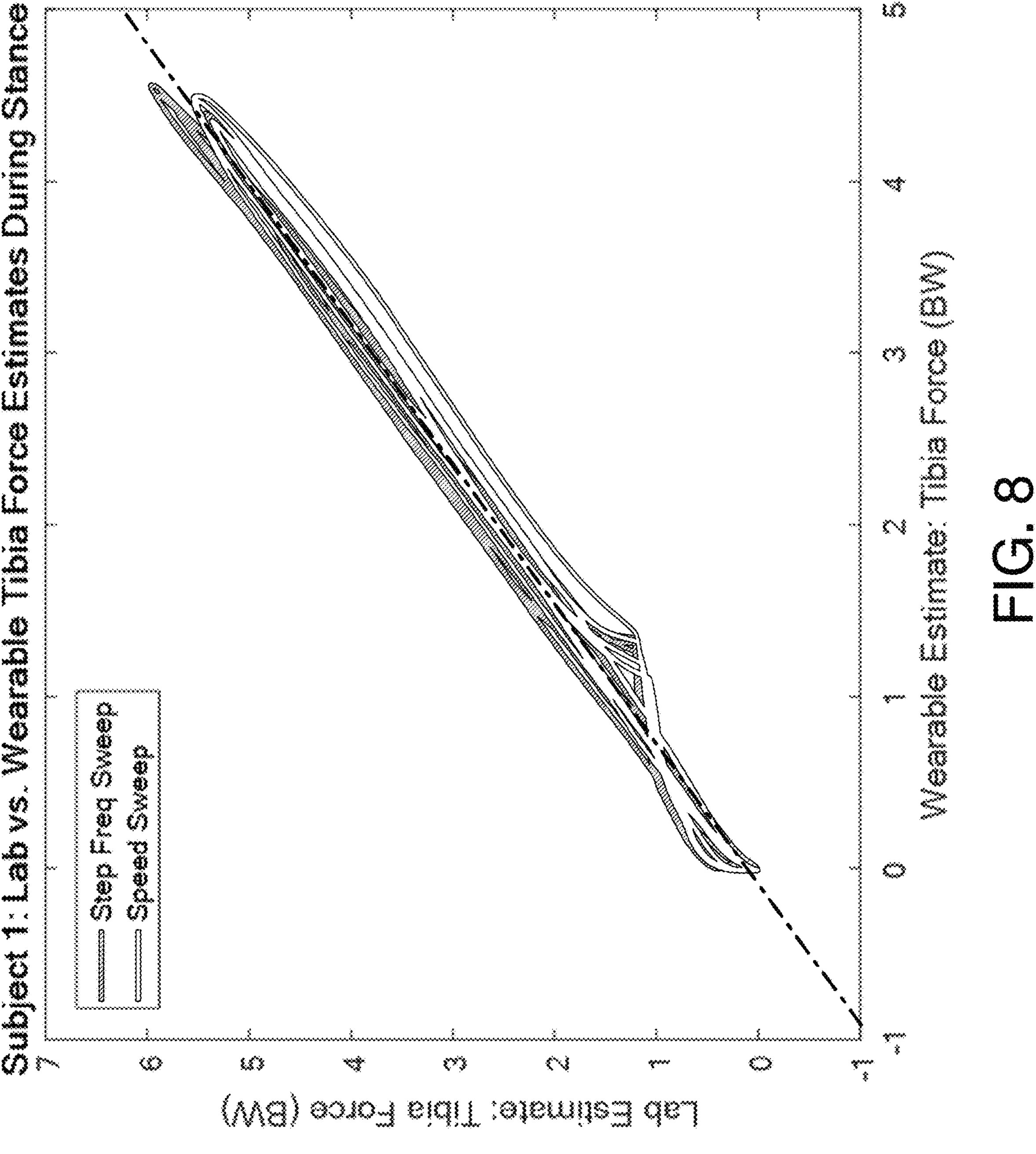
FIG. 8 shows lab estimates of tibia force versus wearable estimates of tibia force during stance for all trials completed by Subject 1 with a linear trendline fitted to the data according to embodiments of the invention.
Figure 9:
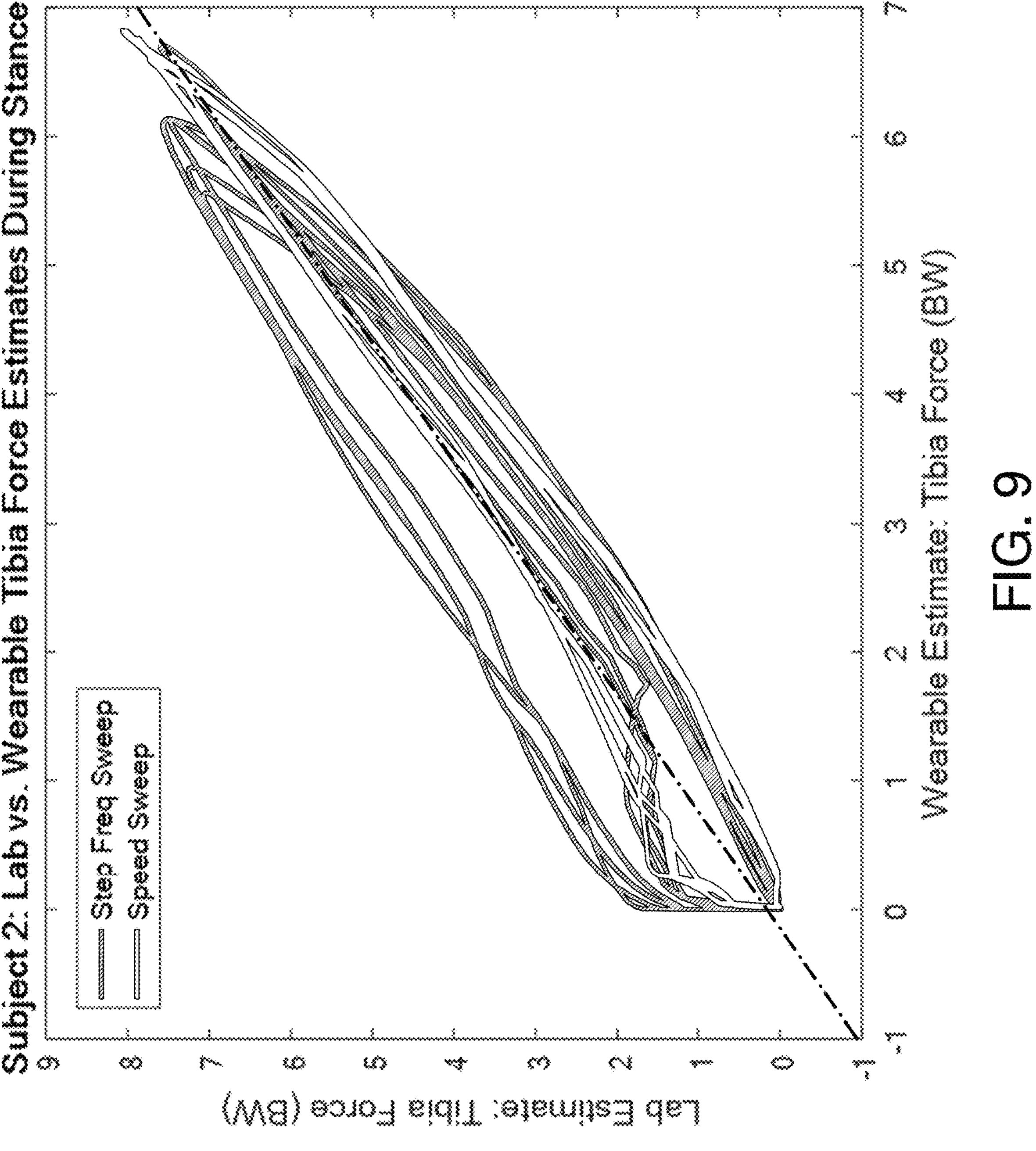
FIG. 9 shows lab estimates of tibia force versus wearable estimates of tibia force during stance for all trials completed by Subject 2 with a linear trendline fitted to the data according to embodiments of the invention.
Figure 10:
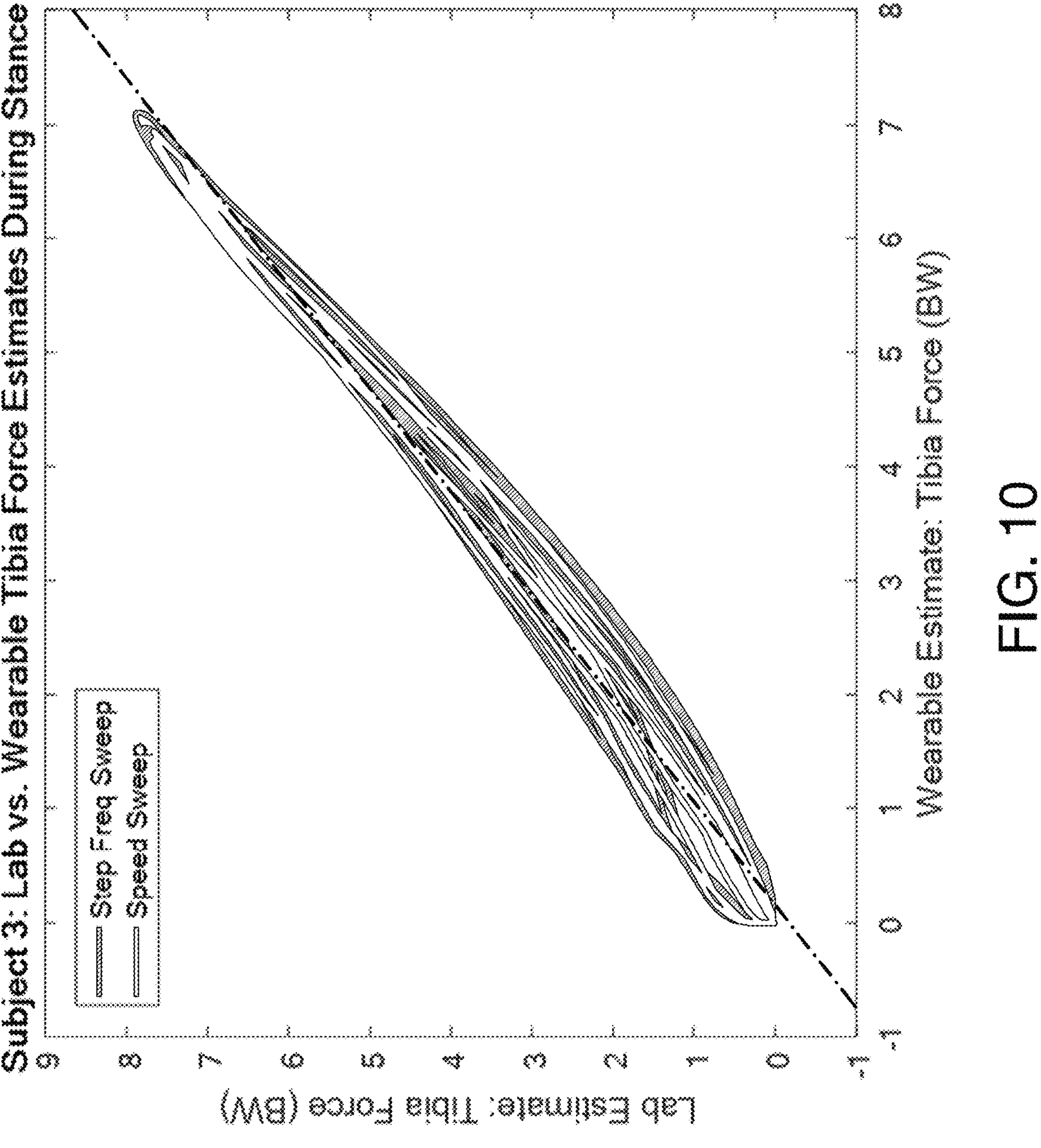
FIG. 10 shows lab estimates of tibia force versus wearable estimates of tibia force during stance for all trials completed by Subject 3 with a linear trendline fitted to the data according to embodiments of the invention.

Since the ultimate goal of this work is to develop a wearable sensor that can estimate tibia bone loading during everyday activities, it is important to assess the accuracy of wearable estimates across trials and across subjects rather than for a single trial. Plots containing lab versus wearable estimates of tibia load for all trials for each subject were generated and a line of best fit for the entire data set for a subject was obtained in a similar was as was done for each trial. These plots are shown below in FIGS. 8-10 for subjects 1-3 respectively. Results of calibrations for individual subjects are shown in Table 7.

TABLE 7

Root mean square error in calibrated wearable estimates of tibia force across the entire stance phase of gait for each subject.

| | Subject 1 | Subject 2 | Subject 3 |
|---|---|---|---|
| RMSE (BW) | 0.18 | 0.62 | 0.34 |
| RMSE (% Max) | 3.0% | 7.7% | 6.1% |

Figure 11:
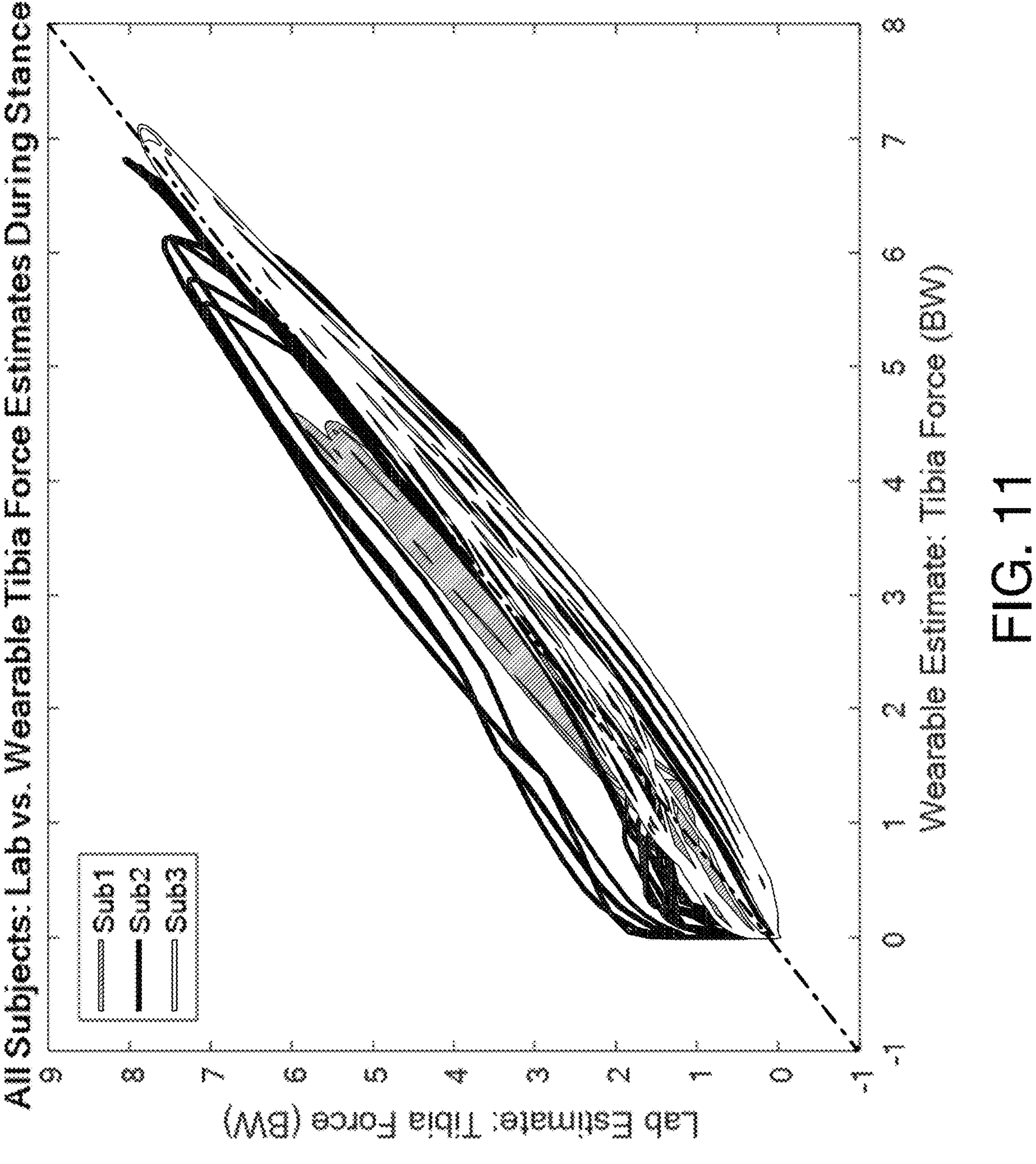
FIG. 11 shows lab estimates of tibia force versus wearable estimates of tibia force during stance for all trials completed by three subjects with a linear trendline fitted to all subject data according to embodiments of the invention.

While it may be possible to calibrate a wearable device for each user, it would be ideal if a single equation could be found to equate lab and wearable estimates of tibia load. As such, data for all three subjects in the study were combined, and an overall line of best fit was obtained. A plot of this data (with subjects shown in different colors) and the best fit line is shown in FIG. 11. The best fit line yielded a root mean square error of 0.49 body weights (6.1% of max).

D. Wearable Estimates of Peak Tibia Force

Ideally, we want to be able to accurately estimate the tibia load throughout the entire stance phase, but this may not always be necessary; it may be that stress fracture development is impacted mainly by the peak forces experienced by the tibia, in which case, only peak forces would need to be accurately estimated. In this section, we analyze the accuracy of raw and calibrated peak tibia forces.

D.1. Raw Estimates

Similar to the first test of accuracy for tibia force over stance, the root mean square error between lab based and raw wearable estimates of peak bone loading during stance was calculated for each subject and for all data combined. Results are included in Table 8. Subject 1 had a root mean square error in peak loading of 1.14 body weights (19.0% of max). Subject 2 had a root mean square error in peak loading of 1.18 body weights (14.6% of max). Subject 3 had a root mean square error in peak loading of 0.71 body weights (9.0% of max).

D.2. Calibrated Estimates

Figure 12:
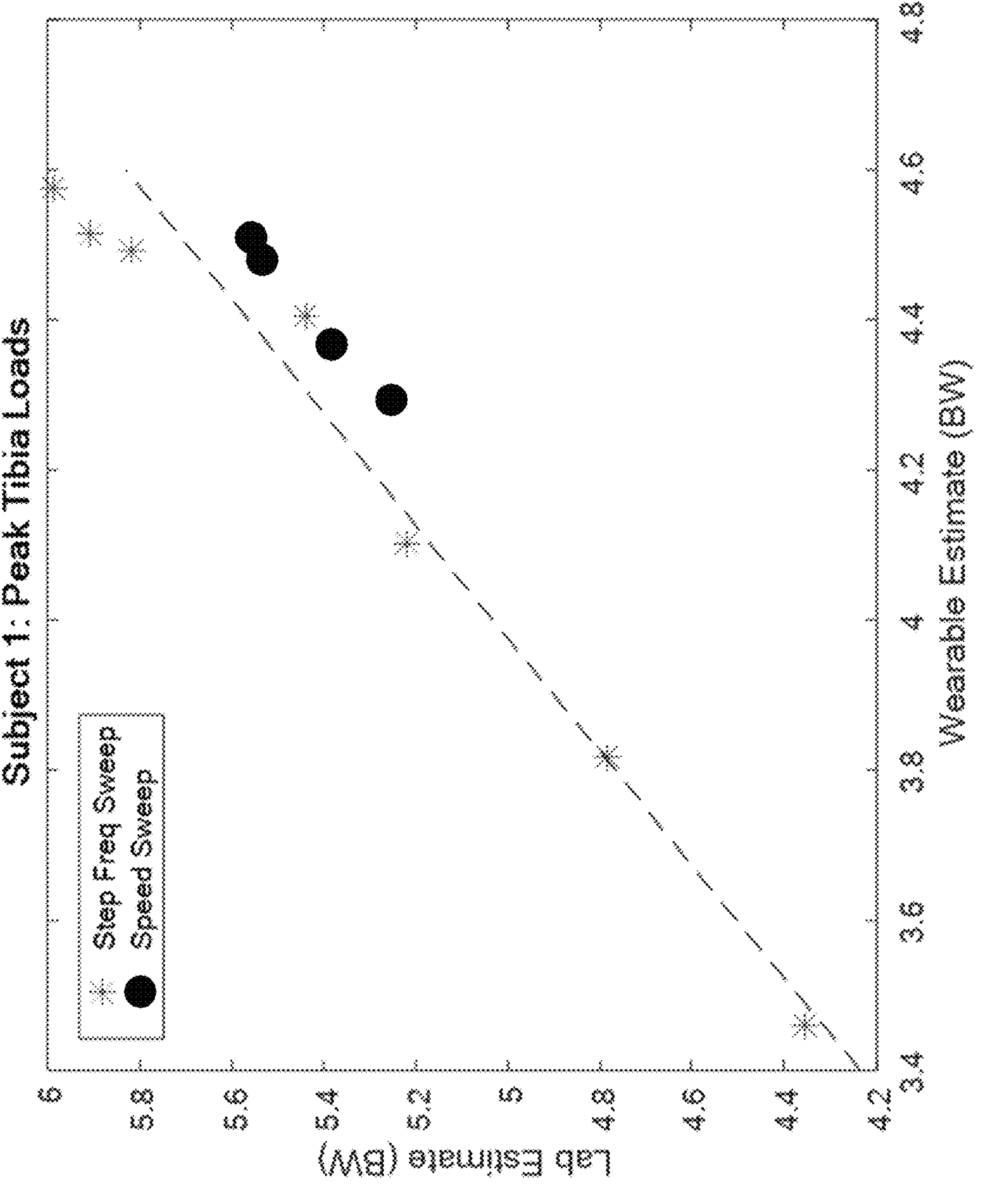
FIG. 12 shows lab estimates of peak tibia force plotted against wearable estimates for Subject 1, with a linear trendline fitted to the data according to embodiments of the invention.
Figure 13:
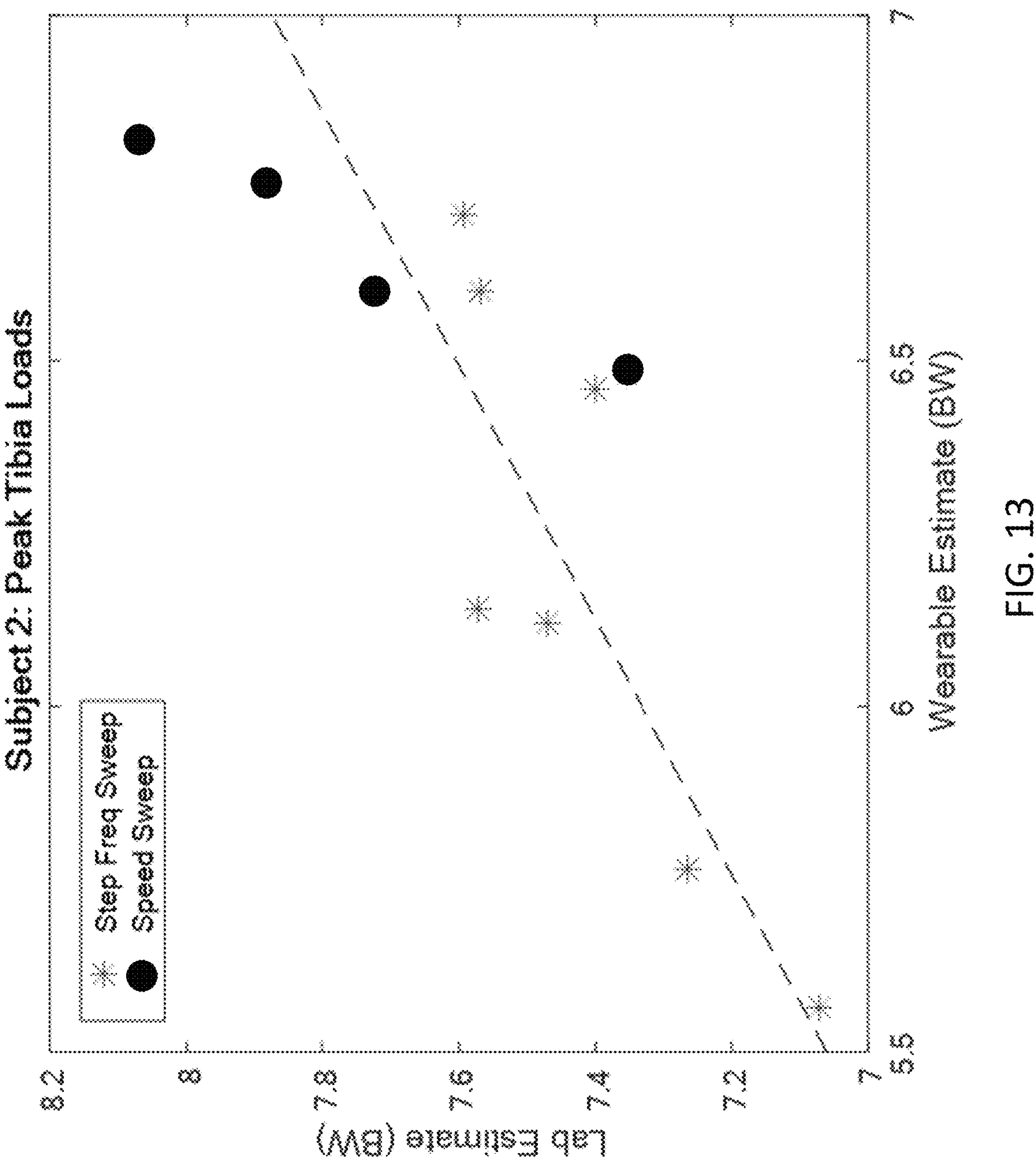
FIG. 13 shows lab estimates of peak tibia force plotted against wearable estimates for Subject 2, with a linear trendline fitted to the data according to embodiments of the invention.
Figure 14:
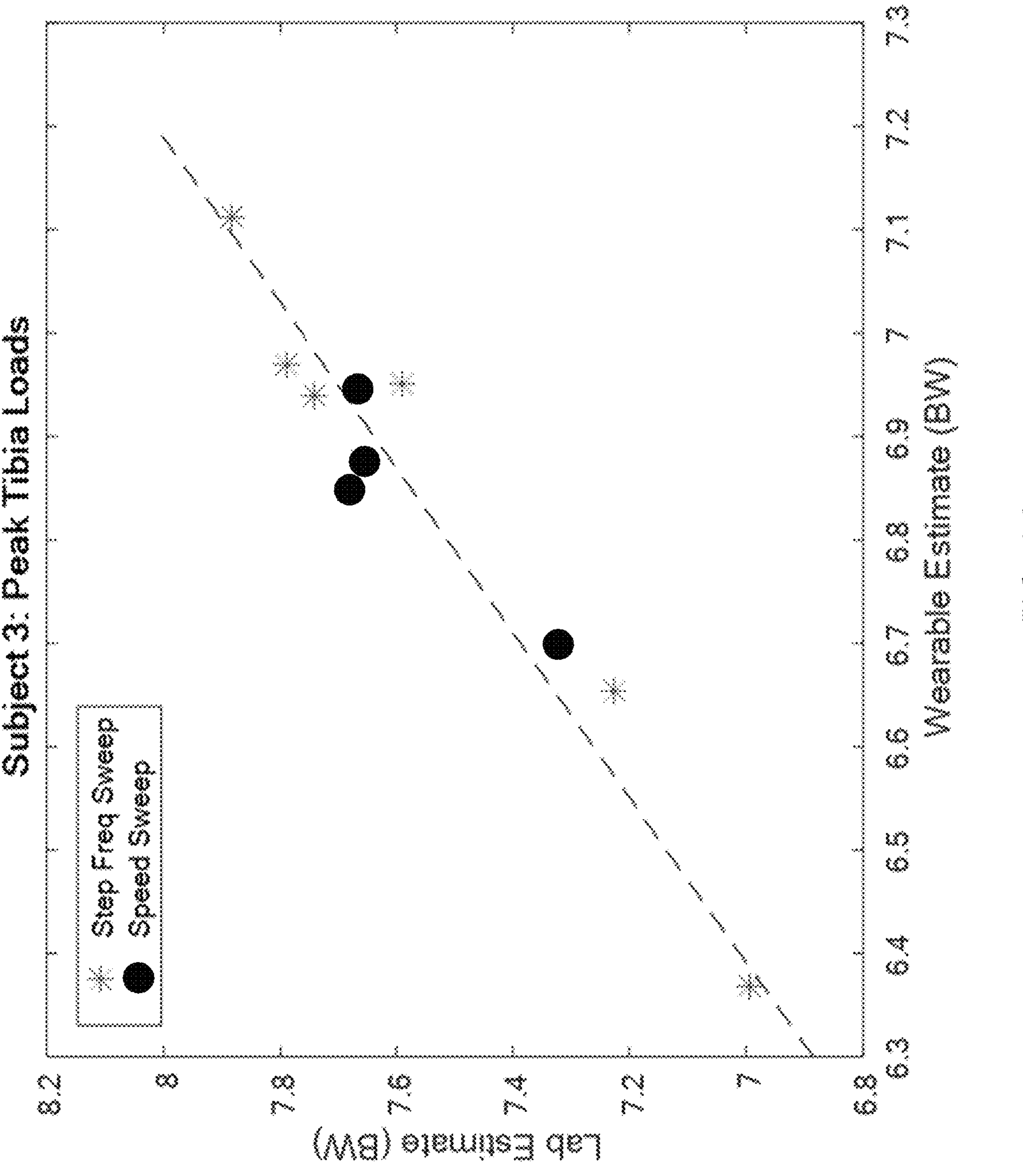
FIG. 14 shows lab estimates of peak tibia force plotted against wearable estimates for Subject 3, with a linear trendline fitted to the data according to embodiments of the invention.

Plots of lab estimates of peak tibia force vs wearable estimates of peak tibia force are included in FIGS. 12-14. A summary of results is shown in Table 8.

TABLE 8

Root mean square error in calibrated wearable estimates of peak tibia force for each subject.

| | Subject 1 | Subject 2 | Subject 3 |
|---|---|---|---|
| $R^2$ | 0.91 | 0.66 | 0.96 |
| RMSE (BW) | 0.15 | 0.16 | 0.08 |
| RMSE (% Max) | 2.5% | 2.0% | 1.0% |

Figure 15:
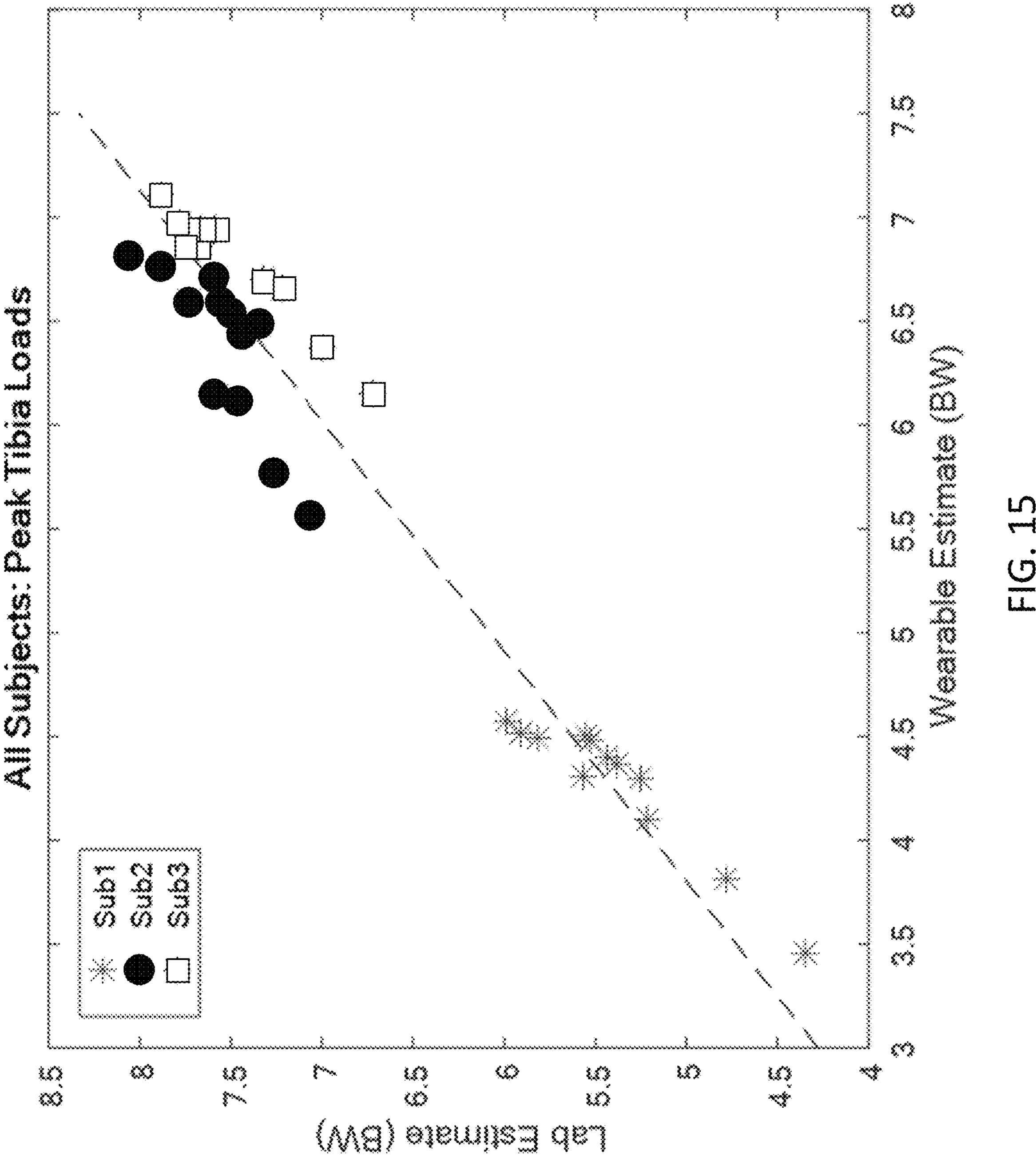
FIG. 15 shows lab estimates of peak tibia force plotted against wearable estimates for all subjects, with a linear trendline fitted to the data according to embodiments of the invention.

A line of best fit was also found for the set of data for all subjects. The plot of lab estimates of peak tibia force versus wearable estimate of peak tibia force is shown in FIG. 15. This overall best fit line is strongly correlated with an r-squared value of 0.95, and has a root mean square error of 0.25 body weights (3.1% of max).

E. Wearable Estimates of Tibia Load per Kilometer

In addition to peak tibia force, tibia load per kilometer has been identified as a metric that may help to quantify the cumulative effects of tibia bone loading cycles, so wearable estimates of this metric is also analyzed.

E.1. Raw Estimates

Following the same procedure as for tibia force during stance and peak tibia force, root mean square error between lab and raw wearable estimates of tibia load per kilometer was calculated for each subject and for all data combined. Subject 1 had a root mean square error in load per kilometer of 193.5 body weights times seconds (20.6% of max). Subject 2 had a root mean square error in load per kilometer of 136.7 body weights times seconds (13.4% of max). Subject 3 had a root mean square error in load per kilometer of 45.0 body weights times seconds (4.6% of max).

E.2. Calibrated Estimates

Figure 16:
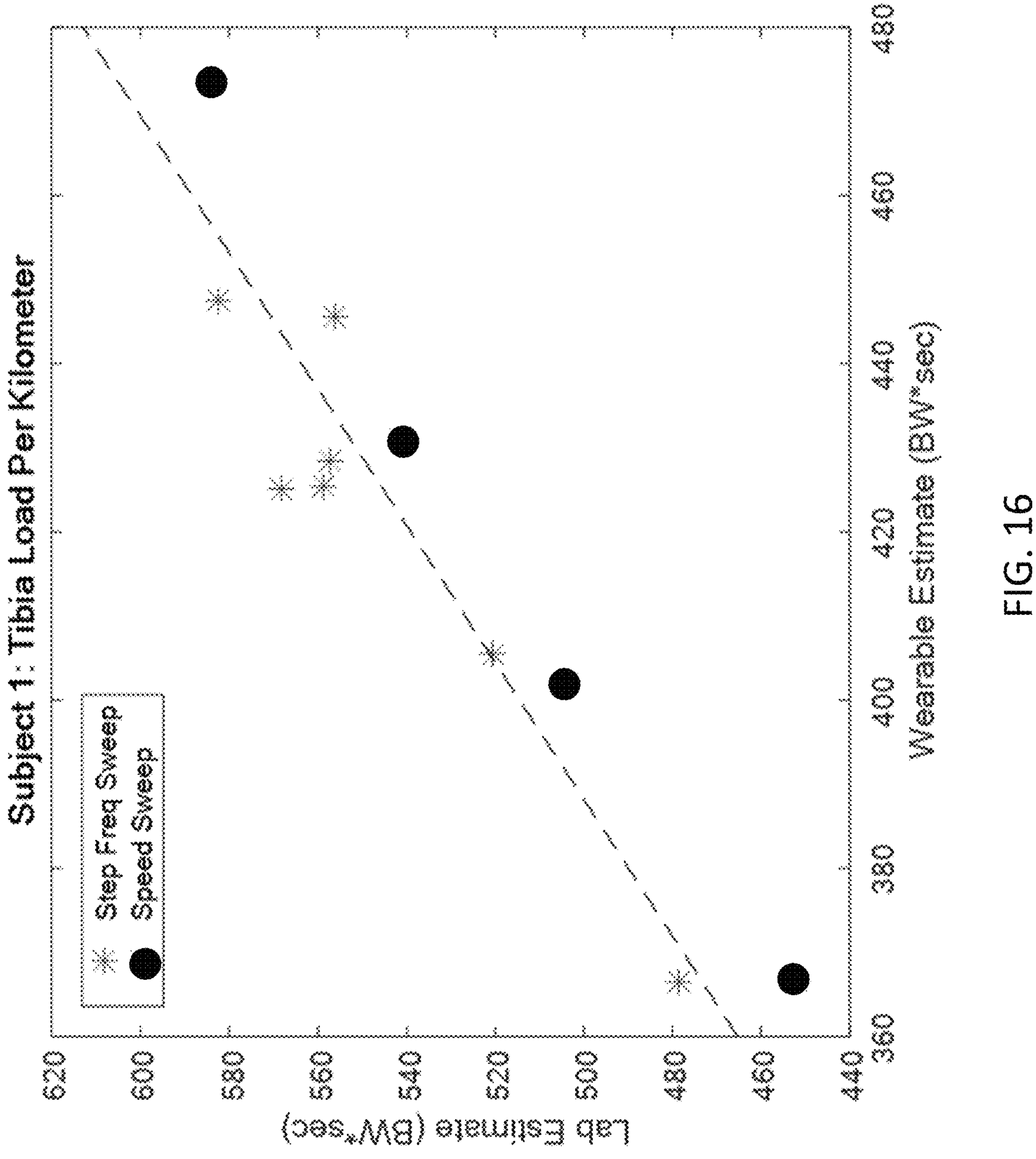
FIG. 16 shows lab estimates of tibia load per kilometer plotted against wearable estimates for Subject 1, with a linear trendline fitted to the data according to embodiments of the invention.
Figure 17:
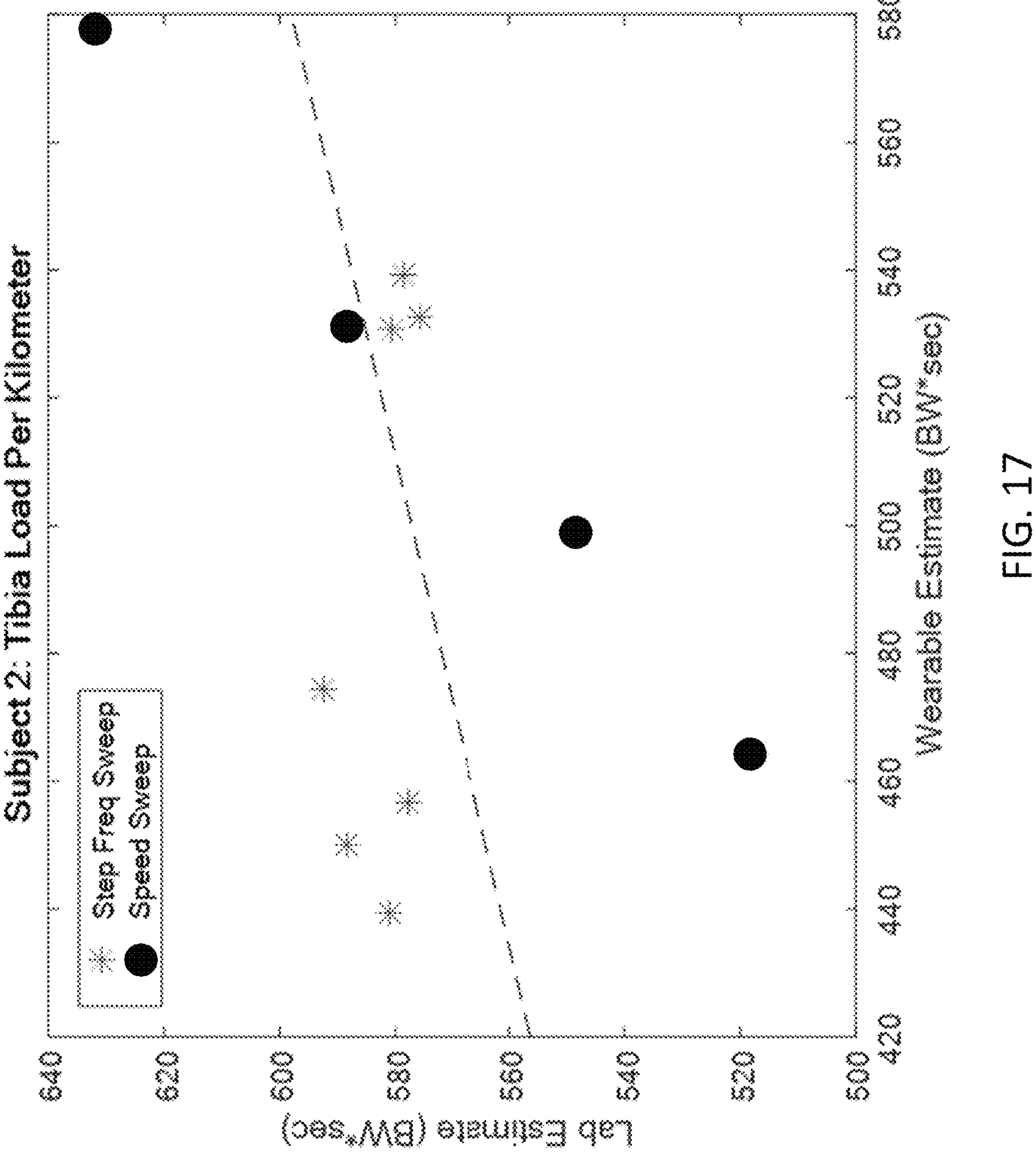
FIG. 17 shows lab estimates of tibia load per kilometer plotted against wearable estimates for Subject 2, with a linear trendline fitted to the data according to embodiments of the invention.
Figure 18:
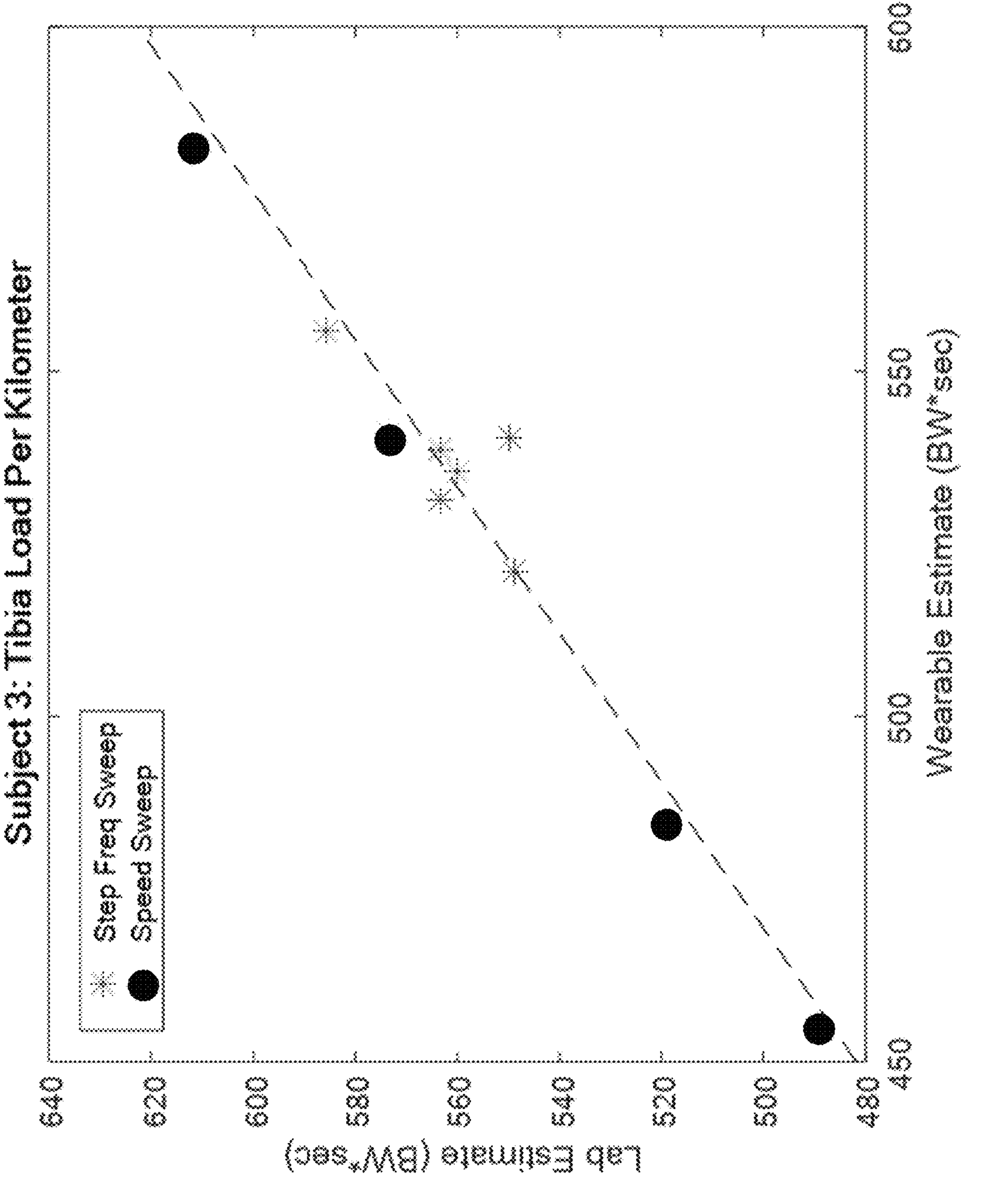
FIG. 18 shows lab estimates of tibia load per kilometer plotted against wearable estimates for Subject 3, with a linear trendline fitted to the data according to embodiments of the invention.

Plots of lab estimates of tibia load per kilometer vs wearable estimates of tibia load per kilometer are included in FIGS. 16-18. Tibia load per kilometer tended to be underestimated by wearable sensors, and data points for the speed sweep trials tended to follow a more linear pattern than the step frequency sweep data points. A summary of results is included in Table 9.

TABLE 9

Root mean square error in calibrated wearable estimates of tibia load per kilometer for each subject.

| | Subject 1 | Subject 2 | Subject 3 |
|---|---|---|---|
| $R^2$ | 0.85 | 0.18 | 0.95 |
| RMSE (BW * sec) | 16.64 | 25.65 | 7.42 |
| RMSE (% Max) | 2.9% | 4.1% | 1.2% |

Figure 19:
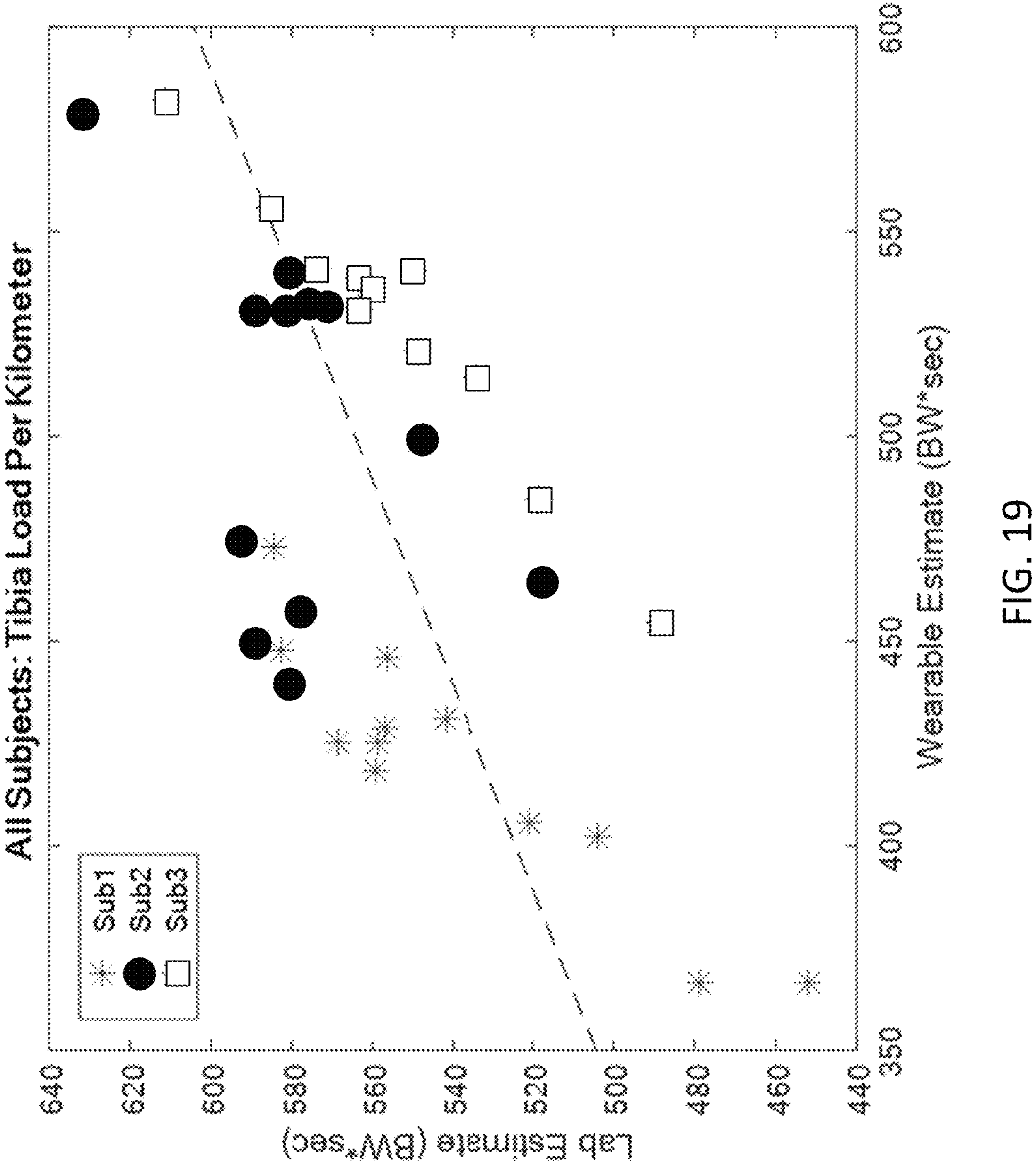
FIG. 19 shows lab estimates of tibia load per kilometer plotted against wearable estimates for all subjects, with a linear trendline fitted to the data according to embodiments of the invention.

A line of best fit was also found for the set of data for all subjects. The plot of lab estimates of tibia load per kilometer versus wearable estimate of tibia load per kilometer is shown in FIG. 19. This overall best fit line is somewhat correlated with an r-squared value of 0.40, and has a root mean square error of 29.3 body weights times seconds (4.6% of max).

Discussions

A. Evaluation of Accuracy

The initial hypothesis that the wearable estimate of tibia bone loading would be within a 10 percent root mean square error of the lab estimates is supported by the data obtained in this study. When calibrated with a scaling factor and constant offset (determined from a best fit line) on a subject by subject basis, accuracies between 3.0 and 7.7% for force across the entire stance phase, 1.0 and 2.5% for peak force, and 1.2 and 4.1% for load per kilometer were achieved. With a single calibration for all subjects, accuracies of 6.1% for force across the entire stance phase, 3.1% for peak force, and 4.6% for load per kilometer were achieved. For a relatively simple estimation method and small number of sensors (pressure insoles and a single IMU), these results are highly promising.

B. Limitations

The current study analyzes a set of data averaged over a 20 second trial for each condition. While this is useful as a proof of concept for utilizing wearable sensors as surrogates for lab measurements in the calculation of tibia load, it is ultimately desired to have a device that can record data for all strides, not just an average. With so many open questions related to stress fracture development, we wish to develop a wearable device to measure bone loading that can collect as much accurate data as possible to analyze. Individual steps with high tibia loads or loading rates may be particularly interesting to investigate and should therefore be validated in a similar manner to this study. Specifically, the best fit lines found to correct wearable estimates of tibia load to more closely match lab estimates may work on an average cycle but may not be as accurate on individual cycles. It remains to be determined whether a single calibration (either for a single subject or overall) would result in accurate estimates of step to step changes in bone loading within a single condition as well as across conditions. Furthermore, although results of using a single calibration for all subjects appears promising in these results, it should be noted that only three subjects were added, so errors may increase with the inclusion of more subjects, and subject specific calibrations may become necessary to achieve the desired range of accuracy in wearable estimates of tibia loads.

C. Areas for Improvement

Aside from correcting wearable estimates for scaling and offset errors, there are many possible ways that estimates could be improved. First, better calibration and placement of sensors could help to improve accuracy of individual measurements such as force from pressure insoles or shank angle from an IMU. Along the same lines, the development of more accurate sensors could help to reduce the error in tibia force estimates. Other methods of compensating for lower quality data from wearable sensors, such as the one dimensional ground reaction force instead of the true three dimensional vector, may be investigated. For example, it may be possible to assume a given angle trajectory of the ground reaction force, which could be used in conjunction with the IMU shank angle to get a more accurate projection of ground reaction force onto the tibia. Beyond improving individual sensor data, a more complex estimation method could be implemented, taking into account portions of bone loading that were neglected in this study, such as contributions of foot inertia, ligaments, or co-contracting muscles, or variable moment arm of the muscles producing forces on the bone. It may also become apparent that simple substitutions of data into the inverse dynamics equation does not yield results that are accurate enough for applications in injury prevention, so more sophisticated data processing, including machine learning, could be implemented to design a more accurate data fusion algorithm.

E. Implementation

While an experiment in a laboratory setting is necessary for a study such as this, whose objective is to determine the accuracy of an estimation method, these results represent many ideal conditions that may not be present in everyday conditions in which an ultimate product would be used. For example, sensor placement would likely not be as secure or well calibrated by a user when compared to a trained researcher. This could result in inaccurate measurements or noise in the data due to movement of the physical sensors. Additionally, should the algorithm proposed in this study be implemented in a consumer device, there would be several limiting factors that may reduce the capabilities of the device or individual sensors, including cost, size, power and battery life, form factor or aesthetic, and durability. Furthermore, all calculations and analysis in this study were done in post-processing, whereas in a consumer device, it would likely be desirable to perform these calculations in real time. Therefore, the device would need to integrate a processing system and programming would need to be done ahead of time. While not necessarily impossible, these limitations would make it difficult to exactly replicate the accuracy of wearable estimates in a real device.

F. Alternate Estimation Method: Regression Equation

The benefit of fusing wearable sensor data to estimate tibia bone loading is that it aims to track the source of loading that can cause stress fractures. Nevertheless, for certain ranges of running speed, step frequency, and/or varying terrains, there may also be other metrics which are less directly or causally related to bone stress fracture risk that might also provide a correlated surrogate estimate of loading. For instance, a simple regression equation combining speed and step frequency might provide useful information about tibia bone loading over some range of running conditions. However, it is important to recognize that such spatiotemporal metrics have no direct connection to the physical forces on the bone, the ultimate cause of stress fractures. Therefore, if runners adjust their technique as they become fatigued, or run differently from one run to another, a fixed relationship between bone load and spatiotemporal parameters may not exist.

G. Desired Accuracy of Estimates

It remains to be determined just how accurate a device would need to be to detect whether or not a user is at risk of developing a stress fracture injury, but in order to find the required accuracy, an algorithm must first be developed. It is reasonable to believe that errors of 0.01 body weights or less would have little impact on determining stress fracture injury risk, given that peak loading of the bone is between 4 and 8 body weights. On the other hand, we know that errors of 10 body weights or more would be unacceptable since this would mean that peak loading could be estimated as zero or negative. Accuracy within one tenth to one body weight, as achieved in this experiment, may be acceptable, but after the testing of a device, it may be determined that a higher accuracy is necessary to detect the magnitude of changes to bone loading associated with stress fracture development.

Step frequency and speed represent two running metrics that may change from run to run or over the course of a training regimen. However, these are not the only factors that may change, and are not the only variations in running that result in changes in bone loading. For example, running on up or down an incline will result in different forces felt by the tibia than running on level ground, but these conditions were not investigated in this study. Similarly, all trials in this experiment were performed on a smooth treadmill surface, but runners often experience rugged and varying terrains on everyday runs, and the resulting changes to bone loading were not determined in this study. These additional factors may influence the accuracy of wearable sensors, so future work in this area includes investigating how these factors and others contribute to bone loading, and how the proposed tibia force estimation method performs in these conditions.

Tibia stress fractures are a prevalent injury in recreational runners, military recruits, and other active populations, yet little is known about the root causes of injury or how to identify potential risk factors prior to the onset of symptoms. Substantial progress has been made in the field of wearable technology for health and fitness monitoring in the last decade, and interest in these devices is high. Given the advances in sensors and data analytics, it may be possible to design a device that can measure tibia bone loading and help researchers determine indicators of stress fracture development, and ultimately alert users of potential injury risks. The goal of this study was to determine whether wearable sensor data could be used in an inverse dynamics-based method of calculating tibia force, an adaptation of the methods commonly used in a laboratory setting, to obtain accurate tibia force curves for running trials. While the level of accuracy required is not well-established, the initial goal was to obtain estimates within 10% root mean square error of lab estimates. Using the inverse dynamics approach with calibration, root mean square errors of 6.1% of peak force across the entire stance phase of running were obtained. This level of accuracy, particularly for a preliminary test of a relatively simple algorithm, is extremely promising, and motivates future work in this area. Once further testing and validation is completed, this method of calculating tibia bone loading in a portable system could help to improve our fundamental understanding of stress fracture injury and may even have applications in studying and detecting other musculoskeletal loading injuries.

Example 2

Beyond Ground Reaction Forces: Towards Wearable Tech to Monitor Bone Loading and Prevent Injury The purpose of this example was to determine if increases in GRF peaks or loading rate were correlated with increases in peak tibia bone loading during running. In the example, running and tibia bone loading were focused, because of the high prevalence of tibia stress fractures in runners. We hypothesized that increases in common GRF metrics (impact and active peaks, impact loading rate) would not be strongly correlated with increases in peak tibia loading as runners varied speed, step frequency and terrain slope (i.e., $r<0.8$). The absence of strong correlation would suggest the need to fuse data from additional/alternative sensors, moving beyond GRF measures, to non-invasively monitor bone loading.

Methods

Three healthy subjects (2 M, 1 F, height 1.8±0.1 m, weight 66.8±7.0 kg, age 24.6±1.5 years) have participated in this ongoing study. Subjects performed various running trials on a treadmill: (i) 20 total trials at 4 different speeds, ranging from 2.0-3.0 m/s, using self-selected step frequency at each speed, and 5 different slopes ranging from −6 to +6 degrees, (ii) 7 trials at 2.6 m/s but varying step frequency from −15% to +15% of their self-selected step frequency (enforced via metronome). Parameter ranges were selected to reflect variability that a recreational runner might encounter.

Data collection and processing: Unilateral lower-limb kinematics (100 Hz) and GRFs (1000 Hz) were collected. Subjects provided informed consent prior to participation. For each trial, data were collected for 20 seconds, individual steps were parsed out, and outcome metrics were computed on a step-by-step basis and then averaged.

Figures 20A, 20B:
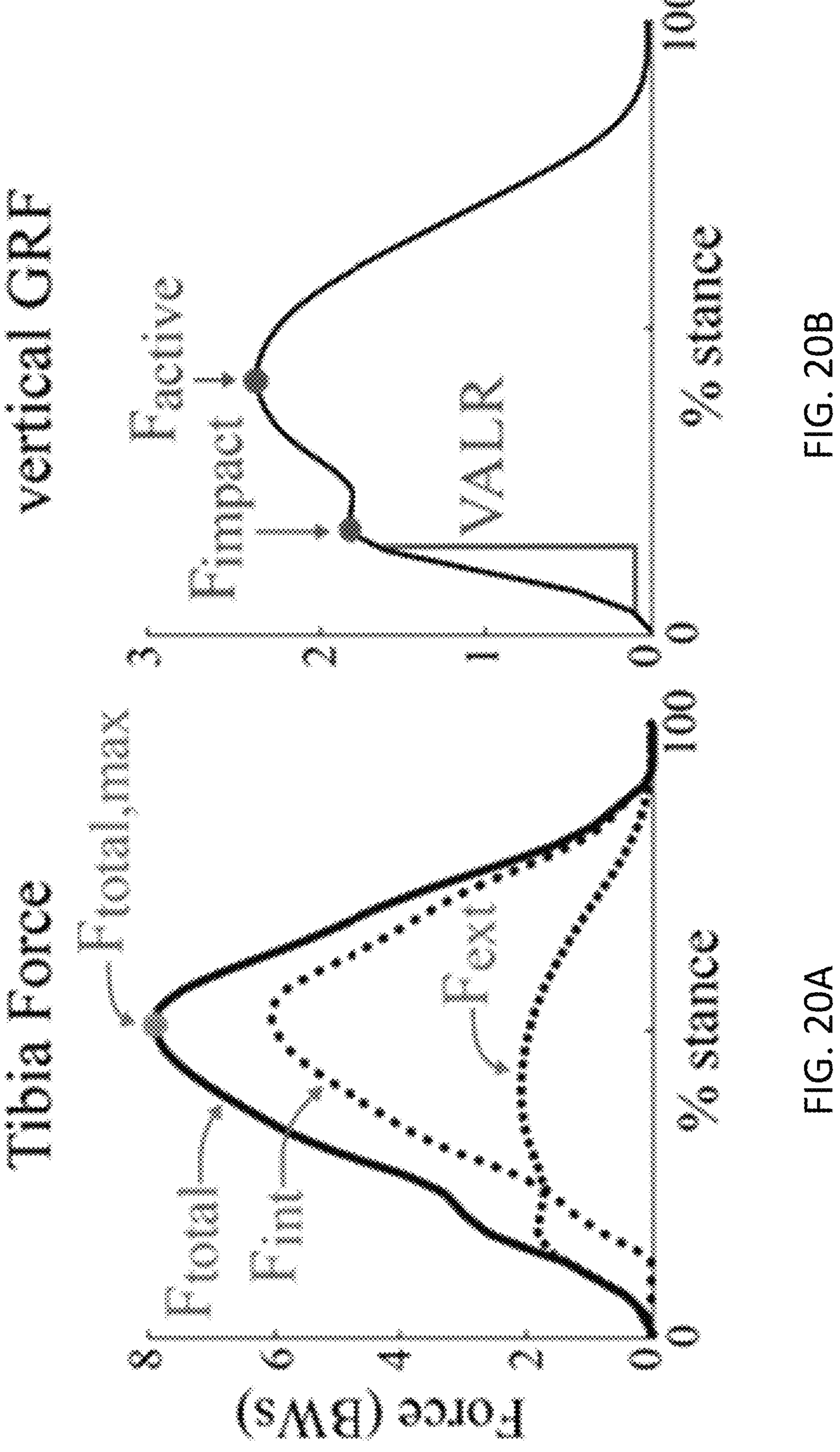
FIG. 20A shows total tibia load summation with running 2.8 m/s, according to embodiments of the invention.
FIG. 20B shows vertical GRF metrics according to embodiments of the invention.

Tibia bone loading: An established inverse dynamics analysis was used to estimate the total tibia compression force ($F_{total}$, FIG. 20A), due to internal (muscle) and external (GRF) sources [1]. The external contribution ($F_{ext}$) was calculated as the measured GRF projected onto the long axis of the tibia. The internal force contribution ($F_{int}$) was calculated as the estimated ankle moment divided by the Achilles tendon moment arm (5 cm, assumed constant). Peak tibia force ($F_{total,max}$) was calculated as the maximum of $F_{total}$ across stance. Forces were normalized by subject BW.

GRF: Three common GRF metrics were calculated: $F_{active}$ (vertical GRF active peak), $F_{impact}$ (vertical GRF impact peak) and VALR (vertical GRF average loading rate, FIG. 20B). For each subject, individual GRF metrics were linearly correlated to peak tibia force. The Pearson correlation coefficient (r) was computed for all trials, and also for each parameter sweep, then averaged across subjects.

Results and Discussions

Figure 21:
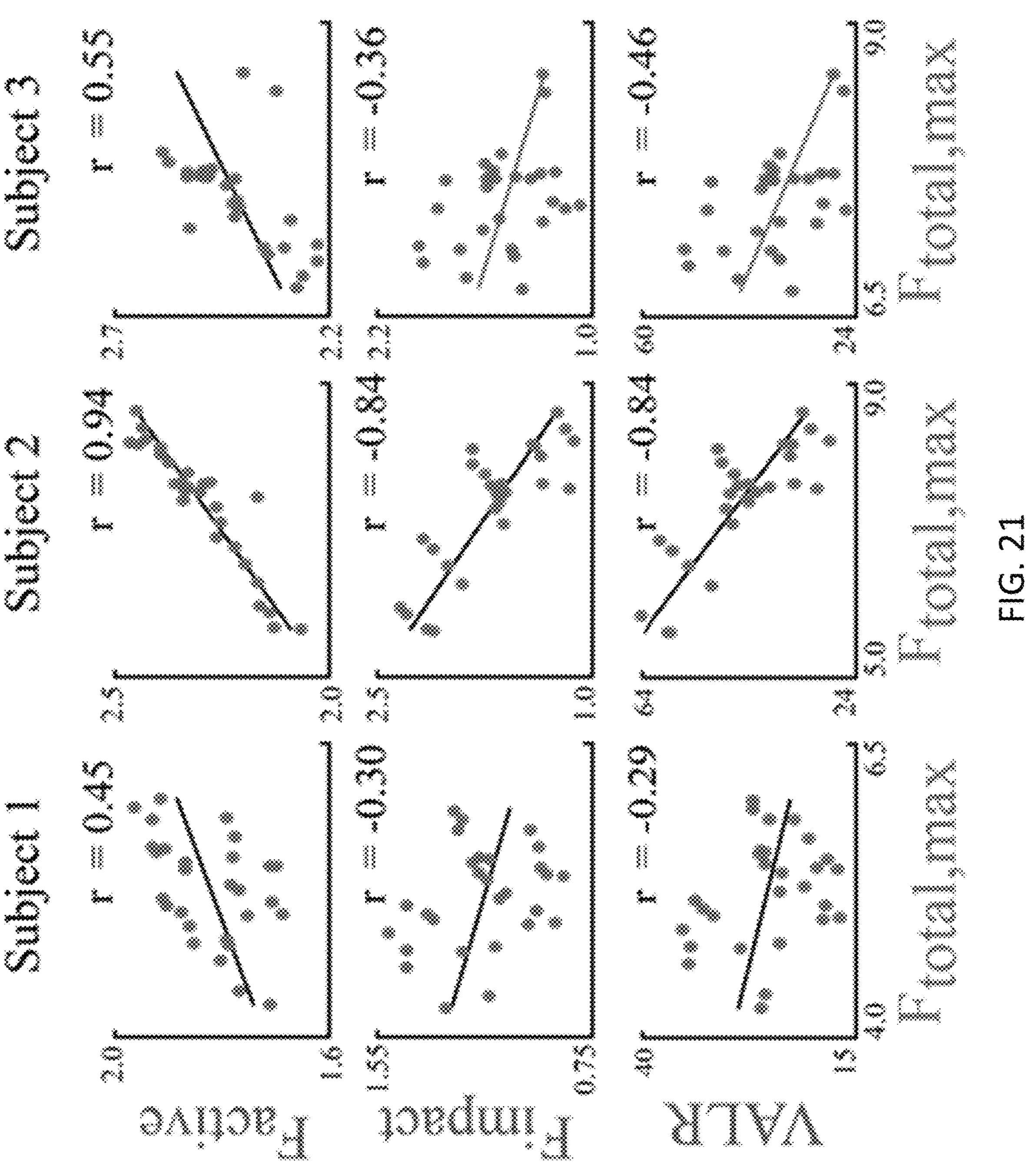
FIG. 21 shows each data point represents the average of one trial according to embodiments of the invention. Force in BWs. VALR in BWs/s.
Figure 22A:
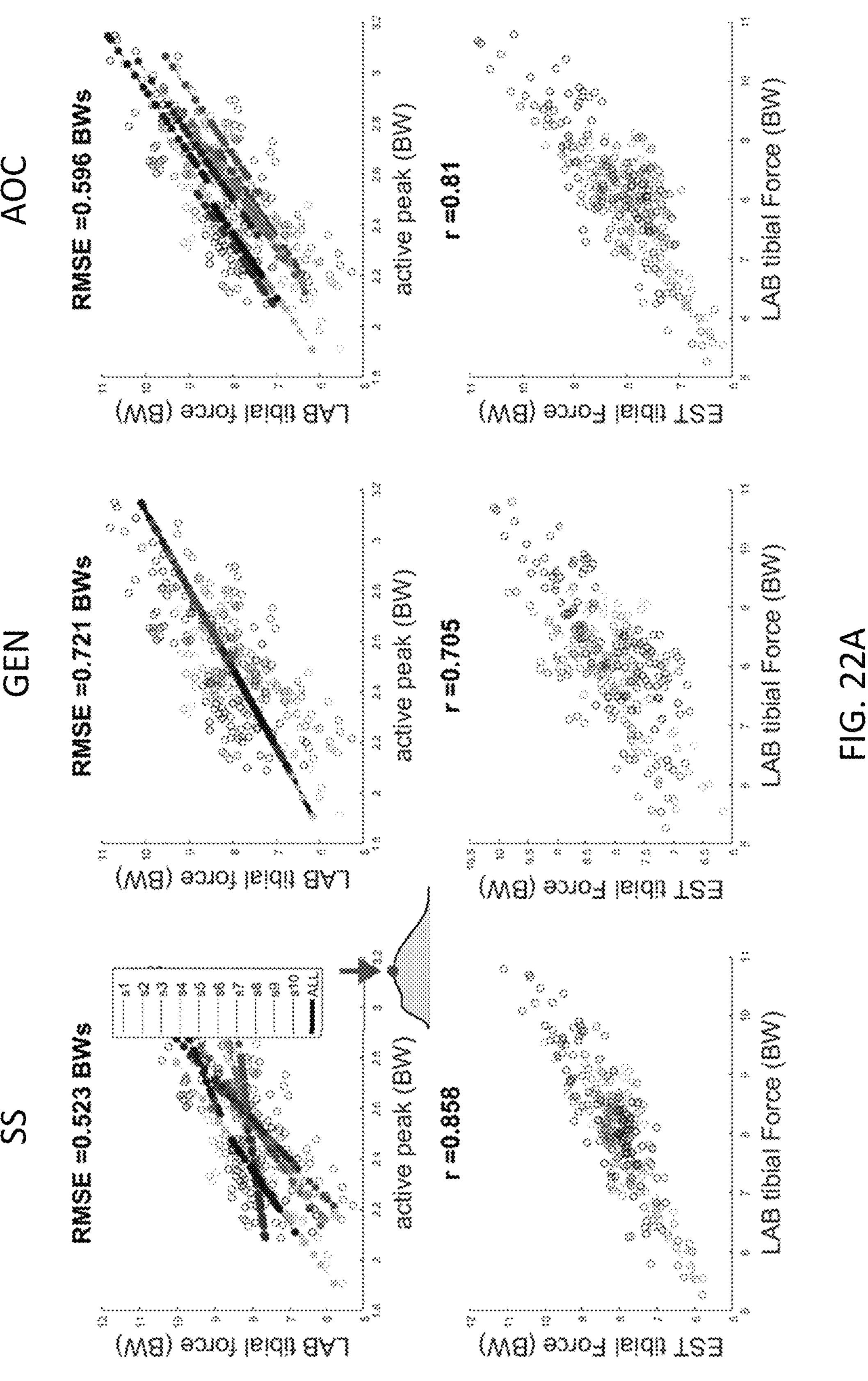
Figure 22C:
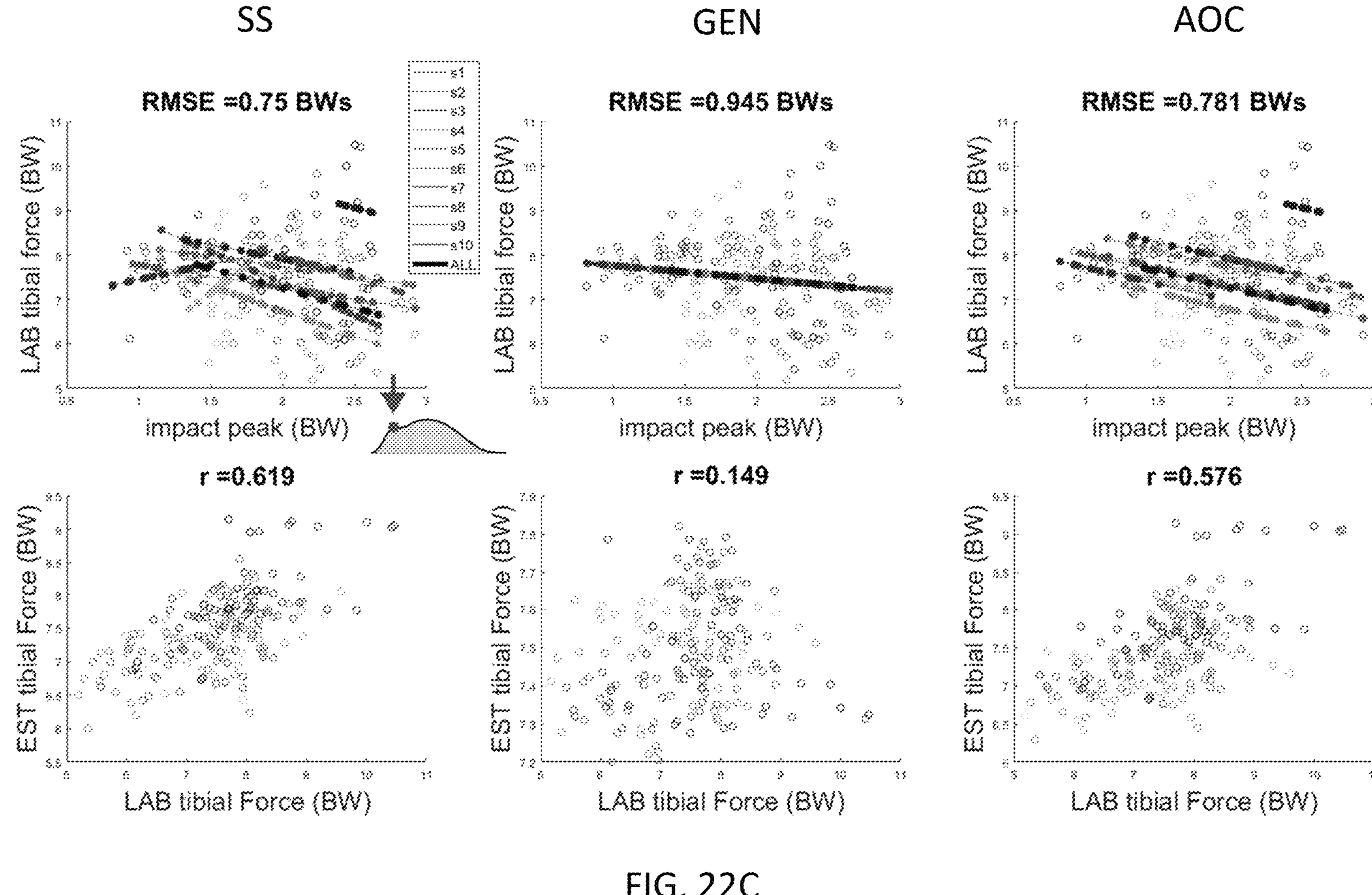
Figure 22E:
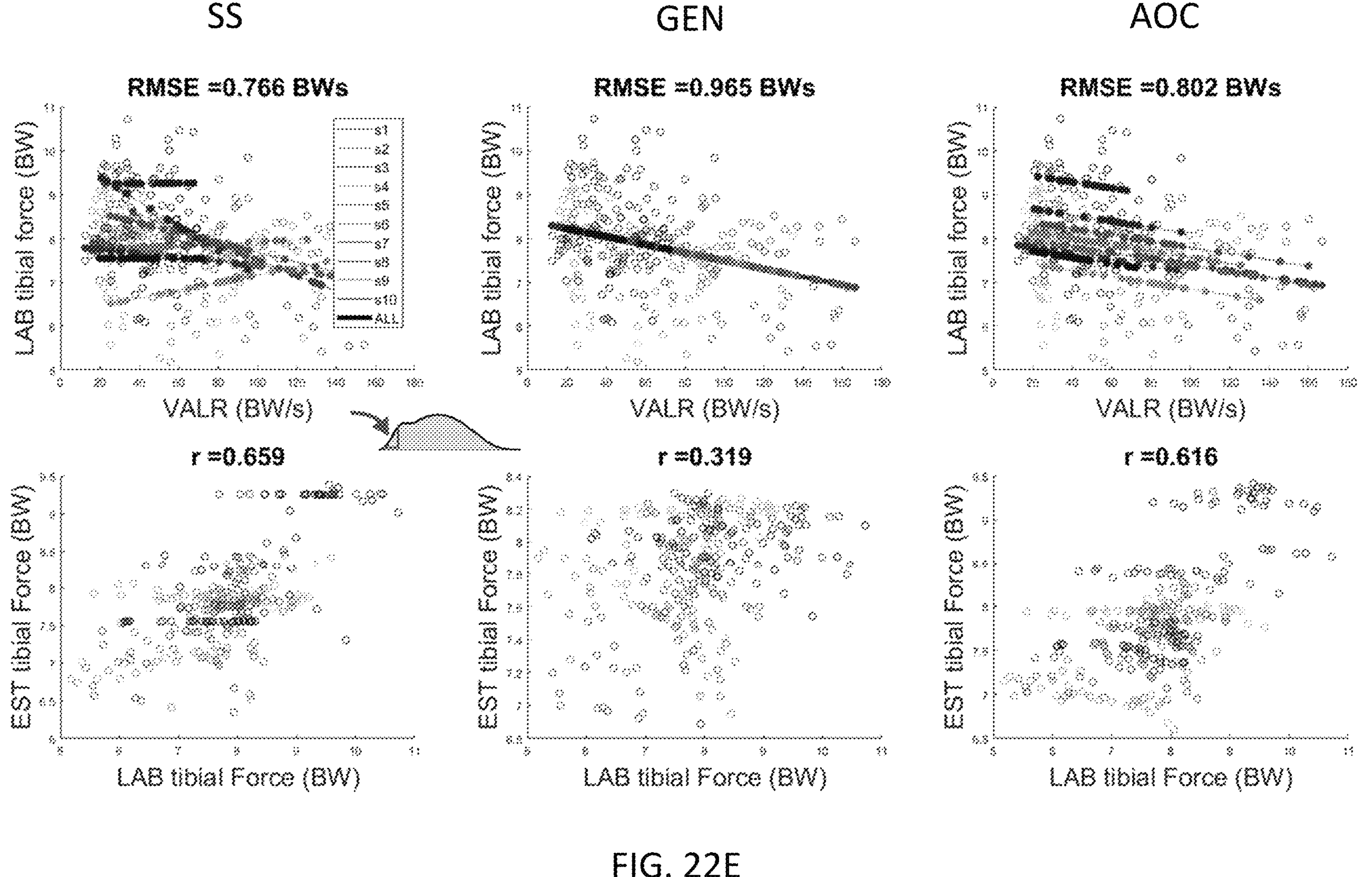
Figure 22G:
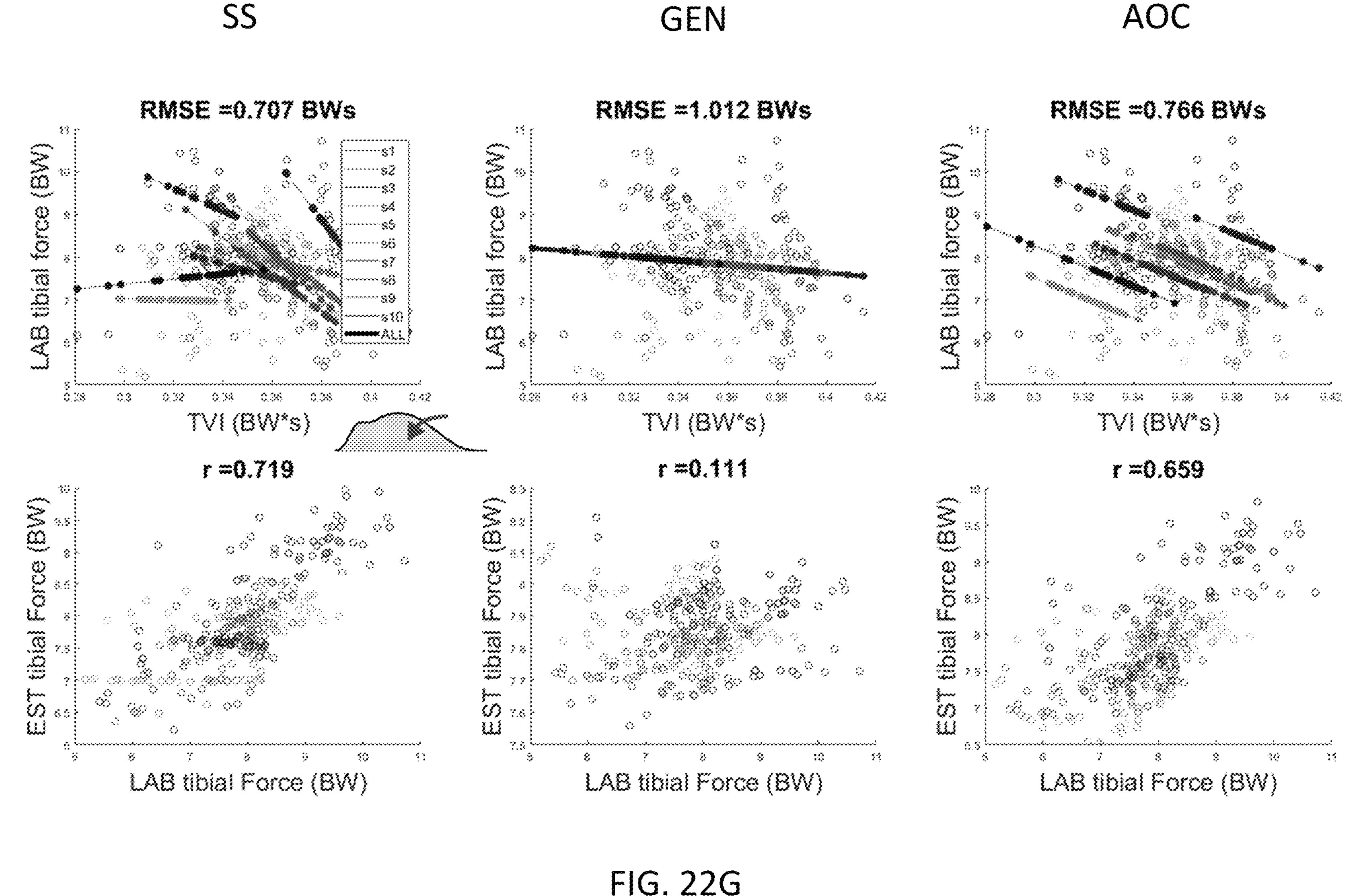
Figure 22I:
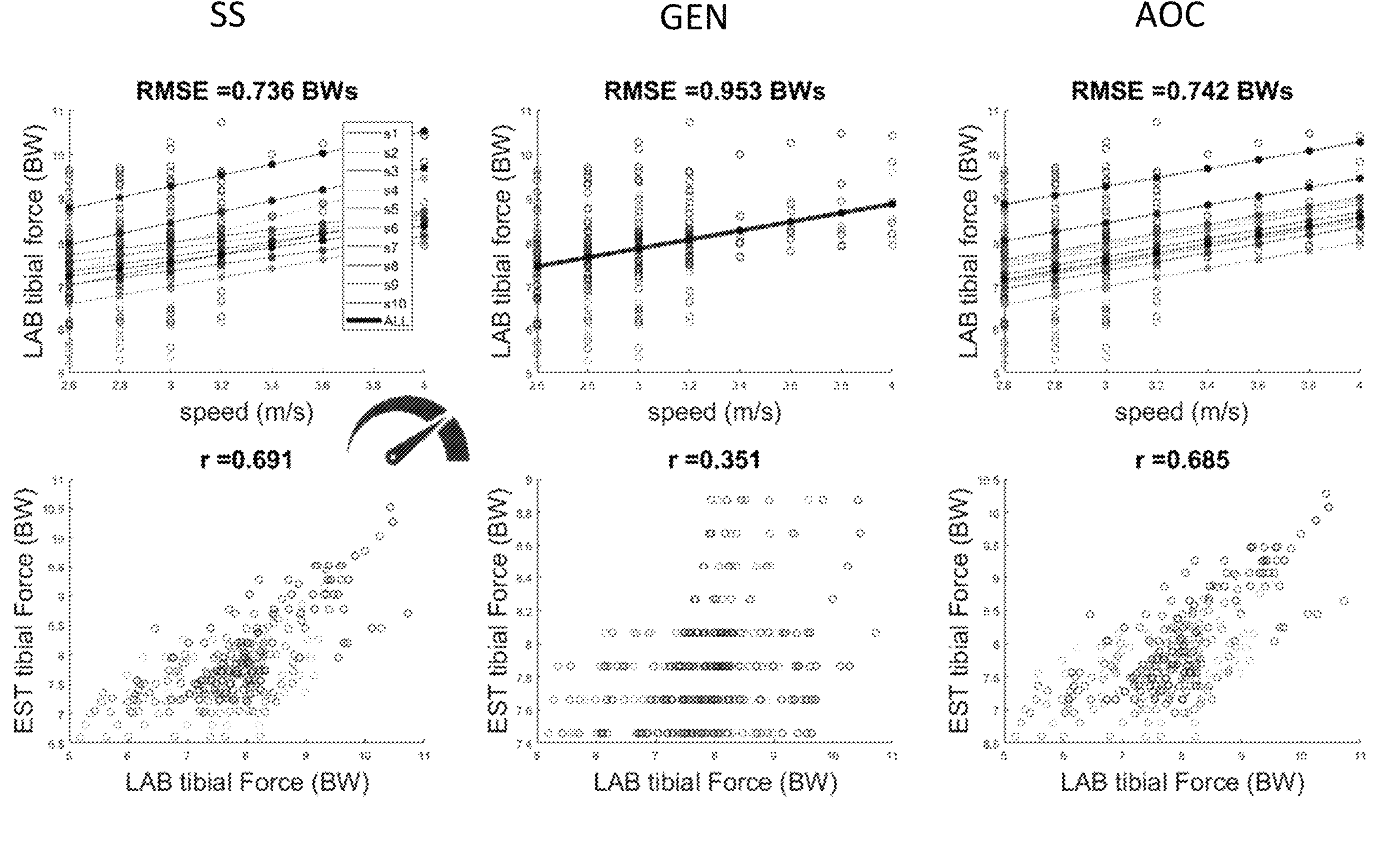
Figure 22K:
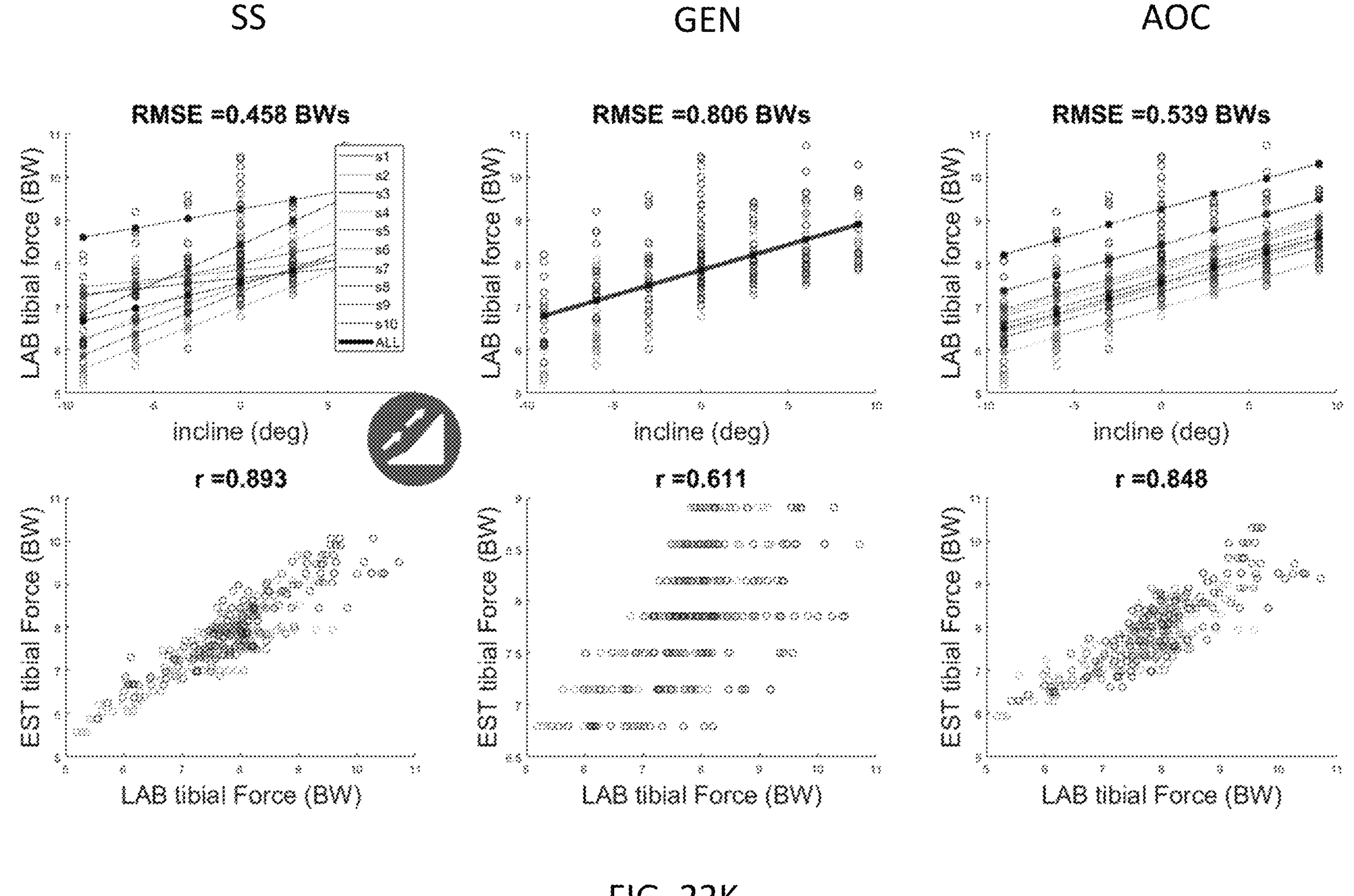
Figure 22M:
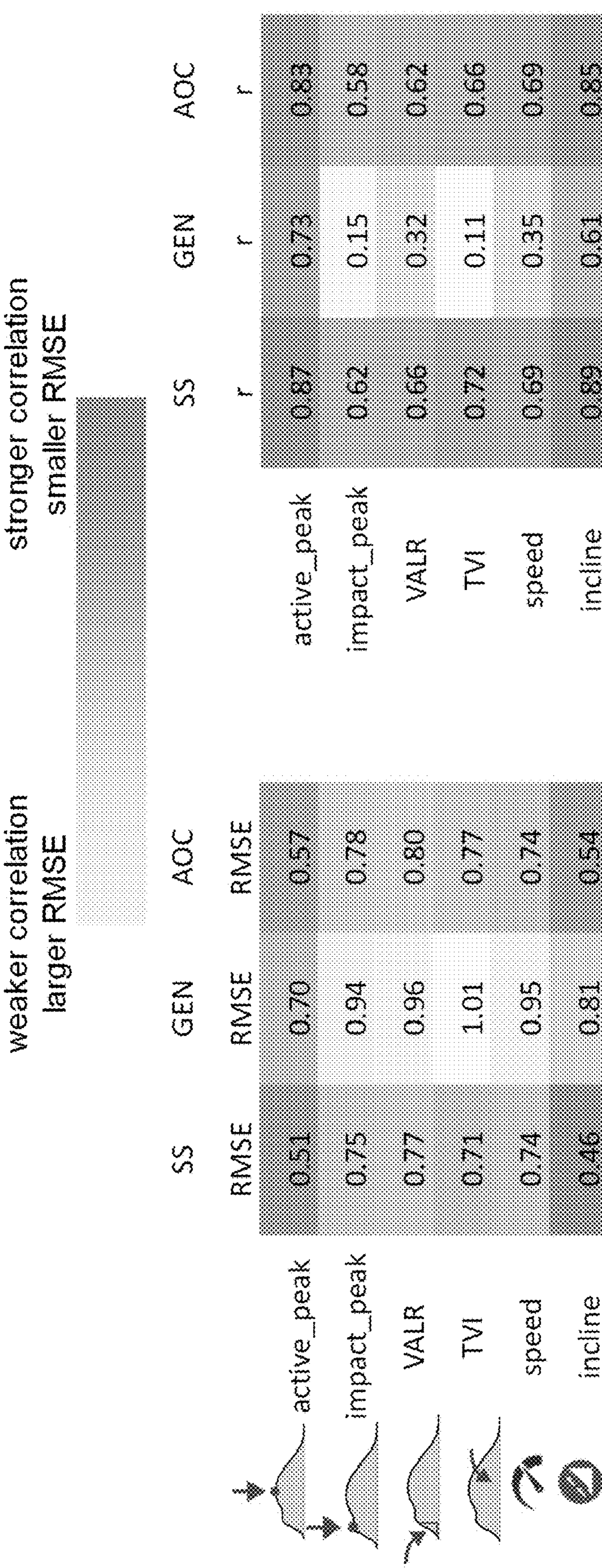
Figure 23A:
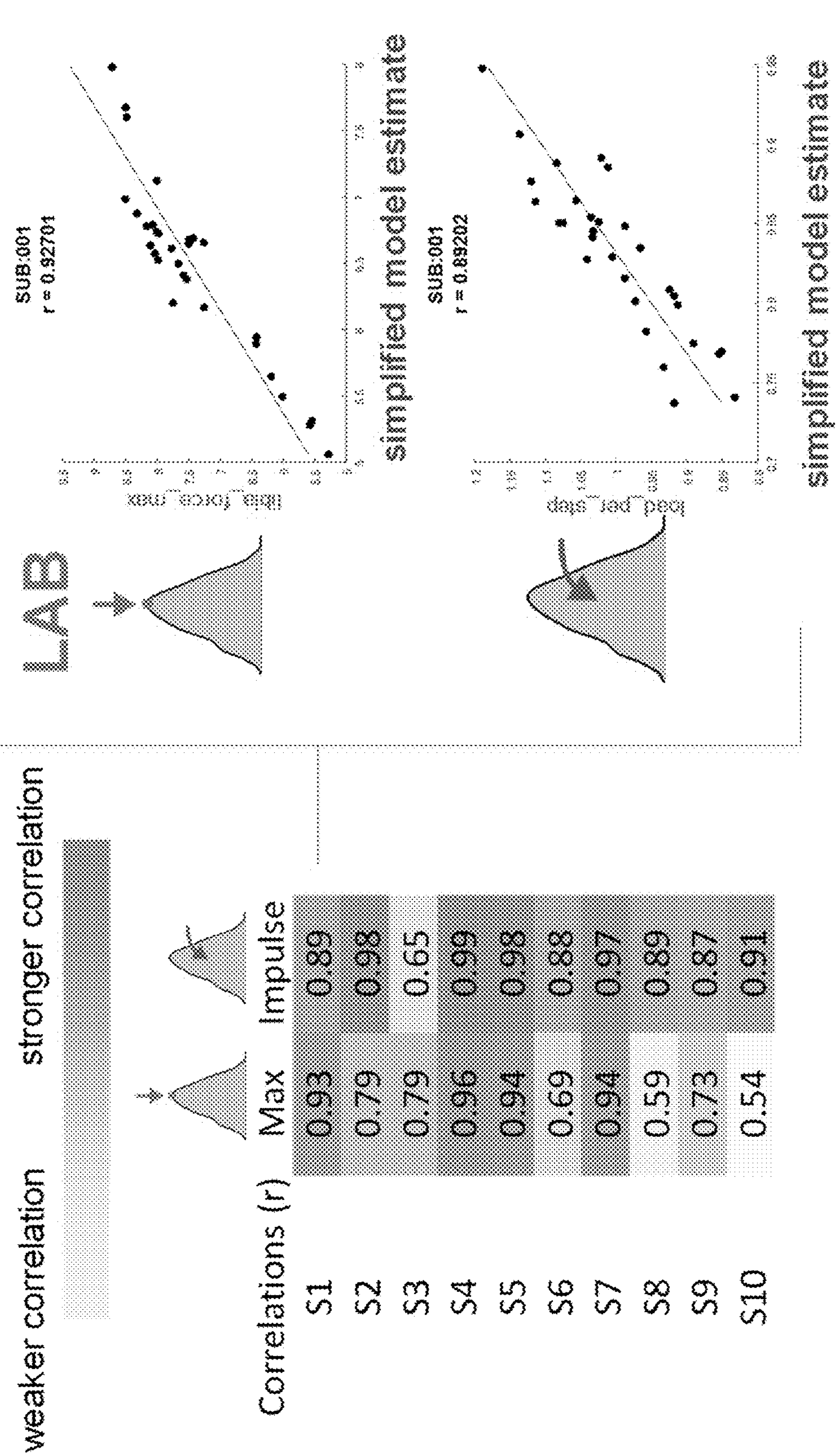
FIGS. 23A-23B show lab tibia forces and estimated tibia forces and their correlations and the root mean square error processed using simplified inverse dynamic approach under different conditions, according to embodiments of the invention.
Figure 23B:
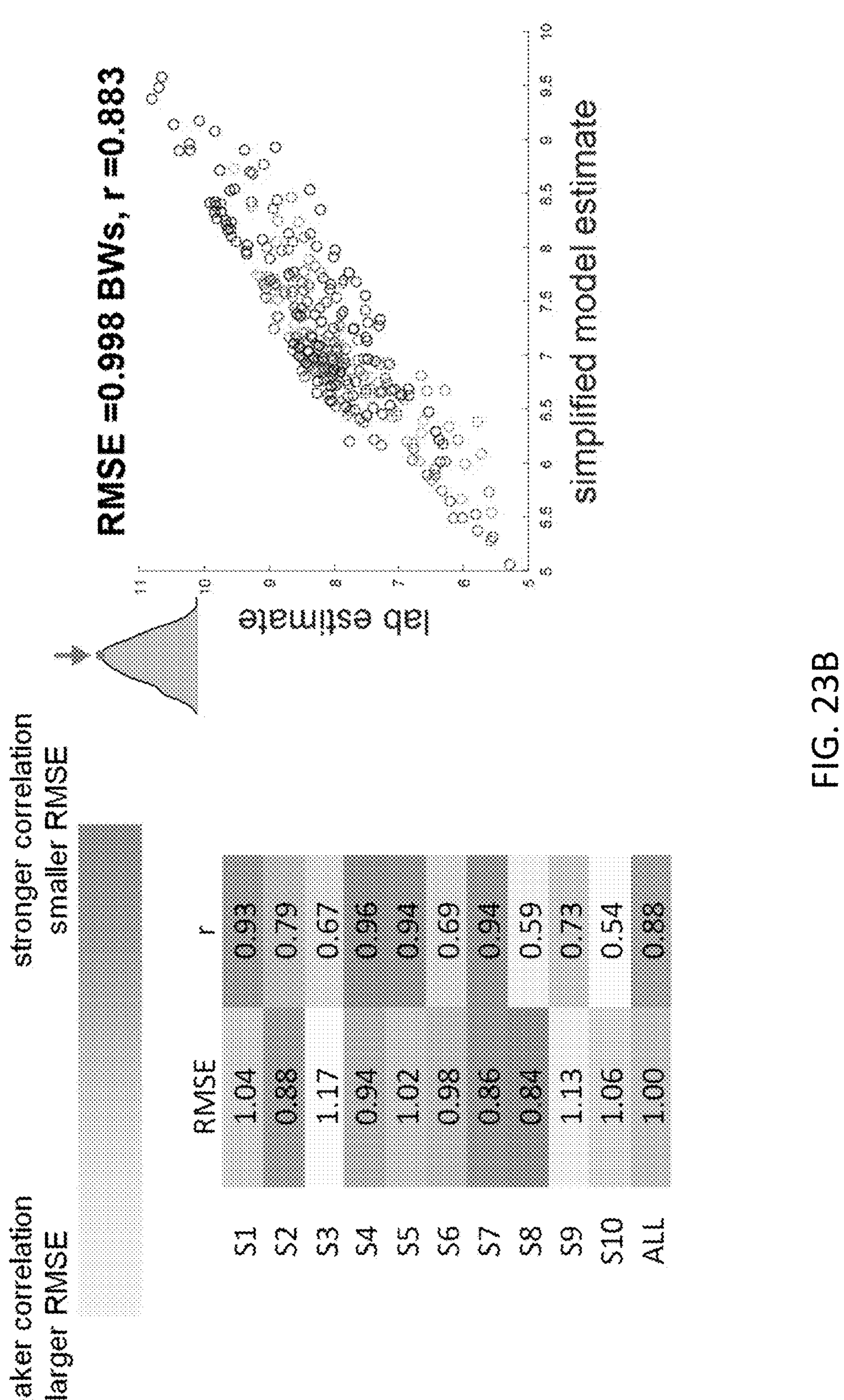
Figure 24A:
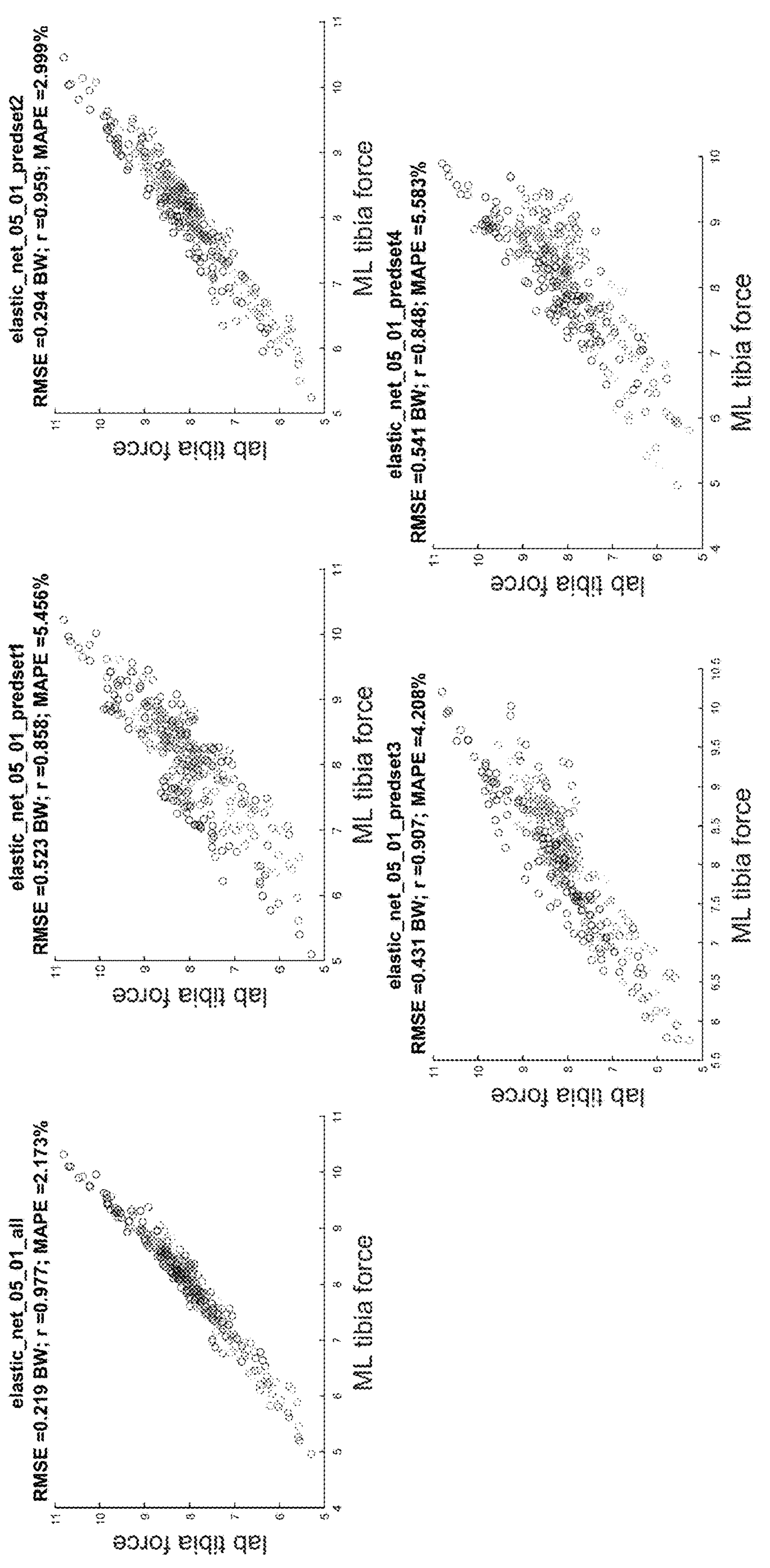
FIGS. 24A-24B show lab tibia forces and estimated tibia forces and their corrections processed using different machine learning under different conditions, according to embodiments of the invention.
Figure 24B:
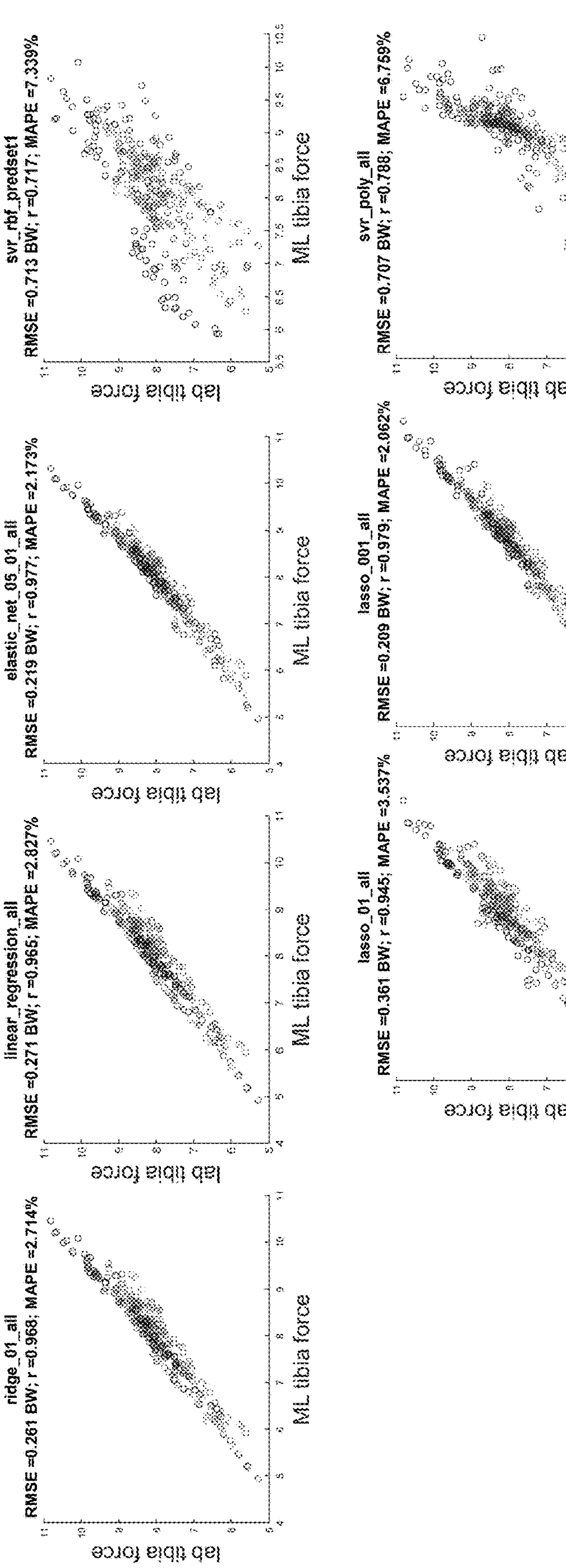

All trials: GRF metrics were moderately or weakly correlated to $F_{total}$ (FIG. 21). However, only the GRF active peak was positively correlated ($F_{active}$: I=0.64±0.26). Surprisingly, tibia bone force actually decreased with increases in GRF impact peak and loading rate ($F_{impact}$: r=−0.50±0.29; VALR: r=−0.53±0.28; FIG. 21). These preliminary results support our hypothesis. Increases in GRF metrics do not necessarily reflect increases in bone loading, signifying that GRFs alone may be of limited value in monitoring tibia loading or BSI risk. These findings complement prior evidence that higher impacts may not play a key role in the development of stress fractures.

Speed sweep: GRF metrics were strongly correlated to $F_{total}$ ($F_{active}$: r=0.86±0.11; $F_{impact}$: r=0.86±0.10; VALR: r=0.94±0.10) with increasing speed on level ground. However, $F_{total}$ was also strongly correlated to speed itself (r=0.91±0.10), which is generally easier to measure with wearable sensors.

Slopes sweep: $F_{active}$ had a range of correlations with $F_{total}$ (min r=−0.24; max r=0.99), while $F_{impact}$ and VALR were negatively correlated to $F_{total}$ ($F_{impact}$: r=−0.75±0.22; VALR: r=−0.78±0.18). $F_{active}$ had a range of correlations with slope itself (min r=−0.47; max r=0.95). Even with this small sample size, large variability in correlation values indicates GRF may not adequately capture subject-specific running strategies or estimate bone loading trends.

The exemplary results suggest that trends in GRFs are insufficient to track tibia bone loading. The most striking observation was that tibia loading tended to decrease with increasing GRF impact peaks and loading rates; though correlations were relatively weak. Additional or alternative measures may be needed to track tibia bone loading, with the long-term goal of predicting and preventing BSI risks.

Example 3

Wearables and Injury Prevention: Opportunities for Monitoring Musculoskeletal Loading In the results of EXAMPLE 2 indicates that GRF metrics are not strongly correlated with tibial bone forces across a range of running speeds and slopes. In this exemplary study, data from multiple wearable sensors on the foot and shank and a musculoskeletal model were used to better estimate loading on the tibia bone. An alternative solution was explored for monitoring bone forces: integrating kinematic and kinetic data from multiple wearable sensors with musculoskeletal modelling techniques to non-invasively estimate bone loading. Our preliminary feasibility assessment indicates this multi-sensor data fusion approach can outperform conventional GRF metrics, offering a promising solution for monitoring musculoskeletal forces unobtrusively in daily life.

Methods

Ten recreational runners each performed 30 running conditions, sweeping a range of speeds (2.6-4.0 m/s) and slopes (−9° to +9°). Lower-limb kinematics and GRFs were collected, and tibial compression force was estimated using an established model by Matijevich et al. 2019. First, we computed correlations between commonly-used vertical GRF metrics (impact peak, loading rate, active peak, impulse) and tibial force metrics (peak, impulse) across all conditions for each subject, then computed inter-subject averages. Next, to explore our alternative method for estimating tibial force outside the lab, we distilled lab-based data (i.e., force plate and motion capture data from EXAMPLE 1) into lower-fidelity simulated-wearable data (to approximate wearable sensor signals): Pressure-sensing insoles can estimate normal force and center of pressure (simulated by transforming 3D force plate data into 1D normal force data and transforming force plate center of pressure data into the foot's reference frame), and IMUs can estimate foot/shank orientations (simulated from segment kinematics from motion capture data). We used these data, with a modified musculoskeletal model, to generate a simulated-wearable tibial force estimate, and computed correlations vs. lab-based tibial force.

Results and Discussion

It is found that increases in vertical GRF metrics were not strongly correlated with increases in tibial force metrics (Table 10). Seventy-six of 80 subject-specific correlation coefficients exhibited r<0.8. These findings reinforce that commonly-used GRF metrics should not be assumed to be a surrogate for tibial force or injury risk. Simulated-wearable estimates of tibial force were, on average, strongly correlated to lab-based estimates (r>0.8, Table 10). These correlations were stronger than correlations between GRF metrics and tibia force. Fusing data from multiple wearable sensors with musculoskeletal modelling provides a feasible and promising solution for daily monitoring of tibial forces.

TABLE 10

Left: correlation coefficients (r) between lab-based and simulated-wearable estimates of tibial force metrics. Right: correlation coefficients between lab-based estimates of tibial force and vertical GRF metrics from the same subjects.

| correlation (r) | | simulated-wearable tibial force | | vertical GRF metrics | | | |
|---|---|---|---|---|---|---|---|
| avg ± std (N = 10) | | peak | impulse | impact peak | loading rate | active peak | impulse |
| lab-based tibial force | peak | 0.83 ± 0.47 | | −0.29 ± 0.37 | −0.20 ± 0.35 | 0.72 ± 0.42 | −0.46 ± 0.40 |
| | impulse | | 0.94 ± 0.55 | −0.51 ± 0.53 | −0.72 ± 0.41 | 0.03 ± 0.51 | −0.11 ± 0.41 |

GRF metrics like impact peaks or loading rates can be negatively correlated with bone force (Table 10), highlighting their potential to misinform interpretations related to bone loading and overuse injury risk. If running shoe developers aim to minimize injury risk, they may be interested in how shoe features affect forces on specific bones, muscles and tendons; and GRF metrics may be unreliable surrogates for evaluations. Similarly, wearable devices aiming to provide injury risk feedback may benefit from targeted monitoring of musculoskeletal loading, with less emphasis on GRFs. Our feasibility assessment using simulated-wearable data indicates that fusing data from multiple wearable sensors with a musculoskeletal model is a promising solution for daily monitoring of tibial forces.

Example 4

Wearable Device to Monitor Musculoskeletal Loading and Prevent Injuries

In this exemplary study, our short-term goal is to evaluate the feasibility of a game-changing new solution to monitor bone loading. We develop a novel integration of wearable sensors and biomechanical algorithms which could enable us, for the first time, to monitor injury risks due to bone loading, ecologically (i.e., in daily life), with the eventual goal of alerting users to excessive bone loading before injuries occur. This would empower users to modify their training to reduce injury risks. Our medium-term goal is to conduct a large-scale prospective study in which we would use the wearable to monitor bone loading on >100 runners on a daily basis (outside the lab) for >6 months. This would be the first ever prospective study of its kind to track both bone forces and injury outcomes in daily life. Such a study is currently impossible due to limitations in state-of-the-art tools. Our long-term vision is to keep runners fit, active and injury-free by developing wearable technology that can alert them when they are at elevated risk of injury, i.e., before an injury occurs and before the risks can even be perceived by the runner. We aim to achieve this vision through the development of a new type of smart wearable device (termed wearable) that could inform individuals on when and how to adjust their training, to reduce running-related injury risks and associated societal healthcare costs. Moreover, the wearable devices are expected to enable unprecedented, large-scale studies into risks and prevention of debilitating bone stress injuries.

The forces on your leg bones are primarily due to two things: the force between your foot and the ground (called the ground reaction force, or GRF), and force from your muscles contracting (which pull against your bones). Muscles are actually the larger of these two forces. In running, peak GRFs are 2-3 times body weight, but peak leg bone forces are 6-14 times body weight. This large difference is because of the high forces generated by your muscles.

Existing wearables use pressure-measuring insoles or accelerometers on the foot/shank/pelvis to estimate features of the GRF (e.g., peak force at foot impact). In our recent study (e.g., EXAMPLES 1-3), we showed experimental evidence that none of these GRF-related metrics are strongly correlated with bone force. This means increases in GRF (as measured by existing wearables) do not necessarily signify increases in bone force, or in stress fracture risk. In some cases, existing wearables even make completely wrong predictions (e.g., predicting bone forces decrease when they actually increase) which could be dangerous to runners who modify their training based on this feedback.

Our innovation breaks through limitations in the current state-of-the-art, using only tiny, low-power and lightweight sensors that integrate easily into socks/shoes, and fusing data from multiple wearable sensors on the foot/shank to estimate the two major components of total bone force: GRF and muscle forces (ligament and other forces are small for bones we monitor). The ingenuity of our approach is that we indirectly estimate calf muscle forces by combining (i) center-of-pressure data from pressure-insoles and provide a surrogate measure of GRF, with (ii) foot and shank orientation data derived from IMU sensors. This approach allows us to avoid using electromyography (EMG; electrical activity from muscles), which is a more common way to estimate muscle forces in the lab. However, EMG is notoriously noisy and fickle, it varies day-to-day, is generally unreliable as a force estimate as muscles fatigue, and is highly sensitive to sweat, electrode-skin contact and other factors outside lab. The wearable we are developing has the potential to be the first, and only device of its kind, to reliably monitor bone loading in daily life (by bypassing limitations of EMG and fusing data from multiple other sensors).

To explore the feasibility of this new wearable bone load monitoring system, a functional wearable prototype (portable sensing and data logging hardware) was developed, a benchmark data set was collected, from the wearable prototype and from high-fidelity lab-based sensors, and then, the (intra-day) accuracy and (inter-day) repeatability of the wearable bone load estimates vs. the lab-based (gold standard) estimate was characterized.

The wearable prototype was designed and integrated with off-the-shelf electronics. Then, a human subject data collection using a number of different measurement modalities was conducted. By applying laws of physics to estimate loading on ankle/foot bones, the data from lower-fidelity portable/wearable sensors were fused to provide accurate and repeatable estimates of loading on two bones (tibia, calcaneus) susceptible to stress fractures.

Wearable Device Hardware

Existing wearable devices being sold on the market now have either one IMU or one pressure insole, or one of each. In order for us to synchronously record data from a pressure-sensing insole and two IMUs (shank and foot), and to have access to the raw data, we create a portable data logging system (i.e., wearable prototype), which, in certain embodiments, includes a microprocessor board (Adafruit Featherlogger MO with microSD card writer for data logging), a 1200 mAh rechargeable lithium ion battery, a pressure-sensing shoe insole (IIE smart foot sensor, with 8 force sensing resistors over the plantar surface of the foot), and two 9-axis IMUs (Yost Labs 3-Space Nano). The IMUs is wired directly to the Adafruit microprocessor board, and the IIE smart foot sensor is connected to a small breakout board, then input to the Adafruit microprocessor board for data logging. The breakout board is a custom printed circuit board that we design and have printed by PCBgogo. The foot IMU and most electronics are enclosed in a 3D-printed box (which is worn on top of the shoe). The pressure insole is worn inside the shoe and shank IMU attached via velcro strap to the shank. The hardware (sensors) is adequate for estimating tibial and calcaneal bone forces.

In certain embodiments, a portable data logging system weighs less than 200 grams, i.e., about half the weight of many running shoes (a mass not expected to substantially alter running biomechanics). The system samples data at 100 Hz, which is sufficient for evaluating proof of concept based on our prior studies using wearable sensors.

Collection of Benchmark Data Set with Synchronized Lab-Based Equipment and Wearable Device In this exemplary study, recreational runners are recruited from the local community (half female). Inclusion criteria: adult (18 years or older), with no injuries or disabilities in the last 6 months that would limit their ability to run. To ensure subjects can safely and fully complete the breadth of trials, we only recruit individuals that self-report that they run at least 10 miles per week. Participants are consented on arrival to the lab, per approved IRB protocol #141697. A set of retro-reflective motion capture markers are affixed to their lower limbs, e.g., as shown in FIG. 4. The wearable prototype is also donned. Participants run on a treadmill at a range of speeds (+/−20% of their self-reported mile pace), step frequencies (+/−10% of their typical cadence) and slopes (9 degrees downhill to 9 degrees uphill) to simulate common running conditions. Once the participant's running technique has stabilized (per judgement of experimenter), 30-seconds of data will be collected. High-fidelity lab-based motion capture (Vicon, 100 Hz) and GRFs (Bertec, 2000 Hz) will be collected simultaneously, alongside lower-fidelity wearable prototype data (100 Hz, FIG. 3). EMGs from the soleus, gastrocnemius and tibialis anterior are also collected (as secondary data to include in publicly archived data set, but not used directly in our analysis). Trial order is randomized, with frequent rest breaks. Six participants are randomly selected to return for four more identical sessions to assess inter-day repeatability.

This is one of the largest and most complete sets of synchronized wearable sensor and motion lab data. Data are de-identified, curated (several post-processing steps that involve visual checks by experimenters to ensure data integrity) and then publicly archived on Zenodo to broadly benefit scientific/clinical communities. This is challenging because of the number of synchronized sensors. Alternatively, for a random subset of six subjects we also insert an additional research-grade pressure-sensing insole into the shoe. The difference is that foot smart sensor in the wearable prototype has 8 individual force sensors, whereas the research-grade insoles (Novel) contain 99 force sensors. The 8-sensor solution provides us with a lower-bound on how well inexpensive pressure insoles (about $100 per pair) can perform. The research-grade pressure insole provides an upper-bound on sensing performance. This reflects the fact that sensor hardware continues to get better (more accurate) and less expensive over time. Another challenge is related to synchronization. Nominally we use trigger (or analog) inputs/outputs to synchronize signals between various sensors (e.g., wearable vs. lab-based). In some cases, this can become complicated due to available inputs/outputs, and we use a cross-correlation script to match up peaks and synchronize signals post hoc. In either case, we perform and document validation/characterization steps leading up the experiment to ensure signals are all tightly and properly synced.

Quantification of Accuracy and Repeatability of Bone Force Estimates from Wearable Device In certain embodiment, the wearable device estimates tibial bone force with root mean square error (RMSE) <10% of peak bone force during running, both within- and between-days. In certain embodiment, inverse dynamics and musculoskeletal modeling algorithms are applied to the lab-based motion analysis and GRF data to estimate the total compressive forces on the tibial and calcancus bones, similar to estimates shown in FIG. 4. These lab-based force estimates serve as a well-validated gold standard, i.e., the best non-invasive estimate of bone loading. We then combine statistical modeling (regression and sensor fusion approaches) with biomechanical algorithms (physics-based equations of motion for musculoskeletal system) to estimate tibial and calcancal bone forces from the wearable sensors (FIG. 2A). The general algorithm used is shown in FIG. 2B. Note that pressure sensor data are summed to provide an estimate of GRF, and a weighted sum of each force sensor is used to estimate spatial center of pressure under the foot. IMUs provide an estimate of angular orientation, by using double integration Kalman filtering methods; implemented using the Inertial Sensor Fusion package in Matlab. FIG. 2A shows a graphical representation of the physics force balance equation about the ankle joint, and reflects how to estimate compressive force on the tibia bone. The calcaneus bone force estimate is nearly identical, except the GRF component is removed from this estimate when the heel lifts off the ground.

A key thing to highlight is that the wearable sensors are not able to measure all the necessary terms in the true/full physics force balance equation. For instance, in the full physics equation there is a 3D force vector input from the GRF, which can be measured in lab, but the wearable sensors can only estimate a 1D force vector (normal to the foot) by summing across all of the pressure sensors. For this reason, we use statistical modeling approaches, i.e., by adding unknown variables into the equation for quantities that we are unable to measure with wearable sensors, then solving for these unknowns using regression algorithms. To accomplish this we must add one additional calibration stage into our workflow, which allows us to estimate the unknown variables using the empirical data we collect. The nominal way to address this is to apply a simple least squares regression fit to the entire data set (across all running conditions for a single subject) to simultaneously solve for all the unknown variables.

Alternatively, this calibration is refines and optimized, and wearable algorithms are optimized and generalized at the same time as assessing initial feasibility. Note that all analyses are done on a subject-specific basis, to avoid confounds due to subject-specific characteristics (e.g., height, weight, running style, etc.) and to avoid critical issues related to group-to-individual generalizability. The subject-specific analysis provides the best opportunity to explore feasibility of our novel solution, and to understand whether RSME (between wearable and lab-based estimates) are <10% for most or all subjects.

We compare the wearable bone force estimates vs. well-validated lab-based estimates of bone force (gold standard). The primary outcome to assess accuracy/repeatability is RMSE in peak force. Peak force was selected because of its ability to induce mechanical fatigue of bone, which can result in stress fracture onset via microdamage accumulation. We hypothesize RMSE <10%.

If the RMSE accuracy is >10% then we explore different ways to calibrate, or refine the form of the physics-based algorithm. For instance, we sub-divide the data from each subject into a training and testing set, then explore variants of the equation to help improve the accuracy. An example is using a combination of the summed force from the pressure insole, and the angle orientation of the shank to more directly estimate the fore-aft GRF (rather than rely on the regression to solve for this unknown). Alternatively, we use more sophisticated machine learning algorithms (e.g., using a deep neural network). If day-to-day repeatability is poor, then we develop a supplementary calibration algorithm to minimize inter-day differences.

In sum, this exemplary study provides a novel way to address the challenge of bone load monitoring via wearable sensors, which represents a critical barrier to monitoring bone stress injury risks in daily life. Overcoming this barrier enables us to deepen our scientific and clinical understanding of how to identify heightened risk and ultimately prevent injury. In certain embodiments, the wearable device has wireless data transmission (e.g., via Bluetooth) in communicating with a smartphone app to visualize the data tracked. In addition, the wearable device is also able to log additional data/information that is already available from consumer devices, e.g., using an activity tracker to monitor hours of sleep each day, or the rest time in between heavy bouts of physical activity. Further, the long-term solution would likely also benefit from knowledge of factors like age, gender, height, weight or other health info. The bone load monitoring is the critical new component that would enable a huge leap in capabilities, to further enhance insights and help identify when individuals are at heightened risk for overuse injury such as bone stress fractures; so these risks can be mitigated before injury occurs.

Example 5

Prevent Bone Stress Injuries (BSI) by Using Wearable Sensors to Monitor Bone Loading BSI occur due to repetitive and/or prolonged forces on bone, resulting in microtrauma. BSI are preventable if these overloading forces can be identified early and intervention applied. Currently, early detection or monitoring of bone loading can only be done in a motion analysis lab, using musculoskeletal biomechanical analyses. Unfortunately, regular screening of individuals with motion laboratory analysis would be time-consuming, expensive, and impractical.

In this example, by utilizing wearable sensors to real-time monitor bone loading in athletes or others, unhealthy loading conditions leading to overuse injuries are identified, so as to enable medical professionals to intervene before BSI occur.

Given the recent advances in sensors and biomechanical knowledge, the opportunity exists to use wearable sensors to create a practical monitoring solution. There are many examples of portable sensors embedded into apparel (e.g. clothing, shoes, and watches) that capture motion, force, and biometric data. Now the knowledge gap is selecting the set of sensors, and algorithms, necessary to create reliable estimates of bone loading. In certain embodiments, to bridge this gap, the accuracy of combinations of wearable sensors is characterized against gold standard measurements; the minimum set of wearable sensors that can provide a reliable estimate of bone loading is determined, and a wearable and functional device is developed. This study focuses on monitoring forces on the tibia, the most common site of BSI in athletes. The methods and sensing technology outlined here are generalizable to other bones.

Determination of Optimal Set of Wearable Sensors to Track Tibia Loading

Figure 3:
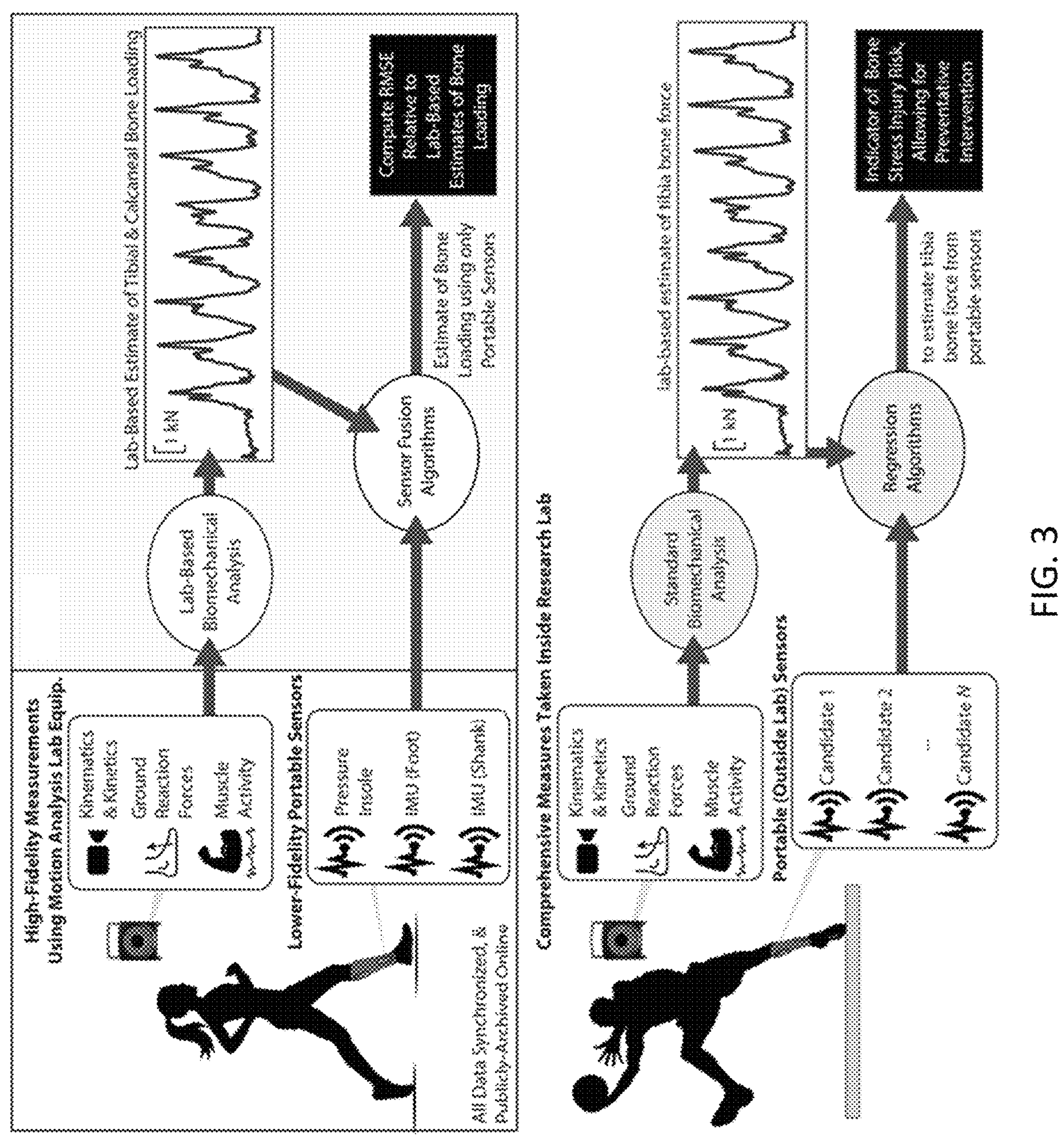
FIG. 3 shows experimental protocol and analysis according to embodiments of the invention, which seeks to identify the minimum set of wearable sensors.

Biomechanical data collected in a computerized motion analysis laboratory can estimate tibia loading; however, (i) there are currently no validated algorithms that can estimate bone loading outside of the lab with wearable sensors, and (ii) it is not known which types of wearable sensors are actually needed to estimate bone loading. To identify the optimal set of sensors and associated sensor fusion algorithms to estimate tibia forces during basketball-specific tasks (e.g., running, jumping, and cutting). In certain embodiments, a human subject biomechanics experiment in which high-fidelity lab-based measurements and lower-fidelity wearable sensor data are simultaneously collected (FIG. 3). Two main categories of sensor (i) motion/orientation and (ii) force/muscle are identified. Motion/orientation sensors provide information about limb segment angle and serve as a surrogate for motion capture cameras. Force/muscle sensors provide information about loading magnitude and serve as a surrogate for force plate and high-fidelity EMG in lab.

Subjects: Approval for all procedures is obtained from the Vanderbilt University/Vanderbilt University Medical Center Institutional Review Board. Using standard procedures within the Vanderbilt Department of Orthopedics research office, we recruit 20 participants. Inclusion criteria are a minimum age of 16, a minimum of two years of participation in an organized basketball league with a minimum of one season per year, no history of bone stress injury (reaction or fracture) or lower extremity surgery in the previous two years, with a history of participating in organized basketball over the previous two years. Additional exclusion criteria include a history of cardiovascular disease, growth disorders, oligomenorrhea, and amenorrhea.

Facilities/Resources: Human subject studies occur in the Vanderbilt University Center for Rehabilitation Engineering and Assistive Technology. The Center contains a motion analysis lab with six-axis in-ground AMTI force plates, Bertec split-belt instrumented treadmill, 10-camera Vicon T40 motion capture system, 16-channel wireless Delsys Trigno EMG, and all other sensors required for this research.

Experiment: We collect data from high-fidelity lab-based measurement systems, and then employ well-established biomechanical analyses to non-invasively estimate bone loading from these data. We simultaneously collect data from a suite of synchronized, calibrated portable sensors. Regression analysis techniques (detailed below) then is applied to these wearable data to identify the minimum set of these sensors needed to reliably estimate tibia loading. Synchronized high-fidelity (lab-based) and lower-fidelity (portable) sensor data will be made publicly available for other researchers to train or evaluate their own sensor fusion algorithms.

Basketball Tasks: Subjects perform tasks relevant to basketball, including running, decelerating, single leg jumping, double leg jumping, double leg landing, and cutting while responding to simulated shooting, rebounding, and defensive cutting movements. Examiners will collect data from each subject completing these tasks in a single session. To reduce the risk of bias, the examiners will randomize the order of the tasks. Each task is completed 20 times in a single collection period for each lower extremity of interest in order to collect sufficient data for statistical analysis.

Wearable Sensors: In this example, the following set of wearable sensors is used to collect data from each participant: (1) 3-axis accelerometers with bipolar surface EMG electrodes (Delsys Trigno), (2) 6-axis inertial measurement unit (Xsens), (3) pressure-measuring insole (Novel Pedar-x), (4) pressure-sensing fabric (Sensor Edge), and (5) strain gages (Spectra Symbol Flex sensor 2.2). Just as in the motion analysis lab, no single sensor can estimate tibia forces, but rather fusing data from multiple sensors estimates bone loads.

Lab-Based Data Analysis: High-precision lab-based measurements (motion capture, force plates, and multi-channel EMG) are analyzed to provide a non-invasive estimate of bone loading at the distal end of the tibia. A well-established EMG-assisted modeling approach is employed to estimate total force on the distal end of the tibia (near ankle). Estimation methods are implemented using a combination of software packages (Vicon Nexus, Visual3D, MATLAB and OpenSim).

Mapping from Portable to Lab-Based Bone Force Estimates: Regression analyses (linear and non-linear) is employed to identify how to use portable sensor data to approximate lab-based estimates of tibia force. Data from all trials are appended together prior to regression. Multiple regression analysis using least squares is performed for each subset combination of candidate sensors (i.e., N factorial combinations for N sensors). The result is an algorithm (coefficients) that utilize portable sensor data to estimate tibia loading.

Bone Force Estimation from Portable Sensors: Regression coefficients from each aforementioned analysis are used to estimate tibia forces. Then the RMSE of the predicted force of the wearable vs. lab-based sensors is computed across all trials. Each combination and regression formulation is compared against a one body weight RMSE threshold, where peak bone forces are approximately 10 times of the body weight. The optimal set of portable sensors is defined as the minimum number of sensors that yield average RMSE across all trials<1 body weight. If no sensor combination yields RMSE<1 body weight, then the algorithm that yields the lowest RMSE Statistical Analysis and Sample Size: For each combination of wearable sensors, we calculate the RMSE vs. the laboratory sensors. We perform this comparison both over the entire time course of each exercise as well as for the set of peak forces to ensure that the sensors hit our target performance for the entire range of forces and at the critical peak loading values. The study includes n=20 participants, and we assume one-sided type I error rate of 10% and state a target RMSE of 1 body weight. We use a chi-square test and calculate that a true RMSE of 0.5 body weight (5% of peak forces) gives our study a power of 99%. The power value shows high feasibility in finding agreement between the sensor sets for the entire time course data as well as the peak force subset.

The benchmark data set with synchronized portable sensor and motion lab data, is made publically available via Zenodo online data repository, and the minimum set of sensors capable of estimating tibia loads with desired accuracy (RMSE<1 Body weight) is determined.

The key challenges are related to our ability to (1) simultaneously record and (2) integrate large amounts of biomechanical data. Alternative approaches include exploration of additional sensor fusion algorithms (e.g., Kalman filter, machine learning). In our analyses, some level of individualization may be necessary. For example, in practice, users may need to perform a few person-specific calibration trials (particularly if a signal like EMG is used). Such calibrations are quick, easy, and common with many commercial electronic devices (e.g., smart phones, Wii video game).

Integration of Sensors and Algorithms into Wearable Device for Validation Testing To develop and validate an instrumented leg compression sleeve prototype that can monitor tibia bone loading outside of the lab, we design a prototype wearable device based on the minimum set of sensors and validate its ability to estimate tibia loading as compared to the gold standard laboratory sensors, as well as to obtain subjective feedback from basketball players on the comfort and obtrusiveness of this new wearable technology. Similar to how wristwatches have been transformed into activity monitors to promote better health and well-being, this research contributes to the development of wearable technologies to reliably monitor bone loading outside the lab.

Subjects and User Input: The same subject population is given a survey during the initial participant force analysis visit to collect input on the features and design requirements, and is recruited to perform the set of motions while wearing the developed prototype.

Prototyping: Using both off-the-shelf and in-house fabricated components and materials, three prototypes is created: (1) form, (2) function, and (3) user experience (UX). We are able to simplify the prototyping process by untethering aesthetics, functionality, and use, allowing for a parallelization of prototype construction, evaluation, and revision.

Form: Construction of this prototype involves the procurement of material samples used in compression garments with a variety of stretch content. During a participant's force analysis visit, we obtain lower leg measurements to establish patterns and fabric preferences. Using these patterns and material preferences, we fabricate “looks like” prototypes.

Function: we show proof-of-concept (POC) for a multi-sensor setup containing several candidate sensors including both rigid and flexible versions. Once the minimal sensor set from Aim 1 is available, we modify the POC with flexible sensors (i.e., strain gauges and pressure sensors). All sensors will be tested verifying data transmission through wireless connectivity, consistency with the results of Aim 1, and the sensor fusion algorithms modified if needed.

UX: This prototype is tailored to the users' needs and features collected from participant surveys during the first visit.

Revision and Finalizing Design: User feedback on the form, function, and UX prototypes will be used to revise each prototype. Conflicting user input will be evaluated through the execution and testing of parallel versions. Certain design requirements and desired features may be prioritized over others based on user feedback, feasibility, and scope of the project. For instance, participants may indicate a desire for the integration of sensor data with other fitness apps; however, a software platform is outside the scope of this project. The final prototype will be evaluated for its ability to meet the prioritized design requirements and desired features.

Statistical Analysis and Sample Size: To validate the hardware prototype, we conduct a study on a population of 20 basketball athletes. Participants are asked to wear the wearable device prototype while performing the same set of motions. Data are processed and analyzed using the sensor fusion algorithms, and a similar statistical approach is used to validate the final wearable prototype against the laboratory sensors.

Limitations include the ability of the sensors to precisely and accurately capture data as a result of the motion of the participant, sweat, motion of the skin relative to the muscle and bone, and sensor disconnection from the skin. Additionally, while we imagine a lightweight, minimal device, we realize component limitations may prevent our final consolidated prototype from achieving the desired specifications. Depending on the ultimate set of minimal sensors, sensor locations need to be optimized and perhaps even spread to multiple locations for ideal function. This may result in a larger device or one that requires multiple locations.

Briefly, the exemplary approach combines wearable technology and biomechanical knowledge. The lightweight, form-fitting, and unobtrusive wearable sensing system can monitor bone loading and thereby help protect against BSI in NBA players and the general public. In certain embodiments, the wearable system is similar to leg garments that athletes already wear during practice, encourages prospective research on BSI, provides athletes/athletic trainers/coaches/doctors with real-time cues that encourage safer sports technique, generate vast public health data that can inform evidence-based clinical and workplace practices, and potentially reduces the societal costs associated with BSI (e.g., health care and missed work).

Example 6

Cyber-Physically Assistive Clothing for Monitoring Low Back Loading and Providing Direct Assistance The objective of this study is to address core scientific challenges related to sensing, actuation and control of cyber-physically assistive clothing (CPAC). CPAC is a kind of Human-in-the-loop Cyber-Physical System (HCPS), in which actuated clothing is coordinated in unison with human body movement to enhance safety and health. This study addresses key HCPS challenges within the context of using CPAC to reduce societal incidence of low back pain, by preventing lumbar (spine) overloading and overuse injuries.

Low back pain is targeted because it is one of the leading causes of physical disability and missed work. The etiology of low back pain is multifactorial, but major risk factors that occur during daily activities are high and/or repetitive forces on lumbar muscles and discs. The long-term vision is to create smart clothing that can monitor lumbar loading, train safe movement patterns, and directly assist wearers to reduce forces that can cause injury. This transformation of clothing is similar to how wristwatches have transformed from timepieces into health monitors; however, CPAC is even more promising because garments can be embedded with active (or quasi-passive) structures that reduce biological tissue loading for a range of populations, occupations and tasks.

In one embodiment, machine learning techniques are adapted in order to monitor lumbar loading and identify unhealthy movement patterns via portable, wearable sensors, such that timely feedback/intervention can be provided. This results in the creation of a publicly shared data set that contains synchronized, multimodal (lab-based and wearable) sensor data collected from >500 actions per subject, the largest such corpus for machine learning in this domain. In another embodiment, the dynamics of cyber, physical and human components of CPAC are modeled in order to develop optimal control and learning strategies. In yet another embodiment, sensors, fusion algorithms and portable actuation are integrated into a wearable prototype. Human subject testing is performed to evaluate the benefits of CPAC on low back loading during leaning and lifting tasks.

This study integrates expertise in biomechanics, machine learning, sensor fusion, soft robotics, wearable assistive technology, and clinical management of low back pain to transform clothing from materials that cover the body into wearable systems that can track and protect low back health. The key HCPS challenges that need to be overcome, and which are addressed in this study, in order to realize the broad societal benefits of CPAC are: (1) real-time sensing and assistive control of the HCPS and its co-adaptation to different subjects and diverse environments, (2) system design and verification ensuring safe operation and that no harm is done to human subjects through unanticipated feedback, (3) selection and placement of low cost sensors aiding affordable and realistic manufacturing of CPAC, (4) integration of wearable sensors and actuators into a reliable and effective HCPS.

This innovative and preventative approach has the potential for broad societal impact given the high prevalence of low back pain. Much of this pain could be prevented or mitigated if unhealthy loading of the spine is reduced, but this requires a wearable device that seamlessly integrates sensor fusion algorithms and physically-assistive components. CPAC provides a unique and potentially paradigm-shifting opportunity because clothing is ubiquitous, worn every day, and when designed properly it is lightweight and unobtrusive. CPAC is expected to (1) fit seamlessly into a person's daily life, (2) connect individuals with health information to empower them to modify their own physical activity, (3) generate public health data that can inform evidence-based clinical and workplace practices, (4) directly augment leaning and lifting biomechanics to reduce lumbar loading, (5) reduce the incidence of low back pain, and thus costs associated with health care and missed work, and (6) leverage existing soft goods manufacturing methods to enable a scalable and affordable solution.

In certain embodiments, a lightweight, form-fitting, low-power, wearable garment is disclosed, which helps protect low back muscles and spinal discs from overloading and overuse, and serves to both monitor low back loading (to identify injury risks and enable on-line warning or timely interventions), and provide direct assistance (to off-load spinal tissues). CPAC works in unison with the user's movement, to offload the low back muscles and intervertebral discs during leaning and lifting tasks to help reduce force-induced low back injury and pain risks. The dark red structure of the CPAC provides an external load path, which mitigates forces on muscles and discs, to help prevent disc herniation and other injuries.

Although passive wearable devices have been shown to have substantial promise in reducing spinal loads during lifting tasks, they are limited in their ability to adapt to different tasks. Specifically, most realistic tasks involve multiple movements, some of which might be loaded, while others are unloaded. For example, lifting an object from one location and depositing it in another requires at least four simple motions, each of which have differing characteristics. If well-designed, a passive device is able to reduce spinal loading for one of these four states, but in general will exacerbate loading in the other states.

The inability of passive devices to adapt to varying conditions can be addressed by employing active or semi-active wearable devices. Such devices can sense the characteristics required of a given activity, and can provide appropriate assistance in each case. Although considerable effort has been invested in the development and control of exoskeletons, relatively little effort has been directed towards the development of active or semi-active wearable devices for reducing spine loading.

Active exoskeleton control requires two primary control layers. Because an active exoskeleton has the ability to adapt its functionality to a specific task, it must recognize which task is being performed in order to provide the appropriate control functionality. This level of control is often referred to as intent recognition. Once the exoskeleton recognizes the type of task being performed, a coordination processing unit must coordinate the movement of the exoskeleton with the movement of the person wearing it. In an effort to provide an effective and realistic intent recognizer for a back exoskeleton muscles combined with inertial measurements of the trunk in an LDA-based pattern recognition algorithm is used to obtain real-time identification of trunk flexion, trunk extension, and upright posture.

The single most important measure for purposes of effectively controlling an exoskeleton to reduce spine loading is the spinal load. Although this cannot be measured directly in a non-invasive manner, we propose here to develop a real-time observer to monitor it. To our knowledge, no other research group has developed such a spinal load observer, particularly one that employs a minimal set of wearable sensors. As such, we propose to first perform a set of experiments employing a laboratory set of instrumentation that will provide a level of ground truth regarding spinal loads during various tasks. From that data, we extract the minimal set of wearable sensors that will provide sufficiently accurate real-time estimates of spinal loads. Based on the resulting real-time observer, we develop control methods for CPAC intended to reduce spinal loading during lifting tasks. After design and realization of this prototype, we again employ laboratory instrumentation to assess the efficacy of the system in reducing spinal loading during lifting tasks.

Lumbar Loading Estimation

In one embodiment, machine learning techniques are adapted in order to monitor lumbar loading and identify unhealthy movement patterns via portable, wearable sensors, such that timely feedback/intervention can be provided. This results in the creation of a publicly shared dataset that contains synchronized, multimodal (high-fidelity lab-based and lower-fidelity wearable) sensor data collected from >500 actions per subject, the largest such corpus for machine learning in this domain.

A. Experimental Design

A set of candidate/potential portable sensors are identified based on the published biomechanics literature, our own preliminary studies and our interviews with potential end users. Portable sensors are not as accurate or comprehensive as in-laboratory research-grade measurement systems; however, the portable sensors can potentially serve as wearable surrogates for these in-lab measures. Two main categories of sensor were identified: (i) motion/orientation and (ii) force/muscle. Motion/orientation sensors provide information about lumbar angle, and thus serve as a surrogate for motion capture cameras (which are impractical outside of the laboratory). These sensors include: (a) inertial measurement units (IMUs, combining accelerometers and gyroscopes) that could be placed on the trunk and pelvis (using the difference in angle to estimate the configuration of the local lumbar spine), (b) flex sensor adhered to the skin to estimate localized lumbar orientation (i.e., lordosis vs. kyphosis). Force/muscle sensors provide information about the level of loading itself, and serve as a surrogate for force plate and high-fidelity electromyography recordings in lab. These sensors include: (c) pressure or force sensors (e.g., inside the shoe to estimate forces applied to the ground), (d) pressure-sensing fabric (e.g., along the buttocks to measure forces during sitting), (e) surface EMG electrodes placed on lumbar or abdominal muscles to quantify activation.

A comprehensive motion analysis study is performed on 20 healthy human subjects to evaluate the ability of wearable sensor data to estimate low back loading during a range of tasks, similar to commonly experienced physical demands in daily life. Subject inclusion criteria: adult (>18 years old), with no history of back pain within 6 months, and no other disabilities or impairments that would confound their ability to complete locomotor tasks. Example tasks include: static leaning at 30, 60 and 90 degrees (standing and seated), dynamic lifting of a 10 and 25 kg weight up to 1 meter height (standing and sitting), sitting with both good and bad posture (based on OSHA guidelines), laying on one's back and side, and walking on level, uphill (6 degrees) and downhill (−6 degrees) grades at 0.8 (slow), 1.2 (moderate) and 1.6 m/s (fast) speeds. A total of 500 such tasks will be tested (too many to comprehensively list), where each task is defined by an activity (e.g., leaning, walking, turning), a direction (e.g., forward, to the right), and a magnitude (e.g., trunk lean angle, gait speed). Tasks randomly appear on a visual display (image or video of the task), informing the person to complete said task. Each discrete task take <10 seconds, and most will take <5 seconds. Once complete, the next task appear. Subjects get rest breaks every 5 to 10 minutes. All tasks are performed within the 15×15 foot motion camera capture volume in the lab, which contains a suite of high-precision laboratory-based measurement systems (motion capture, force plates, force-instrumented treadmill, and multi-channel electromyography) and apparatus (e.g., treadmill, stairs). Lab-based data will be analyzed post-hoc to provide a non-invasive estimate of internal lumbar loading. Raw data collected are de-identified and made publicly available on an online open source data repository (e.g., Zenodo).

The following candidate portable sensors are worn and track data simultaneously (and synchronously with other motion capture modalities): (1) Delsys Trigno sensors, which contain 3-axis accelerometers (37×26×15 mm, 16-bit, 2000 Hz sampling, Boston, MA) and bipolar surface EMG electrodes. At minimum, two will be placed on primary low back extensor muscles (right/left erector spinae) and two on the primary flexor muscles (right/left rectus abdominus). (2) Xsens sensors (36×25×10 mm, 10 g, 1000 Hz, Enschede, Netherlands) with 6-axis IMU will be placed midline along the back, at spinal levels L5, T8 and C8, and bilaterally on each thigh, shank and foot. (3) Novel Pedar-x pressure-measuring insole (400 g, 256 individual sensors, 2000 Hz, Munich, Germany) worn in both shoes. (4) Sensor Edge (Parsippany, NJ) pressure-sensing fabric worn on/behind the buttocks. (5) Spectra Symbol Flex sensor 2.2 (Salt Lake City, UT) placed on the skin above the lumbar spine, directed axially along the spine, left of the Xsens sensor.

A well-established EMG-assisted modeling approach is employed to estimate compressive, shear and total (magnitude of) force at the L5/S1 spinal level. Complete methodological details are implemented using a combination of software packages (Vicon Nexus, Visual3D, MATLAB and OpenSim). This EMG-assisted approach, which is nearly identical to the approach we implemented in our recent study on walking biomechanics, is complex in its details (due to 3D geometries, EMG-to-force mapping, electromechanical delays, etc.), but conceptually is relatively simple to summarize in 4 parts: (1) Standard rigid body inverse dynamics analysis is performed to estimate net 3D lumbar moments and net force ($F_{net}$). (2) Next, an EMG-to-force mapping algorithm is used to estimate individual lumbar and abdominal muscle forces ($F_{muscle\text{-}unscaled}$). Since there are more muscles than EMG signals recorded, anatomically or functionally similar muscles are assumed to have the same activation pattern; a commonly-used and well supported assumption for the lumbar musculature [20]. (3) Optimization is performed to correct/adjust individual muscle forces (yielding $F_{muscle}$) and to estimate ligament forces ($F_{ligament}$), such that these dynamics satisfy all 3 moment equilibrium constraints (from inverse dynamics). The cost function attempts to minimize muscle force corrections and constrains muscles to provide non-negative forces (i.e., allowing them to pull but not push). (4) The resultant internal forces on the lumbar spine ($F_{contact}$) can then be computed by summing the net forces and forces due to muscles and ligaments. The magnitude of force at L5/S1 ($F_{contact}$) will be used as the primary outcome, which portable sensor estimates will be compared against. Additional notes: For each participant, a set of calibration trials (flexing/extending low back against a load cell) is performed at the beginning of each study to determine EMG-to-force scaling factors.

B. Lumbar Load Estimation from Wearable Sensors

In certain embodiments, the machine learning is performed on the synchronized, multimodal (lab-based and wearable) sensor data to identify those sensor sources that can be used out-of-lab for lumbar load estimation. As explained before, the lumbar loading can be reliably calculated from the high fidelity lab-based sensor data, and our goal is to estimate it from the possibly lower-fidelity wearable sensor data. We employ more wearable sensors than we expect to be strictly necessary, so we select a subset of the wearable sensors (feature selection) and then perform estimation (regression) of the lumbar load based on the selected features. There are many machine learning techniques both for feature selection and for regression. For feature selection, we plan to use (1) filter methods: when the relevance of features is estimated using mutual information, correlation or backward selection, (2) wrapper methods: when several models are trained for various random subsets of features and the number of selected features is gradually decreased, and (3) regularization methods: where the Lo, $L_1$, L2 norm of the weights within the model, or some linear combination of these, is minimized during a single training session. For regression (the estimation of the lumbar load based on the selected features) we plan to use (1) deep neural networks with fully connected layers and (2) Bayesian models based on modelling the low fidelity signals and the lumbar load from the high fidelity ones, and estimating the a priori distribution for the high fidelity signals and calculating the a posteriori distribution for the lumbar load. We use both static regression models, using a single set of sensor data for a given time instance, and dynamic ones, when data collected during a time window is considered as input to the model. Knowledge gained on how to estimate loads from portable sensors is generalizable to other application (beyond low back health) and other types of assistive or rehabilitative exoskeletons.

The research is carried out in the state-of-the-art Motion Analysis Lab in the Center for Rehabilitation Engineering and Assistive Technology of Vanderbilt University, which has the measurement infrastructure to record synchronized signals from all of the aforementioned systems, nearly all of which are currently being used in the lab for ongoing research projects. Bayesian models might be very computationally expensive to fully evaluate for several selection of features limiting it to filter based feature selection methods.

In terms of alternative approaches, there are many additional sensor fusion approaches that may be valuable to explore (secondarily to the primary regression analyses outlined), such as Kalman filter approaches. In our analyses, some level of individualization may be necessary for the classification of forces. For example, in practice people may need to perform a few person-specific calibration trials (particularly if a signal like EMG is used, which can vary day-to-day based on skin or other physiological conditions). Adding a brief calibration period prior to experimentation (if needed) is not a problem, and such calibrations are even common with many commercial electronic devices (e.g., smart phones, Wii video game), so this possibility is not considered impractical in the lab or problematic long-term.

C. Limitations and Assumptions

This research aims to address reduce risk of low back injury and pain amongst the general public due to excessive loading, but this approach does not address all causes of low back pain. Low back pain can also result from other etiologies, some of which are neurogenic, psychological, environmental (e.g., stress), congenital or acquired spinal stenosis. Experimentally, we employ comprehensive biomechanical analysis techniques, but all methods employed are non-invasive. In reality, this is currently no direct way to validate muscle forces in vivo (as this would require us to implant load sensors in series with every single muscle and ligament). However, strong evidence have been put forth demonstrating validity of EMG-assisted model estimates, specifically: (i) the strong correlation of muscle force estimates with EMG, (ii) that results are constrained by inverse dynamics (i.e., consistent with the laws of physics, in terms of net moments and forces), and (iii) that EMG-assisted results have been tested and validated under controlled conditions that support epidemiological findings. Collectively these give us confidence in lab-based estimates. Of critical note: the success of CPAC and the success of these research studies does not depend on ultrahigh accuracy force estimates (for the same reason that pedometers did not initially need to be super high-accuracy) in order to provide useful feedback to users (though accuracy has improved over time due to advances in sensing and algorithms). Despite limitations of non-invasive lumbar load estimates, we contend that the analyses used are sufficiently-well established and validated to yield lumbar force estimates for our purposes. Future investigations may assess risk in a more sophisticated way; for instance, by tracking both lumbar force and angle together (since the spine can handle higher forces when at neutral configuration), or one could track loading history (e.g., number rather than magnitude of high load instances, which may indicate disc herniation risk). Finally, a subset of representative tasks were selected to capture the dynamics of common daily tasks It is impractical/impossible to test every conceivable daily activity, but this is not crucial so long as a rich variety of tasks are included for machine learning, which induce various levels of loading. Very high loading tasks (eg >3500 N) are not be tested for safety reasons, but algorithms developed in this work are still expected to extend to these higher loads.

Assistive Control of HCPS

We model the dynamics of cyber, physical and human components of CPAC jointly combining traditional discrete, continuous and stochastic models and machine learning techniques. We capture the full behavior of the CPAC system, including the human response to active and quasi-passive assistance, and develop optimal control and learning strategies.

A. Experimental Design

This study explore multiple control algorithms and assess the degree to which individuals change their movement behavior over time. In order to understand both immediate effects of the assistance, and if or how users change their behavior over time with powered assistance, the testing focuses specifically on a smaller subset of tasks: forward leaning and lifting (of different weights). Data from both lab-based and portable sensors are collected to capture the full kinematic and kinetic behavior of the CPAC system (i.e., human and device). Again, this unique data set is made publicly available, for others in the CPS community to use for developing and refining their own inference and control algorithms.

Human subject experiments are performed using a Humotech universal device emulator (off-board motor and controller) to actuate a CPAC prototype. This actuation hardware will be setup and available for testing before the start of this project, enabling Thrust 2 focus to be on understanding control and human biomechanical response, without the need for additional hardware development. All sensor data will be fed back to a SpeedGoat Performance Real-time Target Machine. Baseline controller code will be developed in Simulink and downloaded onto the same SpeedGoat machine for implementation.

Safety notes: all pulling forces is <1000 N, which is far below forces typically generated by a person's biological muscles. The shear pressures experienced by the skin at these force magnitudes is substantially less than the threshold at which skin becomes injured (approx. 54 KPa). All loading applied is distributed over sufficient skin area such that average stress is always less than 25% of this magnitude. An internal breakaway tether in the emulator system prevents undesired high loads from being transmitted to the person.

Data are analyzed in a similar fashion above, except now including externally applied forces from the device into the biomechanical model. Algorithmically, this analysis is identical to the method; however, with the introduction of external forces from assistive devices the dynamics of the cyber-physical-human system becomes significantly more complicated. First, the human-in-the-loop is an intelligent actor and factor in the actual or expected assistive forces while moving, therefore the movement and sensory traces will be different than those collected above. Second, the CPAC system is only partially observable, since we rely on low-fidelity wearable sensors and the intent of the human actor (e.g. preparing to squat down to pick up an object) cannot be directly captured.

B. Assistive Control

To address these challenges, we update the biomechanical model introduced above by incorporating the applied assistive force as an extra input feature, then reevaluate the feature selection and regression machine learning models to predict the lumbar load while control force is applied. For the control of the assistive force a reinforcement learning algorithm is developed to minimize the total or maximal lumbar load possibly combined with nonlinear predictive models. We expect that the exact function to be minimized is more complicated than just the maximal or average lumbar load, and involves safety features as described above, but by taking a generalized arithmetic mean of the time series of the lumbar load with the appropriate exponent the trade-off between long term exposure to medium load and short term exposure to high load can be explored. The characteristic tension in reinforcement learning between exploration or exploitation is going to be especially challenging to address, since the usual E-greedy strategy of using random actions in e fraction of the cases is not going to be appropriate with human subjects. If the control force is minimal, then we expect the human actor to perform the decided action regardless of the assistive force, in which case the algorithm can learn to apply the appropriate assistive force when necessary and not interfere with the human when it cannot prevent a certain action. On the other hand if the control force is larger, then the system might learn to prevent the human making those movements that would put high load on its lower back against her will. Therefore, accurate intent inference must be an essential part of CPAC which could make the difference between success and failure.

Intent inference can be addressed in a variety of ways: (1) recording the action label that is performed by the user as part of the database and employing supervised learning techniques, (2) using contextual information and application specific priors in a hybrid Bayesian inference model, or (3) using unsupervised learning techniques, possibly generative adversarial networks, to create a distribution of possible future movement scenarios, as it has been successfully demonstrated in predicting future frames of a video based on past frames. The intent inference must be combined with the control algorithm to avoid those states that put high load on the lower back (based on the lumbar load inference) while not preventing the user to perform the intended task. We also explore simple audio bio-feedback to the user to inform that the action she is intending to make is going to put larger lumbar load than a specified threshold, thus allowing the user to choose other movement options. These advances in intent inference are highly relevant to other types of wearable technologies, affecting clinical populations, industrial workers and recreational users.

A key challenge in the development of the control algorithm is the unknown response of the human to the experienced assistive force. Sensory data recorded while no assistive force was applied is not directly applicable to scenarios when the assistive control is enabled because the human is expected to alter the use of their muscles. In a way, both the human and the control algorithm should gradually learn the expected actions of the other using on-line learning. However, on-line learning is very time consuming, will not capture the whole range of the design space, and the human cannot be subjected to possibly random assistive forces. To perform effective off-line learning the probability distribution of possible movement patterns in response to various control forces has to be discovered and estimated so that the control algorithm can select the best action for a given long term goal. To collect the necessary information, we plan to develop a range of basic control algorithms (starting from constant assistive forces to standard state-machine based control) and record the same set of tasks (e.g. lifting a weight from the floor) of a human subject. Once we have a baseline data set for each subject that we can use for machine learning of the optimal control, we add the new algorithm with a range of its tunable parameter settings to the existing set of controllers and extend the recorded data set of sensory data. As it can be seen, this is an iterative process where we can carefully measure and validate the effectiveness of the algorithms step by step. Given the iterative process, 5 subjects are tested under this protocol.

C. Limitations and Assumptions

We are assuming that the intent of the subject can be classified in a way that matches our intuition and the performed movement. However, a machine learning based a control algorithm might not use the same classes and has to bridge intuition classes fluidly in real-time. For example, picking up a box from the floor and putting it on a shelf will require multiple intuitions. The segmentation of complicated movements into separate actions (labelled intuition) is of itself a very hard goal. We expect, that the machine learning algorithm is able to learn appropriate and fluid control, or be forced to do continuous response with regularization techniques, even in situations that cannot be classified clearly to any single intent category. However, other than verifying its behavior in a few carefully constructed scenarios, it is not clear how to systematically evaluate the intent recognition algorithm for a wide range of unscripted movement types. Note however, that we can evaluate the combined system, when the intent recognition is combined with the assistive force control, by simply measuring/calculating the lumbar load in lab.

Prototype Development and Validation

According to the invention, wearable sensors and fusion algorithms are integrated into an actuated prototype and tested to measure reductions in lumbar spine loading during daily lifting and leaning tasks, to evaluate the effects on low back injury risks. We have developed multiple prototype iterations to prove out the concept of physically assistive clothing. The challenge in this study is to integrate the critical cyber aspects that enable this technology to be versatile and beneficial outside of the lab. The design and function of the current prototype is briefly summarized: an elastic cable is connected from the shoulders/trunk down to the thighs. A novel exo-interface that we developed securely and comfortably transmits forces to the skin/body by using a conformable anti-slip material (thermoplastic elastomer) that encases and distributes load ova the full surface of the thigh or shoulders and trunk. During tasks such as leaning or lifting this cable stretches and provides assistive low back extensor torques. As a person leans further forward the elastic cable loading increases (up to 250 N in our preliminary studies). Since the moment arm of the assistive cable is about 2-3× that of the muscles, and 3-5× that of ligaments, the cable provides a (torque) mechanical advantage, which both off-loads the low back muscles and reduces the compressive spine forces. This function differs from back belts and orthotics on the market which wrap around the trunk, but since these terminate at/above the pelvis they cannot offload the low back during normal range-of-motion tasks.

As previously mentioned, although strictly passive designs can be compact and light, they are unable to adapt to the varying requirements of lifting tasks. Thus, they would be unable to reduce loading in some instances, while increasing spinal loading, and/or obstructing movement during the performance of other tasks. In order to provide appropriate assistive behavior across a variety of lifting and working tasks, the design approach proposed here incorporates a semi-active design, which is capable of adapting its assistive characteristics to the specific activity being performed. The semi-active design approach proposed here specifically adapts the set point of elastic assistance, based on the characteristics of a given movement, to minimize spinal loading during that movement. Thus, rather than directly provide power for a given movement, the semi-active device essentially performs the function of gravity balancing, but in a manner than adapts to varying configurations of the torso, and varying loading conditions. This approach eliminates the need to directly provide the power for lifting, and therefore greatly reduces the actuator power requirements of the CPAC system, thus enabling a considerably lighter and more compact wearable system. The design approach further provides a fundamental assurance of safety, since it is physically unable to generate large amounts of power. Tendon-based actuation is employed, which provides a compact and soft embodiment, well-matched to human spinal mechanics. Note that the investigators have acquired a design expertise in tendon-based wearable devices, and will employ similar design techniques in the proposed exoskeleton. Among the principal design components of previously developed successful tendon-actuated designs is a motor unit design that incorporates brushless DC motors that drive tendon pulleys through custom two-way clutches. The latter enable highly efficient forward driving, while also providing non-back drivable behavior and large holding forces, such that power is required only for changing the set point, and not for holding. The holding properties of the clutches also enable the motor units to provide holding forces 3-5 times greater than their continuous capabilities, since the peak motor torques can effectively be locked in by the two-way clutches. The net result is a substantially smaller and lighter motor unit than could otherwise by employed. Note that this idea is well-suited to the design objective of changing the set-point of clastic assistance. In fact, this same essential tendon-based motor unit is employed in the hand exoskeleton, which is currently under option for commercial translation by a major medical device manufacturer. Although the motor unit employed in that device is implemented at a smaller scale, the design is highly scalable, and investigators have designed and fabricated larger-scale versions of the same motor unit. The investigators also have considerable experience in developing custom embedded systems for wearable exoskeletons that provide compact, energy efficient, self-contained operation.

A. Experimental Design

To evaluate effectiveness of the CPAC intervention, we perform a human subject study on 15 healthy individuals, with no history of back pain, to determine to what degree CPAC reduces their low back loading. A single-session experimental protocol will be conducted to train users to perform leaning and lifting with and without CPAC. The goal of the study is to compare no-intervention vs. a common commercial back belt (Ergodyne ProFlex 1650) vs. CPAC prototype, using in-lab motion analysis techniques to estimate lumbar loading, but using on wearable sensors to control the device. Each subject will be given 10 minutes to practice tasks (inclusive of breaks), followed by 10 minutes to practice with the back belt, and 10 minutes with the CPAC prototype. The no-intervention condition will always be tested first and repeated as the last trial, as a means to assess fatigue-related confounds. In addition to objective measures of motion, force and EMG, subjects will report subjective comfort and case-of-task after each trial (via visual analog scale).

Human CPS s put high demand on sensor fusion, intent inference and control algorithms, which have to process inherently noisy signals. Based on the exact selection of sensors used for intent and lumbar load prediction as determined within the proposed work, a body area network has to be set up and the algorithms be implemented that can potentially operate autonomously on battery power. Since CPAC continuously interacts with the changing physical and biomechanical environment and must guarantee absolute user safety, we need to develop real-time algorithms, taking into account the body area network. As part of the prototype design, we evaluate our inference algorithms for resilience to low signal-to-noise ratio, non-normal distribution of errors, and missing or delayed data points.

B. Validation

For each leaning and lifting task, a one-way ANOVA is performed with Holm-Sidak correction to statistically assess if the CPAC reduced spinal loading relative to the control condition and relative to the back belt condition. Sample size was selected to distinguish differences>350 N (10% of the NIOSH-recommended safety limit for spine loading). Assuming power=0.9, alpha=0.05, standard deviation=200 N, and 3 pairwise comparisons, results in sample size of 9. It is proposed to collect 15 subjects.

To verify the safety of the control algorithms we artificially lower the maximum assistive force and maximum lumbar load limits to values that a human can safely tolerate and exceed. With these parameters we test that the algorithm indeed obeys and gracefully handles these limits and warns the user (possibly in advance) that the safety limits are exceeded. We compare the predicted and experienced lumbar loads (computed from high fidelity sensor data not available to the control algorithm) for all task categories.

The primary limitation is that in order to rigorously compare across conditions (CPAC vs. no assistance vs. back belt), we only collect a subset of leaning and lifting activities due to time and resource constraints. However, this is expected to be sufficient to demonstrate benefits, and will help move towards testing of more diverse activities (e.g., twisting and picking up object from behind) in the future.

Unlike traditional cyber-physical systems, the CPAC incorporates a human actor that not only provides input signals to the system, but also reacts to the assistance the system provides. The dynamics of each part of the system is fairly well understood through biomechanical models, discrete and continuous physical models, control algorithms for delayed feedback loops. However, the human is a potentially unpredictable element who is actually driving the movement and needs to be part of the predictive model. Therefore, only a holistic design process can address these multidisciplinary challenges and achieve a solution that is seamlessly usable by untrained subjects in a diverse set of environments. The proposed work evaluates machine learning techniques (feature selection, deep neural networks, Bayesian inference, reinforcement learning, etc.) to estimate the state of the human-in-the-loop CPS from low-cost sensors and to make assis-tive control decisions from potentially unreliable data, which will require safeguards to be developed and incorporated.

The successful completion of the work will result in the following outcomes: A benchmark data set made publicly available containing portable sensor and motion lab data, action classification, and computed lumbar loads. In later phases of the project, a smaller dataset with assistive forces included will be also made available. A comparison matrix of regression accuracy across all feature selection and regression methods for the calculation of lumbar load from portable sensor data. Sensor placement documentation and trained models for calculating lumbar load from wearable sensor data working for a wide range of individuals and actions, and useful for development of other types of wearable devices. Human intent inference algorithms for performed action classifications and short term prediction of sensory data. An ensemble of baseline and advanced control algorithms for reducing lumbar load through assistive forces, including executable machine learning models. Wearable, actuated CPAC prototype, whose design will be made available through publication.

Example 7

Smart, Biomechanically-Enhanced Clothing

The objective of this exemplary study is to accelerate the development of smart, biomechanically-enhanced clothing that can reduce low back pain by reducing injuries due to high or repetitive loading. Smart clothing could monitor low back loading via wearable sensors, assist the low back via embedded elastic structures that off-load the lumbar muscles/discs by increasing the mechanical advantage (moment arm) of the extensors to reduce low back injury risk, and train people via biofeedback to promote healthy movement patterns and prevent injuries. Smart clothing can be lightweight and low-profile to fit seamlessly into people's daily life, and could have a transformative effect by improving low back health and reducing costs due to medical care and missed work.

The smart clothing could be transformed into a lightweight, form-fitting, low-power, wearable garment that helps protect low back muscles and spinal discs from overloading and overuse. The smart clothing is the fusion of technology and textiles, and could serve to both monitor low back loading (to identify injury risks and enable timely interventions), and provide direct assistance (to off-load spinal tissues, FIGS. 5D-5E). This proposed transformation of clothing is similar to how wristwatches have transformed from timepieces into health monitors, which promote physical activity and well-being; however, smart clothing is even more promising because it can also be embedded with textile-based structures, can assist movement and reduce biological tissue forces that lead to injury. The way in which this proposed smart clothing would assist the low back is biomechanically distinct from conventional back belts/supports, because it uses elastic structures in parallel with the low back musculature to reduce biological tissue loading (FIGS. 5D-5E). As a person leans forward or bends down, his/her buttocks naturally protrude backwards to maintain balance, stretching the elastic structures and creating assistive extension torque about the low back. Smart clothing provides a unique and potentially paradigm-shifting opportunity because clothing is ubiquitous, worn everyday, and when designed properly it is lightweight and unobtrusive. Long-term, smart biomechanically-enhanced clothing is expected to: fit seamlessly into a person's daily life; connect individuals with health information to empower them to modify their own physical activity; generate vast public health data that can inform evidence-based clinical and workplace practices; directly augment movement biomechanics to reduce unhealthy spinal loading; reduce incidence of low back pain, and thus costs associated with health care and missed work; and leverage existing soft goods manufacturing methods to enable a scalable and affordable solution.

There are many potential design variations of smart clothing, and designs can be customized to assist specific populations, or individuals during certain types of tasks. For instance, for a surgeon who is leaning for prolonged periods during a procedure it may be beneficial to create smart clothing that universally (always) provides assistance. For a nurse, care giver or package handler who is doing intermittent leaning/lifting tasks it may be better to monitor their behavior via embedded sensors and only provide selective assistance (e.g., by using a low-power clutch to engage the elastic cable) when sensor algorithms identify increased injury risk. If the goal is to train someone to lift properly, then assistance might only be provided when proper technique is used, to incentivize healthy movement. Or if the goal is to strengthen weak muscles, then smart clothing might provide selective resistance to increase a person's exercise each day. These are a few potential applications, which highlight how this paradigm-shifting apparel could aid individuals across age, profession, geographic region and socioeconomic status. There is no single solution (smart clothing behavior) that is right for everyone. The strength of this study is that we seek to address critical scientific/engineering challenges that are fundamental to accelerating the development of all of these clothing concepts, which are "smart" (use sensor algorithms to assess injury risk) and/or "biomechanically-enhanced" (physically assist the user to off-load tissues).

Two key scientific/technological leaps are needed to realize the full societal benefits of smart, biomechanically-enhanced clothing. First, we must develop an understanding of how to use wearable sensor data to identify unhealthy movement patterns such that timely feedback/intervention can be provided. This requires us to integrate expertise in wearable sensing, bio-signal analysis, biomechanics and clinical care. Second, we need to understand of how to comfortably provide assistive forces to the body to prevent injuries for individuals of all ages. This requires us to integrate wearable technology, human-device interaction, biomechanics, and geriatrics.

Identify Wearable Sensor Data Needed to Track Low Back Loads: To determine the minimum portable/wearable sensor data needed to estimate low back loading during locomotor, leaning, lifting and sedentary activities. Human subject biomechanics experiment, comparing portable sensor estimates of low back loading to those obtained via comprehensive in-laboratory motion analysis. Candidate portable sensors could provide surrogate estimates of lumbar angle/motion, and body or muscle forces. This research provides the critical scientific foundation/evidence needed to enable the use of wearable sensors outside the lab to estimate lumbar loading. Understanding how to use wearable sensor data to identify unhealthy movement patterns in situ is the critical first step towards providing timely intervention, and linking individuals with information that empowers them to reduce their injury risk.

Characterize Assistive Forces that Can be Comfortably Applied to the Body: To characterize the magnitude and location of force that can be comfortably applied to adults (young and old), and assess optimal levels of assistance for leaning and lifting tasks. Human subject experiments are performed to quantify the benefits of biomechanically-enhanced clothing vs. commonly-used commercial back belts, in terms of reduced lumbar loading. Understanding the forces that can be comfortably applied is foundational to the realizing the societal benefits of smart, biomechanically-enhanced clothing (and other wearable technologies) because if a device is uncomfortable then people generally will not use it. Findings related to human-device integration are expected to be generalizable to other applications (beyond low back) and other wearable devices.

Each objective of this study addresses a critical scientific or technological hurdle that must be overcome to realize the societal health benefits and accelerate the development of smart, biomechanically-enhanced clothing. The objective 1 focuses on portable monitoring of low back loading using wearable sensors. The objective 2 seeks to address questions related to: how much assistive force can be provided comfortably to targeted body segments, how much assistance is optimal to provide, and how much does this reduce lumbar loading. We recruit and consent 40 healthy adults for each aim: 10 individuals between ages 18-30 (Younger adults), 10 between 31-45 (Middle-Aged adults), 10 between 46-60 (Older adults), and 10 between 61-75 (Seniors). One exception, 80 subjects (20/group) are recruited. Sample size calculations are detailed later. Subjects are consented under IRB #141697 and IRB #160992. Inclusion criteria include: no locomotor disabilities or impairments, no low back or other major musculoskeletal injuries within the last year, and no chronic or acute skin issues, in order to avoid confounding variability and to ensure participant safety. Individuals under the age of 18 are excluded because the target demographic is those who are more susceptible to low back injury, which is not children or adolescents. Individuals over 75 are excluded because of risks due to sarcopenia, age-bone loss, and typically they have a kyphotic posture (excessive curvature) which may be confounding.

This study is focused on addressing foundational scientific/technological challenges that facilitate development of a class of a lightweight, form-fitting, low-power, wearable garments that assist and protect low back tissues. Future studies may focus on developing a clothing/apparel product, addressing the optimal way to provide biofeedback to individuals to train healthy movement pattern; applying big data approaches to consolidate information from a large population to inform improvements in health provider care or public health; and identifying the optimal machine learning algorithms necessarily, nor is it to evaluate long-term reductions in injury. These each encompass promising and exciting potential benefits of smart clothing, which benefit from advances in information integration and informatics.

Identification of Wearable Sensor Data Needed to Track Low Back Loads

To determine the minimum wearable sensor data needed to estimate low back loading during locomotor, leaning, lifting and sedentary activities, for each age group, wearable sensor-based estimates are capable of approximating motion laboratory-based estimates of low back loading with root mean square error of <200 N (~5% of NIOSH-recommended safe loading limit, based on 1981 population guidelines; newer guidelines use a more complex, person- and task-specific equation). Wearable sensor-based algorithms successfully categorize low vs. medium vs. high spinal loading tasks with accuracy >90%, for all age groups.

Preliminary human subject experiments & biomechanical analysis: We have performed an in-laboratory low back loading study and completed analysis of 4 young, healthy adult subjects during static forward leaning at 30, 60 and 90 degrees and during dynamic lifting of 10 and 25 kg. The two key outcome measures were muscle activity of the erector spinae (low back extensor) muscles, and estimated compressive spine force at L5/S1, computed using high-frequency, high-resolution motion, force and EMG data. Analysis methods are detailed later in thus study, but briefly: muscle EMG is used to estimate lumbar muscle force, then combined with inverse dynamics and anthropomorphic (muscle moment arm) data to estimate compressive spine forces. Two general categories of analysis are commonly used to noninvasively estimate low back loading: (i) pure inverse dynamics and (ii) EMG-assisted/driven dynamics analysis. Pure inverse dynamics combines motion and force data to estimate net joint force ($\overrightarrow{F_{net}}$), but this is insufficient to capture internal contact forces due to ligaments or muscles. EMG-assisted approaches extend inverse dynamics by incorporating muscle-specific ($\overrightarrow{F_{muscle}}$) and often ligament-specific $\overrightarrow{F_{ligment}}$ forces to improve estimates, including capturing effects due to muscle co-contraction. Total internal contact loading ($\overrightarrow{F_{contact}}$) can then be computed by summing the net force with contributions from each active (muscle) and passive (ligament) source:

$$\overrightarrow{F_{contact}} = \overrightarrow{F_{net}} + \sum \overrightarrow{F_{muscle}} + \sum \overrightarrow{F_{ligment}}$$

This form of EMG-assisted analysis is applied to estimate internal vertebral disc forces. We have substantial experience with both categories of biomechanical analysis, using inverse dynamics to estimate lower-limb, low back and trunk biomechanics, measuring multi-muscle lower-body and low back EMG, and employing EMG-assisted modeling to incorporate muscle-specific contributions to improve internal force estimates.

End-user (focus group) interviews: We have performed 24 in-person interviews with potential end-users (mainly nurses) and have compiled their feedback to identify key requirements to inform the design, form-factor and the range of potential wearable sensors. 95% of those surveyed who had back pain expressed an interest in using a wearable assistive device daily to prevent future back pain. When asked what features they would desire in the wearable system, 75% said that they wanted something that is concealable and/or form-fitting, and 69% said that they would not wear a device that is bulky, obstructive or otherwise restrictive. Nurses frequently commented on how important it is to have a device that is convenient to use; for example, nurses commonly have patient lift devices at their disposal, but largely avoid them because they are inconvenient to move around, and because they prolong their daily duties.

Candidate sensor selection: We have identified a set of candidate/potential portable sensors, based on the published biomechanics literature, our own preliminary studies and our interviews with potential end users. Portable sensors are not as accurate or comprehensive as in-laboratory research-grade measurement systems; however, the portable sensors can potentially serve as wearable surrogates for these in-lab measures. Two main categories of sensor were identified: (i) motion/orientation and (ii) force/muscle. Motion/orientation sensors provide information about lumbar angle, and thus serve as a surrogate for motion capture cameras (which are impractical outside of the laboratory). These sensors include: (a) inertial measurement units (IMUs, combining accelerometers and gyroscopes) that could be placed on the trunk and pelvis (using the difference in angle to estimate the configuration of the lumbar spine), (b) flex sensor adhered to the skin to estimate localized lumbar orientation (i.e., lordosis vs. kyphosis). Force/muscle sensors provide information about the level of loading itself, and serve as a surrogate for force plate and high-fidelity electromyography recordings in lab. These sensors include: (c) pressure or force sensors (e.g., inside the shoe to estimate forces applied to the ground, (d) pressure-sensing fabric (e.g., along the buttocks to measure forces during sitting), (c) surface EMG electrodes placed on lumbar or abdominal muscles to quantify activation.

A comprehensive motion analysis study is performed to evaluate the ability of wearable sensor data to estimate low back loading during a range of tasks, similar to commonly experienced physical demands in daily life: static leaning at 30, 60 and 90 degrees (standing and seated), dynamic lifting of a 10 and 25 kg weight up to 1 meter height (standing and sitting), sitting with both good and bad posture (based on OSHA guidelines), lying on back and on side, and walking on level, uphill (6 degrees) and downhill (−6 degrees) at 0.8 (slow), 1.2 (moderate) and 1.6 m/s (fast) speeds. High-precision laboratory-based measurements (motion capture, force plates, and multi-channel EMG) are analyzed to provide a non-invasive estimate of internal lumbar loading. A well-established EMG-assisted modeling approach is employed to estimate compressive, shear and total (magnitude of) force at the L5/S1 spinal level. Complete methodological is implemented using a combination of software packages (Vicon Nexus, Visual3D, MATLAB and OpenSim). This EMG-assisted approach, which is nearly identical to the approach we implemented in our recent study on walking biomechanics, is complex in its details (due to 3D geometries, EMG-to-force mapping, electromechanical delays, etc.), but conceptually is relatively simple to summarize in 4 parts: (1) Standard rigid body inverse dynamics analysis is performed to estimate net 3D lumbar moments and net force ($\overrightarrow{F_{net}}$). (2) Next, an EMG-to-force mapping algorithm is used to estimate individual lumbar and abdominal muscle forces ($\overrightarrow{F_{muscle}}$) Since there are more muscles than EMG signals recorded, anatomically or functionally similar muscles are assumed to have the same activation pattern; a commonly-used and reasonably well supported assumption for the lumbar musculature. (3) Optimization is performed to correct/adjust individual muscle forces (yielding $\overrightarrow{F_{muscle}}$) and to estimate ligament forces ($\overrightarrow{F_{ligment}}$), such that these dynamics satisfy all 3 moment equilibrium constraints (from inverse dynamics). The cost function attempts to minimize muscle force corrections and constrains muscles to provide non-negative forces (i.e., allowing them to pull but not push). (4) The resultant internal forces on the lumbar spine ($\overrightarrow{F_{contact}}$) can then be computed by summing the net forces and forces due to muscles and ligaments. The magnitude of force at L5/S1 ($\overrightarrow{F_{contact}}$) will be used as the primary outcome, which portable sensor estimates will be compared against. Also, for each participant, a set of calibration trials (flexing/extending low back against a load cell) will be performed at the beginning of each study to determine EMG-to-force scaling factors. Methodological limitations and other considerations are discussed further in Limitations section below. The following candidate portable sensors will be worn and track data simultaneously (and synchronously with other motion capture modalities): (1) Delsys Trigno sensors, which contain 3-axis accelerometers (37×26×15 mm, 16-bit, 2000 Hz sampling, Boston, MA) and bipolar surface EMG electrodes. At minimum, two will be placed on primary low back extensor muscles (right/left erector spinae) and two on the primary flexor muscles (right/left rectus abdominus). (2) Xsens sensors (3×6×2×5×10 mm, 10 g, 1000 Hz, Enschede, Netherlands) with 6-axis IMU will be placed midline along the back, at spinal levels L5, T8 and C8, and bilaterally on each thigh, shank and foot. (3) Novel Pedar-x pressure-measuring insole (400 g, 256 individual sensors, 2000 Hz, Munich, Germany) worn in both shoes. (4) Sensor Edge (Parsippany, NJ) pressure-sensing fabric worn on/behind the buttocks. (5) Spectra Symbol Flex sensor 2.2 (Salt Lake City, UT) placed on the skin above the lumbar spine, directed axially along the spine, left of the Xsens sensor. Regression analyses (linear and non-linear) is employed to use portable sensor data to approximate lab-based estimates of lumbar force, based on biomechanical rationale below. Data from all trials will be appended together prior to regression analyses. Linear analysis: Multiple linear regression analysis using least squares will be performed for each subset combination of candidate sensors (i.e., N factorial combinations for N sensors), identical to methods published in [41]. Non-linear analysis: Since the non-linearity coefficients are not known a priori the objective here is to explore a range of possibilities beyond linear regression. Therefore, exponents of 0.5 and 2 will be applied to each individual sensor and each combination of sensors, and regressions re-run. Both linear and non-linear forms have a biomechanical analog, and therefore this analysis can also be thought of as a statistical way to capture the effects accomplished by fusing data from multiple portable sensors. To briefly expound: coefficients multiplied by force data (which can be computed from the pressure insoles) could serve as surrogate for external force. Meanwhile, coefficients multiplied by EMG data can be thought of as a muscle moment arm multiplied by an EMG-to-force scaling factor (collectively represented by the single coefficient) multiplied by an estimate of muscle force (from EMG, and this relationship may be either linear or non-linear depending on factors like muscle length change). Whether one approaches this question of how to integrate sensor data as an abstract signal analysis problem, or as a simplified biomechanical modeling exercise, the numerical analysis techniques employed here are the same. Regression coefficients from each analysis is used to estimate (i.e., reconstruct) time varying spinal forces, and then the root mean square error (RMSE) vs. lab-based estimates will be computed across all trials. Each combination and regression formulation is compared against the 200 N threshold to test. The pareto-optimal set of portable sensors will be defined as the minimum number of sensors that yield average RMSE across all trials<200 N;

and these sensors and the associated regression algorithm is used in the experiment. If no combination yields RMSE<200 N then the algorithm that yields the lowest RMSE is used in the experiment. We propose 200 N to be a pragmatic threshold target with sufficient accuracy to assess low back loading risk (given that this threshold reflects ~5% of the 1981 NIOSH-recommended loading limit).

We perform a blinded study to evaluate the ability of portable sensor estimates to categorize Low vs. Medium vs. High lumbar loading tasks. Low will be defined as spinal force magnitude of 100-500 N, Medium as 1000-2000 N, and High as 2500-3500 N. Tasks performed will be different from those tested in Experiment 1a (to avoid training set confounds), and will be selected ahead of time based on a small pilot study that evaluates potential tasks (e.g., lifting from a different posture). Human subjects participate in a biofeedback study, in which the Low, Medium and High loading tasks randomly appear on a visual display every 15 seconds, informing the person to complete said task. For each trial (instance of task performance), the sensor algorithm (which is blinded to any information about the task other than the portable sensor data) aims to predict the loading level (Low/Medium/High). Loading level is compared to the "ground truth" (displayed task), then classification accuracy is compared to the hypothesized 90% threshold. 200 randomized trials are performed, with intermittent breaks.

Statistical Analysis & Sample Size. For each age group, we perform one-sample, one-sided t-tests, to evaluate whether RMSE (of lumbar loading magnitude) from each combination of candidate sensors is significantly greater than 200 N. ANOVA is not employed here since the goal is not to compare all sensor combinations to each other. Next, to compare differences between each of the 4 age groups, a one-way ANOVA with post-hoc Holm-Sidak step-down correction is performed to account for multiple comparisons. Similar analysis is performed for Hypothesis 1b: one-sample, one-sided t-tests to evaluate whether classification accuracy is significantly less than 90% for each sensor combination, and ANOVA to compare results between age groups. Sample size was computed for a one-sided, one-sample t-test assuming power=0.9, alpha=0.05, reference=200 N, measured mean=400 N, and standard deviation=200 N, values based on previous results and an upper-bound limit (~10% of previously defined NIOSH safety threshold) on measured forces that we deemed should be distinguishable from the reference threshold. This yielded a sample size of 9. We recruit and test 10 subjects, which is consistent with or larger than prior studies employing similar EMG-assisted analysis methods to estimate lumbar loading.

The outcomes are a benchmark data set with portable sensor and motion lab data, an initial evaluation of portable sensors, and ability to combine these sensor data to estimate lumbar loading, determination of the minimum set of sensors capable of estimating lumbar loads with desired accuracy (RMSE<200 N), and an assessment of whether portable sensor estimates can accurately (>90%) categorize low/medium/high loading tasks. Successful completion of this work enables confident and targeted deployment of instrumented clothing outside the lab, for future studies that monitor lumbar loading, provide biofeedback and track pain/injury incidents.

The research is carried out in the state-of-the-art Motion Analysis Lab in the Rehabilitation Engineering Center, which has the measurement infrastructure to record synchronized signals from all of the aforementioned systems, nearly all of which are currently being used in the lab for ongoing research projects. Alternatively, there are many additional sensor fusion approaches that may be valuable to explore (secondarily to the primary regression analyses outlined), such as Kalman filter or machine learning approaches. These more sophisticated analyses are anticipated to be even more beneficial, but depend first on obtaining comprehensive data from in-lab (research-grade) instruments and simultaneously from portable sensors. The objective is to publically archive the data collected so that other researchers (who may not have access to motion lab facilities or expertise to carry out these proposed experiments) can apply their own learning or data fusion approaches to this benchmark data set. In our analyses, some level of individualization may be necessary for the classification of forces. For example, in practice people may need to perform a few person-specific calibration trials (particularly if a signal like EMG is used, which can vary based on day-to-day based on skin or other physiological conditions). Adding a brief calibration period prior to experimentation (if needed) is not a problem, and such calibrations are even common with many commercial electronic devices (e.g., smart phones, Wii video game), so this possibility is not considered impractical in the lab or problematic long-term.

This research aims to address key biomechanical factors (overloading due to high force and overuse due to repetitive loading) that predispose individuals to degenerative disc disease and low back pain, but our approach does not address all causes of low back pain. Low back pain can also result from other etiologies, some of which are neurogenic, psychological, environmental (e.g., stress), congenital or acquired spinal stenosis. However, this point is not paramount as the core idea proposed here is to reduce risk of low back injury and pain amongst the general public due to excessive loading, as opposed to treating or providing relief to individuals already experiencing low back pain, or trying to treat every possible cause of pain. Experimentally, we employ comprehensive a biomechanical analysis techniques, but all methods employed are non-invasive. In reality, there is currently no direct way to validate muscle forces in vivo (as this would require us to implant load sensors in series with every single muscle and ligament). However, substantial evidence and arguments have been put forth suggesting validity of EMG-assisted model estimates, specifically: (i) the strong correlation $F_{muscle}$ force estimates with EMG (which is particularly compelling during static leaning posture, since muscle activation and contraction dynamics are not confounds), (ii) that results are constrained by inverse dynamics (i.e., consistent with the laws of physics, in terms of net moments and forces), and (iii) that EMG-assisted results have been tested and validated under controlled conditions that support epidemiological findings. Collectively these give us confidence that the muscle force estimates are reasonable, and that we can estimate relative increases and decreases in lumbar force by combining non-invasive muscle activity, kinematics and kinetics data. Musculoskeletal properties/parameters that are not known (such a person-specific ligament stiffness) are constants in the analysis, and thus are expected to affect all conditions equitably. This could introduce offsets in our estimates relative to absolute (ground truth) force magnitudes, but the success of smart clothing and the success of these research studies does not depend on ultra-high accuracy force estimates (for the same reason that pedometers did not initially need to be super high-accuracy) in order to provide useful feedback to users (though accuracy has improved over time due to advances in sensing and algorithms). Despite limitations of non-invasive lumbar load estimates, we contend that the analyses used are sufficiently-well established and validated to yield reasonable estimates for our purposes (i.e., to differentiate low vs. medium vs. high loading, and generally quantify the volume of high loading that occurs, and how this changes over time). Three loading levels were selected for categorization testing. This seemed reasonable, though 4 or 5 also seem reasonable. The precise number is not critical, as we generally expect that some relatively small, finite number of levels would be useful to categorize, and that by tracking (most importantly) the magnitudes and instances of=high loading that this would be sufficient to provide actionable, preventative feedback on low back injury risk. Furthermore, future investigations may assess risk in a more sophisticated way. For instance, instead of tracking only lumbar force magnitude, one could track lumbar load and angle together (since the spine can handle higher forces when at neutral configuration than when severely kyphotic or lordotic), or one could track loading history; though we save these for future investigations. Finally, a subset of representative tasks were selected to capture the dynamics of common daily tasks. It is impractical/impossible to test every conceivable daily activity, but this is not crucial so long as a rich variety of tasks are included that induce various levels of loading. Very high loading tasks (e.g., >3500 N) are not be tested for safety reasons, but if algorithms are still expected to extend to these higher loads.

Characterization of Assistive Forces that are Comfortably Applied to Body

The objective is to characterize the magnitude and location of force that can be comfortably applied to adults (young and old), assess optimal (stiffness) levels of assistance for leaning and lifting tasks (to minimize spine loading), and evaluate the benefits of biomechanically-enhanced clothing. It is expected that maximum comfortable loading of the thigh and shoulders will decrease with increasing age; and biomechanically-enhanced clothing reduces lumbar loading compared to back belt and no-intervention.

We have developed multiple prototype iterations. An elastic cable is connected from the shoulders/trunk down to the thighs. A novel exo-interface that we developed securely and comfortably transmits forces to the skin/body by using a conformable anti-slip material (thermoplastic elastomer) that encases and distributes load over the full surface of the thigh or shoulder/trunk. During leaning/lifting this cable stretches and provides assistive low back extensor torques. As a person leans further forward the elastic cable loading increases (up to 250 N in our preliminary studies). Since the moment arm of the assistive cable is about 2-3× that of the muscles, and 3-5× that of ligaments, the cable provides a (torque) mechanical advantage, which both off-loads the low back muscles and reduces the compressive forces on the spine This function differs from back belts, braces and orthoses on the market which wrap around the trunk, but since these devices terminate at/above the pelvis they cannot effectively offload the low back during normal range-of-motion tasks.

Preliminary experimental data: We have demonstrated the ability of our prototype to reduce lumbar muscle EMG and spine forces in young adults. Based on human subject testing in our lab (N=4), we found that the prototype reduced low back muscle activity by 10% and 18%, on average, at 60 and 90 degree lean angles, and for individual subjects by as much as 40%. Our preliminary findings are consistent prior literature (on industrial exoskeletons) and biomechanical modeling predictions.

Loading platform for quantifying maximum forces that can be applied to body: To isolate the magnitude of forces that can be comfortably applied we have built a loading platform, essentially a material testing machine to measure forces applied to the human body). We have obtained IRB approval (#160992) to use this for human subject testing. The experimenter manually applies forces via the loading lever, which tensions a cable, which then pulls down (or up) on the subject via the attached exo-interface. A load cell in series with the cable measures forces applied while subjects provide verbal comfort feedback. Pilot studies have been performed on a small number of young healthy adults to demonstrate proof of concept, using exo-interface attachments. One drawback is that manual force application limits precision and repeatability of forces applied; thus a computerized, precision-controlled system will be used in the proposed experiments.

A prototype is designed with easier adjustability to: (i) accommodate individuals of different sizes and (ii) allow swapping of elastic cables to vary stiffness. A load cell will be placed in series with the clastic cables for testing. Experiments are performed to isolate the maximum force magnitudes that can be comfortably applied to the thighs and shoulders of individuals of different ages. A universal device emulator (HuMoTech) will be used to safely and accurately apply specific loads and rates of loading, via exo-interface materials attached to the body. The emulator system will record forces, while synchronized motion capture records displacement of the exo-interface (to track migration of this interface relative to bony landmarks on the body, which is a secondary measure of interest, important to the design of wearable devices). A 2-day protocol will be carried out, with low-medium forces (10 peak magnitudes from 20-200 N) and rates of force (5 magnitudes from 40-200 N/sec, at 100 N peak) applied during Day 1. Each trial includes 10 discrete tugs, and a maximum loading duty cycle of 0.5 Hz is used. Subjects provide a comfort feedback score via a visual analog scale (0 very uncomfortable to 10 comfortable) immediately after each condition tested. A break of at least 2 days is required, at which time the subject is asked to report any soreness or discomfort, and the skin is visually inspected by the experimenters for evidence of tissue irritation or damage. If any concerns arise, then the subject is formally assessed and incidents are documented and reported to the IRB. Otherwise, medium-high forces (10 peak magnitudes from 200-600*N) and rates of force (40-1000 N/sec, at 400*N peak) are applied during testing Day 2. Asterisks (*) indicates that these values are reduced, if needed, based on comfort study results. Again, subject soreness follow-up and visual skin inspection will be performed after 2 days. Safety notes: all pulling forces are <1000 N, which is far below forces typically generated by a person's biological muscles [64]. The shear pressures experienced by the skin at these force magnitudes is substantially less than the threshold at which skin becomes injured (~54 KPa, Goldstein 1998). All loading applied is distributed over sufficient skin area such that average stress is always less than 25% of this magnitude. Subjects are reminded that they can stop at any time, and if the subjective comfort score drops below 3, then no higher forces will be applied. Finally, an internal "breakaway" tether in the emulator system prevents undesired high loads from being transmitted to the person. Comfort scores (primary outcome) and migration data (secondary outcome) will be compiled from both days. For each age group we identify max comfortable force, the highest force in which self-reported comfort score is greater than 4.

A single-session experimental protocol is conducted to train users to perform leaning and lifting with and without biomechanically-enhanced clothing, to identify optimal elastic cable stiffness properties for each task, and to compare no-intervention vs. a common commercial back belt (Ergodyne ProFlex 1650) vs. our biomechanically-enhanced clothing prototype, using in-lab motion analysis techniques to estimate lumbar loading. Each subject will be given 10 minutes to practice leaning and lifting tasks (inclusive of breaks), followed by 10 minutes to practice with the back belt and 10 minutes with the biomechanically-enhanced clothing prototype. After habituation, a series of cable stiffnesses (from weak to very stiff, providing 0-400 N of force at peak stretch) are tested each for leaning and lifting task (same tasks tested in Experiment 1a). Stiffness conditions are randomized. Optimal stiffness of the elastic band (i.e., which minimizes spine loading) will be identified for each task (in post processing) and used to compare against no-intervention and back belt conditions. The no-intervention condition is always tested first and repeated as the last trial to assess fatigue-related effects. In addition to objective measures of motion, force and EMG, subjects report comfort and ease of task levels after each trial (via visual analog scale).

Statistical Analysis and Sample Size. a one-way ANOVA is performed with Holm-Sidak correction. Similar ANOVA analysis is performed to compare no-intervention vs. back belt vs. biomechanically-enhanced clothing, and then to compare across age groups. Sample size was selected (based on pilot data) to distinguish a 100 N difference in maximum comfortable force between age groups, assuming standard deviation of 75 N, 6 pairwise comparisons, power=0.9 and alpha=0.05. This yielded a minimum sample size of 18 subjects/group. We collect 20/group, and distinguish differences>350 N (10% of NIOSH safety limit). Assuming power=0.9, alpha=0.05, standard deviation=200 N, and 3 pairwise comparisons, results in sample size of 9. We collect 10 per age group.

Outcomes are a force vs. rate of force vs. age "comfort map" signifying the magnitude of force that can applied comfortably to the shoulders and thighs (pertinent to the design of smart clothing, robotic exosuit and other wearable assistive devices), a characterization of how optimal assistance (i.e., force provided by elastic cable) varies with lifting and leaning tasks, and objective evidence of the relative benefits of biomechanically-enhanced clothing in terms of reducing lumbar loading.

Potential pitfalls are related to prototype fit and the number of conditions that can be feasibility tested per subject. We plan to fabricate 3 sizes (small, medium, large) of the prototype to accommodate most adults. However, some inclusion criteria may need to be added to exclude individuals who are too tall or obese. A follow-up study on obese vs. non-obese individuals would be scientifically interesting, but this is beyond the scope here. Testing focus is on common leaning and lifting tasks. There are other variations that could also be tested (e.g., which involve twisting or different postures), but fundamentally the same biomechanical mechanism would off-load the lumbar spine. Thus, conclusions are expected to generalize to other common activities and body postures. The 2-day protocol, which delays application of higher forces, also helps avoid pitfalls in the experimental design. Finally, to address a common concern raised with all assistive devices: couldn't providing assistance also be detrimental, leading to muscle atrophy or bone loss due to reduced loads? In short, yes it could, if too much assistance is provided too often. But this theoretical possibility does not change the reality that there many individuals who are suffering from low back pain due to injuries caused by high or repetitive forces. There individuals would benefit from assistance that partially off-loads their lumbar muscles and discs. Pilot studies suggest our prototype reduces spine loading by 10-40%. For a surgeon who has to lean over for 6 hours to perform an operation, or a caregiver who is repeatedly helping to lift and move an individual being cared for, it seems extraordinarily likely that these people would benefit from selective assistance without negative muscle or bone decay consequences. In terms of alternative approaches, as discussed in preliminary data, the loads in the experiment could also be applied via our manual loading platform, but it would not be possible to accurately control rate or peak magnitude of force application. For the experiment, one could employ a purely musculoskeletal modeling approach to estimate optimal stiffness; however, musculoskeletal simulations have not yet demonstrated sufficient predictive accuracy to ensure that these results would be representative of how humans adapt their movement while wearing the biomechanically-enhanced clothing; thus necessitating collection of these experimental data.

The primary outcome in the experiment is subjective comfort data, which studies suggest can be captured via visual analog scale. This experiment focuses on carefully and comprehensively testing thigh and shoulder loading. In the future, other body segments, such as shank or foot could be tested using a similar protocol, or loading direction could be varied in future studies. Scientifically there is a larger space to explore, but it is not necessary for our intended purpose in this study. As detailed previously, there are limitations and assumptions inherent in biomechanical analysis, which uses only non-invasive measures to approximate internal loading. However, because these assumptions are consistently applied across all conditions tested, we have high confidence in the ability to quantify relative changes in lumbar loading. Evaluation is limited to short-term biomechanical effects. If results are promising, then future studies should also track longitudinal benefits.

The goal of the study is the "development of next generation health and healthcare research through high-risk, high-reward advances." Therefore, it is beneficial to explicitly highlight the key risks and rewards inherent in this research study. It has not previously been demonstrated and it is currently unknown if or how well wearable sensors can estimate low back loading outside of the lab. If, as we hypothesize, we can combine wearable sensor data to monitor low back loading outside the lab then this would be game-changing in terms of providing individuals with real-time (or daily) biofeedback that enables them to modify their physical behavior to prevent low back pain, and potentially in terms of generating vast amounts of public health data that could inform home and workplace best practices.

Based on prior exoskeleton and exo-suit research we are confident that wearable devices can be used to physically assist younger and even middle-aged adults (based on prior literature and our own pilot studies); however the risk is that it is unknown what level of assistive forces can be applied comfortably to Older adults and Seniors, who could benefit most from biomechanically-enhanced clothing. Reward: If sufficient forces can be applied comfortably then this will open the door to a variety of smart, biomechanically-enhanced clothing solutions (FIG. 2) that help prevent low back pain amongst the aging population. This enables them to stay physically active and socially engaged, which is expected to improve their well-being and reduce healthcare costs due to low back injury and pain.

Advancing Scientific Knowledge and Societal Impact. This study integrates expertise in musculoskeletal biomechanics, bio-signal analysis, soft robotics, wearable assistive technology, geriatrics and clinical management of low back pain to transform clothing from materials that cover the body into wearable systems that can track and protect low back health. This research will provide the critical scientific foundation/evidence needed to use wearable sensors outside the lab to estimate lumbar spine loading, and will systematically characterize external forces that can be applied comfortably to individuals across a range of ages, which is crucial for societal translation. Biomechanical analysis is performed to quantify the benefits of smart, biomechanically-enhanced clothing vs. a commercially-available back belt and vs. no intervention, in terms of reduced lumbar loading. Findings related to human-device integration and portable sensing is generalizable to other smart clothing applications (beyond low back), and other wearable devices (e.g., robotic exosuits).

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

Some references, which may include patents, patent applications, and various publications, are cited and discussed in the description of the invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference.

What is claimed is:

1. A wearable device configured to be operably worn by a user for monitoring ankle moment, calf muscle force, and/or Achilles tendon force, comprising:

a plurality of sensors, each sensor configured to be operably worn by the user to detect information about a biomechanical activity, the plurality of sensors comprising one or more force sensors configured to be located under a foot of the user, and one or more motion sensors configured to be located on the foot and/or shank segment of the user; and a processing unit in communication with the plurality of sensors and configured to process the detected information by the plurality of sensors to estimate the ankle moment, calf muscle force, and/or Achilles tendon force by combining force magnitude and center of pressure data from the one or more force sensors with body segment orientation data derived from the one or more motion sensors, and communicate the estimated ankle moment, calf muscle force, and/or Achilles tendon force to the user and/or a party of interest.

2. The wearable device of claim 1, wherein the plurality of sensors further comprises one or more electromyography (EMG) electrodes.

3. The wearable device of claim 1, wherein the one or more motion sensors comprise inertial measurement units (IMUs), flex sensors, goniometers, or a combination thereof.

4. The wearable device of claim 3, wherein each IMU comprises at least one accelerometer and/or at least one gyroscope used for estimating the linear motion and/or angular motion of a limb segment on which said IMU is located.

5. The wearable device of claim 1, wherein the one or more force sensors comprise pressure or force sensors, pressure-sensing insoles, pressure-sensing fabrics, strain gages, muscle sensors, or a combination thereof.

6. The wearable device of claim 1, wherein the detected information by the plurality of sensors is processed by statistical modeling combined with biomechanical algorithms.

7. The wearable device of claim 6, wherein the statistical modeling comprises linear regression and/or other sensor fusion algorithms.

8. The wearable device of claim 6, wherein the biomechanical algorithms comprise physics-based equations of motion applied to a model of the musculoskeletal system.

9. The wearable device of claim 1, wherein the detected information by the plurality of sensors is processed by a method of inverse dynamics or machine learning, or a combination thereof.

10. The wearable device of claim 1, wherein the processing unit is further configured to estimate musculoskeletal loading using reference data that is either stored on data storage means in communication with the processing unit or reference data that has been collected or inputted from the specific user and used to calibrate or establish the processing algorithm.

11. The wearable device of claim 10, wherein the reference data are obtained by lab-based sensors, and the data storage means comprises a database, a cloud storage system, and/or a computer readable memory.

12. The wearable device of claim 10, wherein the processing unit is further configured to alert the user when the musculoskeletal loading or microdamage is greater than a threshold that has been predetermined or a threshold that has been calibrated for the specific user.

13. The wearable device of claim 12, wherein the processing unit is further configured to advise the user on when and how to adjust their movement, actions or physical activity type and duration so as to reduce injury risks.

14. The wearable device of claim 13, wherein the processing unit is further configured to communicate to a computer, a smartphone, a smartwatch, a tablet or other user feedback or data acquisition device for outputting at least one of the following: estimated musculoskeletal loading, alert and advice, estimates of microdamage or microdamage accumulation, and/or injury risk, and storing the estimated musculoskeletal loading, alert and advice, estimates of microdamage or microdamage accumulation, and/or injury risk, and inputting user inputs.

15. The wearable device of claim 13, further comprising a biofeedback unit in communication with the processing unit for outputting or displaying at least one of the estimated musculoskeletal loading, alert and advice, estimates of microdamage or microdamage accumulation, and/or injury risk using audible, visual, tactile, haptic, thermal, electrical or other biofeedback means, and storing the estimated musculoskeletal loading, alert and advice, estimates of damage accumulation, and/or injury risk.

16. The wearable device of claim 15, wherein the biofeedback unit comprises a user interface device for user inputs.

17. The wearable device of claim 16, wherein the user inputs comprise height, weight, body mass index, age, gender, diet, training schedule, subjective pain/fatigue, bone cross-sectional area, bone geometry, bone density, bone composition, GPS position, altitude of the user and/or other personal health or demographic data.

18. The wearable device of claim 1, wherein one or more additional motion sensors are configured to be located on one or more additional segments of the user beyond the foot or shank.

19. The wearable device of claim 1, wherein the plurality of sensors further comprises one or more activity trackers.

20. A method for monitoring ankle moment, calf muscle force, and/or Achilles tendon force of a user using the wearable device of claim 1, comprising:

receiving information about biomechanical activity from the plurality of sensors;

estimating bio-information of the body structure based on the received information from the plurality of sensors; and communicating the estimated bio-information to the user and/or a party of interest.

* * * * *